US012600950B2

(12) United States Patent
Califano et al.

(10) Patent No.: US 12,600,950 B2
(45) Date of Patent: Apr. 14, 2026

(54) METHOD OF GENERATING MULTIPOTENT STEM CELLS

(71) Applicants: THE TRUSTEES OF COLUMBIA UNIVERSITY IN THE CITY OF NEW YORK, New York, NY (US); FUNDACIÓ CENTRE DE REGULACIÓ GENÒMICA, Barcelona (ES); INSTITUCIÓ CATALANA DE RECERCA I ESTUDIS AVANÇATS, Barcelona (ES)

(72) Inventors: Andrea Califano, New York, NY (US); Maria Pia Cosma, Barcelona (ES); Karthik Arumugam, Barcelona (ES)

(73) Assignees: THE TRUSTEES OF COLUMBIA UNIVERSITY IN THE CITY OF NEW YORK, New York, NY (US); FUNDACIÓ CENTRE DE REGULACIÓ GENÒMICA, Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 479 days.

(21) Appl. No.: 18/194,551

(22) Filed: Mar. 31, 2023

(65) Prior Publication Data

US 2024/0132845 A1    Apr. 25, 2024
US 2024/0228965 A9    Jul. 11, 2024

Related U.S. Application Data

(63) Continuation of application No. PCT/US2021/053161, filed on Oct. 1, 2021.

(Continued)

(51) Int. Cl.
C12N 5/0789    (2010.01)
C12N 15/86    (2006.01)

(52) U.S. Cl.
CPC ........... *C12N 5/0647* (2013.01); *C12N 15/86* (2013.01); *C12N 2501/40* (2013.01)

(58) Field of Classification Search
CPC .................................................. C12N 5/0647
See application file for complete search history.

(56) References Cited

U.S. PATENT DOCUMENTS

2010/0167291 A1*    7/2010    Rosenberg ........... C12Q 1/6881
                                                                    435/6.16
2012/0093832 A1*    4/2012    Brustle .................. A61K 35/30
                                                                    424/158.1

(Continued)

OTHER PUBLICATIONS

Alvarez Mariano J, Shen Yao, Giorgi Federico M, Lachmann Alexander, Ding B Belinda, Ye B Hilda, Califano Andrea, "Network-based inference of protein activity helps functionalize the genetic landscape of cancer", Nature Genetics, (Ju. 20, 2016), doi:10.1038/ng.3593, p. 3, XP055928339.

(Continued)

*Primary Examiner* — Mark L Shibuya
(74) *Attorney, Agent, or Firm* — FULLER IP LAW LLC; Scott H. Blackman

(57) ABSTRACT

The method of generating multipotent stem cells is a method for producing and/or expanding multipotent stem cells by delivering at least one reprogramming protein into somatic cells. The at least one reprogramming protein includes a Master Regulator (MR) protein, which may be BAZ2B, ZBTB20, ZMAT1, CNOT8, KLF12, DMTF1, HBP1, or FLI1. The bromodomain protein BAZ2B, in particular, was identified by first generating bi-species heterokaryons by fusing Tcf7l1$^{-/-}$ murine embryonic stem cells (ESCs) with human B-cell lymphocytes. Reprogramming of the B-cell (Continued)

nuclei to a multipotent state was tracked by human mRNA transcript profiling at multiple timepoints. Interrogation of a human B-cell regulatory network with gene expression signatures collected from such reprogramming time series identified eight candidate Master Regulator proteins, which were validated in human cord blood-derived hematopoietic progenitor and lineage-committed cells.

7 Claims, 31 Drawing Sheets

Specification includes a Sequence Listing.

Related U.S. Application Data

(60) Provisional application No. 63/086,265, filed on Oct. 1, 2020.

(56) References Cited

U.S. PATENT DOCUMENTS

2012/0214236 A1    8/2012   Bhatia
2023/0392165 A1*  12/2023   Vallier ................. A61K 35/545

OTHER PUBLICATIONS

Arumugam Karthik, Shin William, Schiavone Valentina, Vlahos Lukas, Tu Xiaochuan, Carnevali Davide, Kesner Jordan, Paull Evan O., Romo Neus, Subramaniam Prem, Worley Jeremy, Tan Xiangtian, Califano Andrea, Cosma Maria Pia, "The Master Regulator protein BAZ2B can reprogram human hematopoietic lineage-committed progenitors into a multipotent state", Cell Rep., (Dec. 8, 2020), doi:10.1016/j.celrep.2020.108474, pp. 1-10, XP055928342.
Aubry Soline, Shin William, Crary John F, Lefort Roger, Qureshi Yasir H, Lefebvre Celine, Califano Andrea, Shelanski Michael L, "Assembly and Interrogflliun of Alzheimer's Disease Genetic Networks Reveal Novel Regulators of Progression", PLOS ONE, (Mar. 17, 2015), doi:10.1371/journal.ponc.0120352, pp. 1-25, XP055928326.
Brady, "Early role for IL 6 signaling in IPS generation revealed by hetcrokaryon RNA-Seq", Nature Cell Biology, (Sep. 1, 2013), doi:10.1038/ncb2835, pp. 1244-1252, XP055867193.
Califano A., "Genetic strategy for reprogramming blood progenitors into transplantable stem cells", Innovation Columbia, (Jul. 28, 2020), p. 1, URL: innovation.columbia.edu/technologies/CU21021_genetic-strategy-for-reprogramming, (Dec. 29, 2021), XP055928318.
Patel Siddharth, Athirasala Avathamsa, Menezes Paula P., Ashwanikumar N., Zou Ting, Sahay Gaurav, Bertassoni Luiz E., "Messenger RNA Delivery for Tissue Engineering and Regenerative Medicine Applications", Tissue Engineering, (Jan. 21, 2019), vol. 25, No. 1-2, doi:10.1089/ten.tea.2017.0444, pp. 93-112, XP055928322.

* cited by examiner

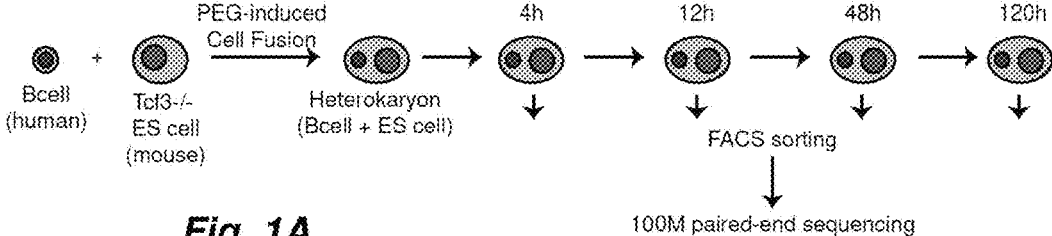
Fig. 1A
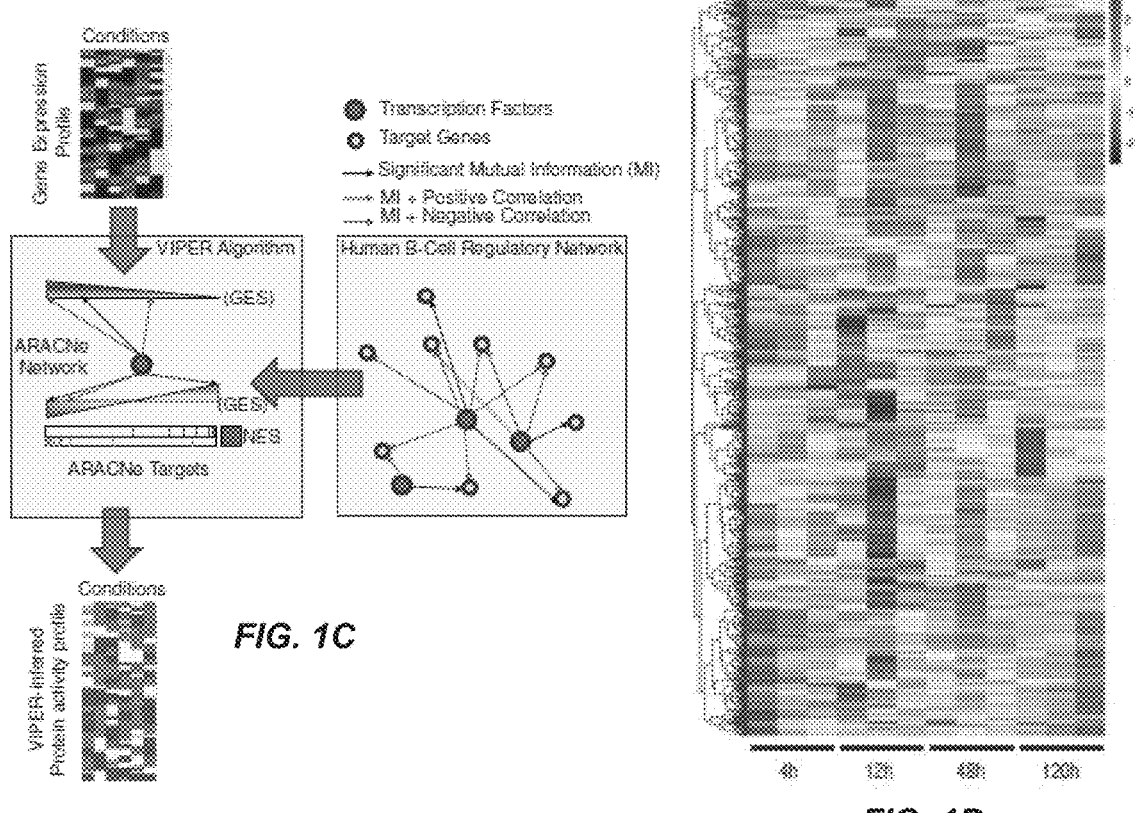
FIG. 1B
FIG. 1C
FIG. 1D

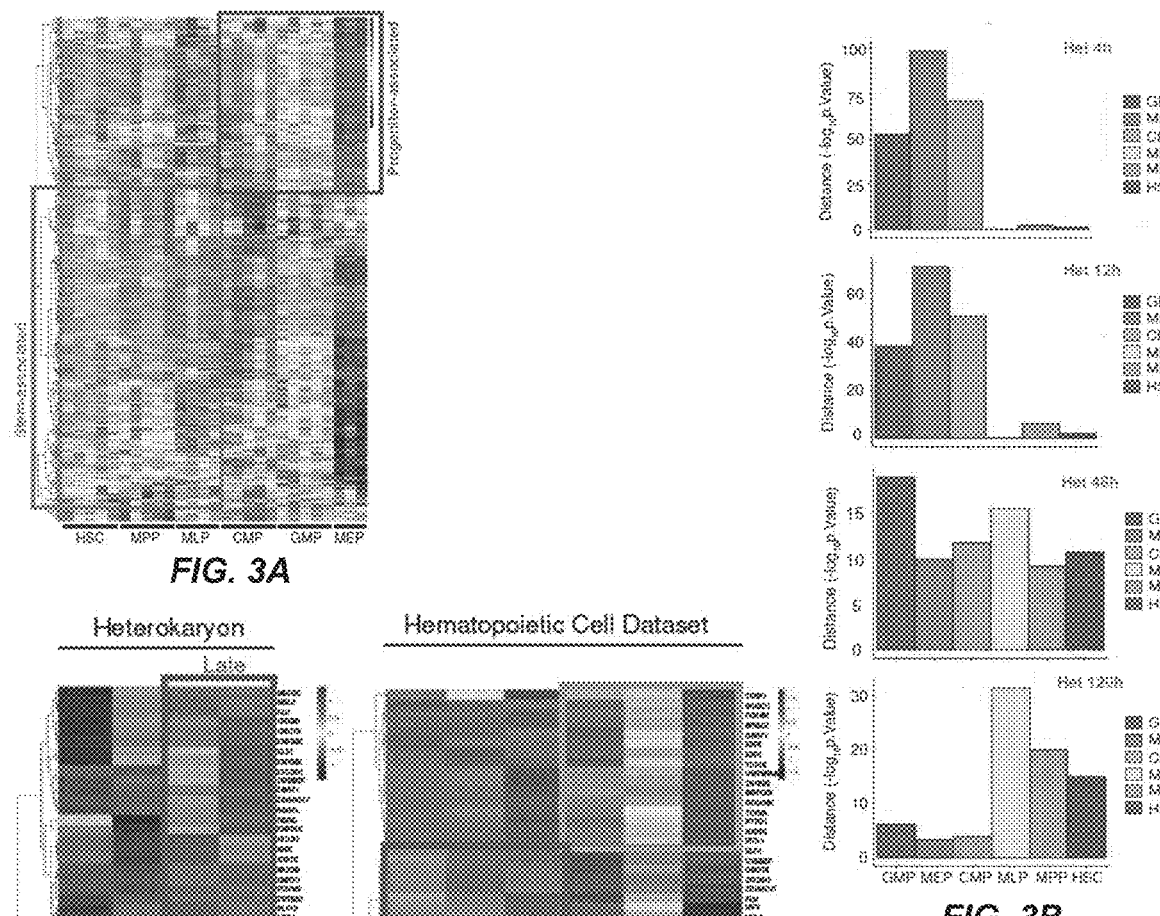
*FIG. 3A*
*FIG. 3B*
*FIG. 3C*
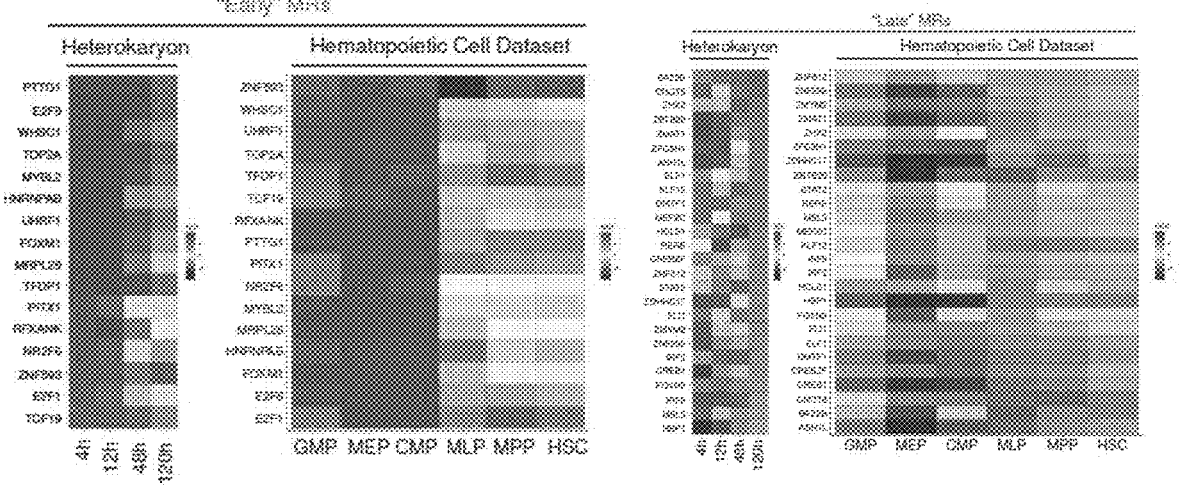
*FIG. 3D*                                    *FIG. 3E*

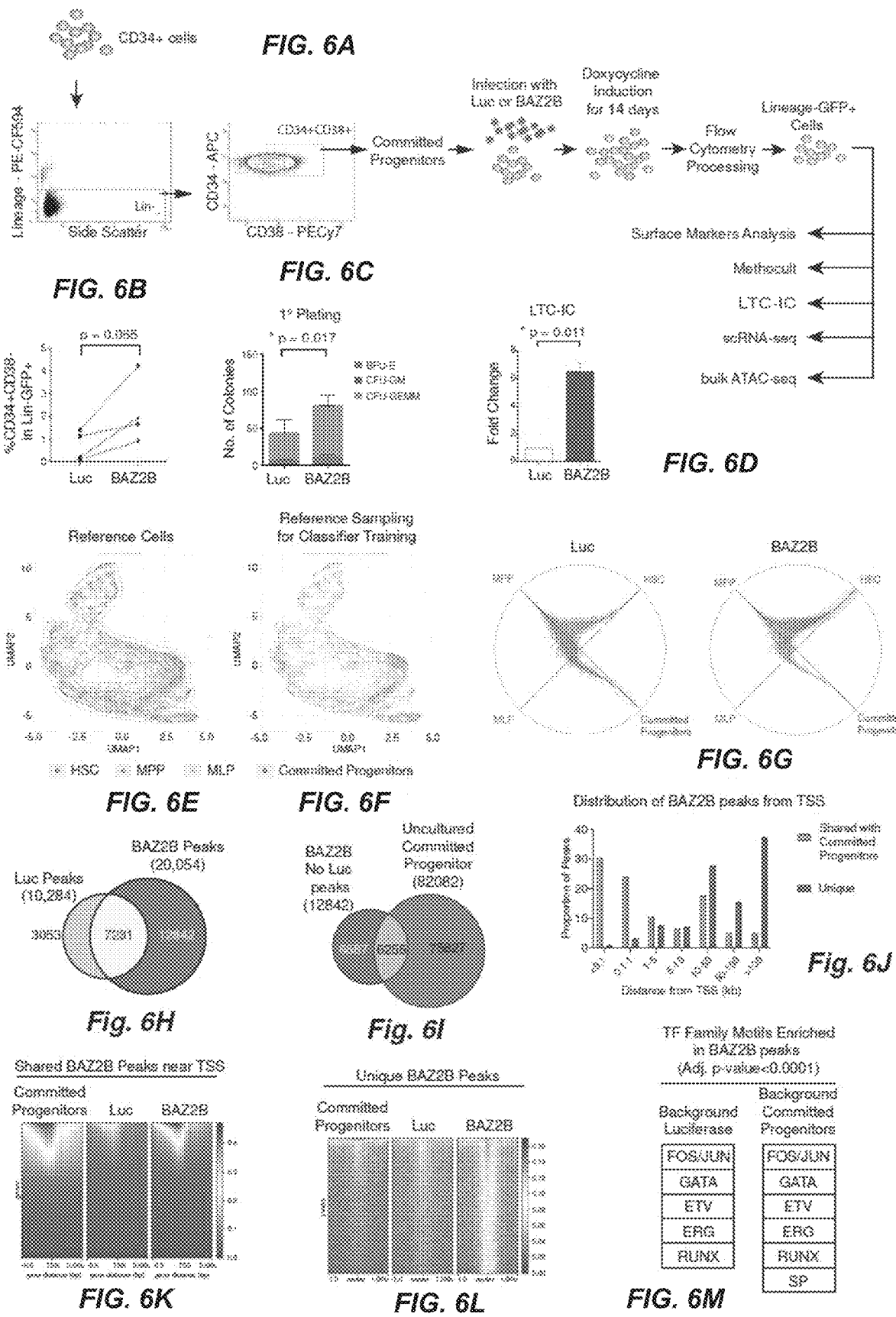

Bone marrow

Lineage Potential of BAZ2B-Induced Multipotent Progenitors

Hierarchical Clustering of Heterokaryons

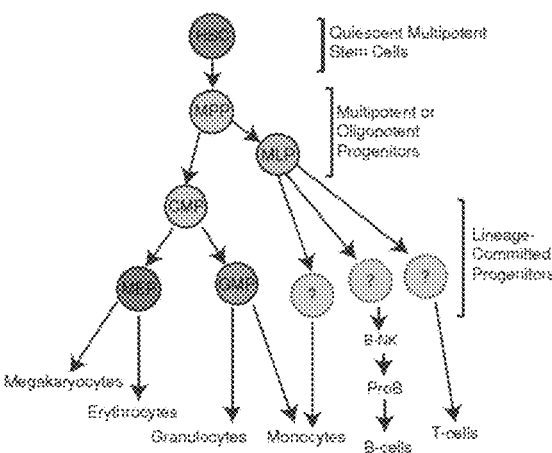
*FIG. 10A*
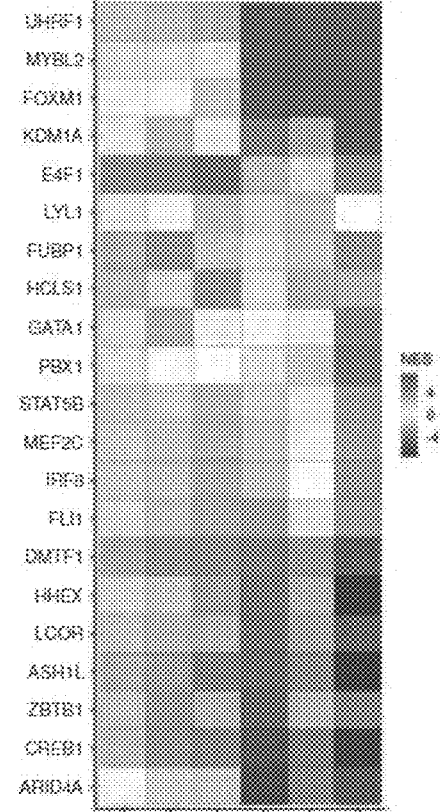
*FIG. 10B*
Hierarchical Clustering of the human hematopoietic lineage dataset
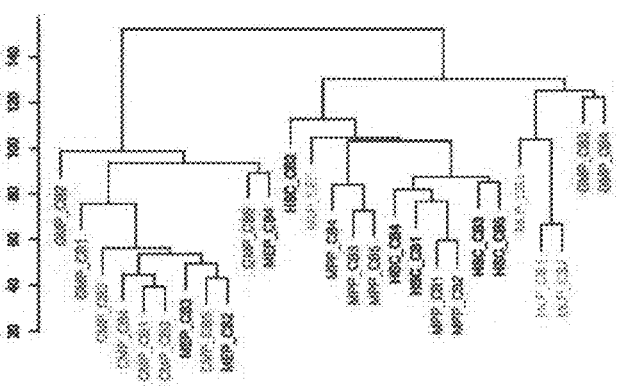
*FIG. 10C*
*FIG. 10D*
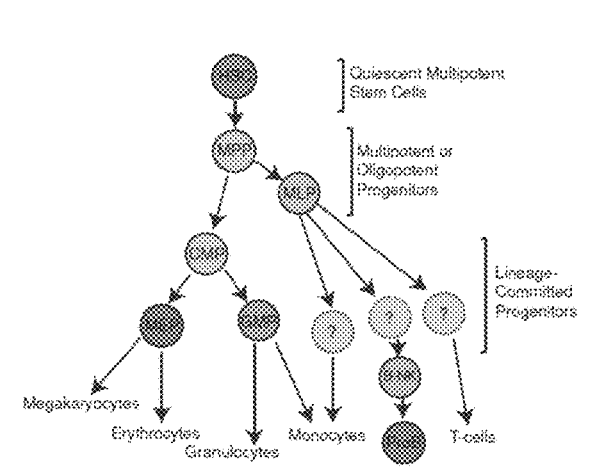
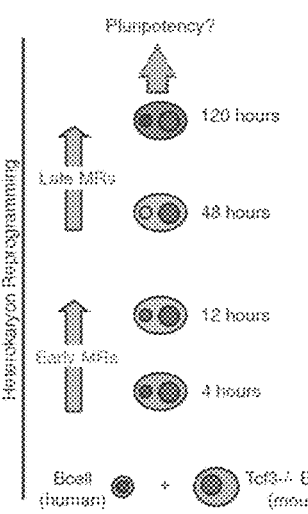
*FIG. 10E*

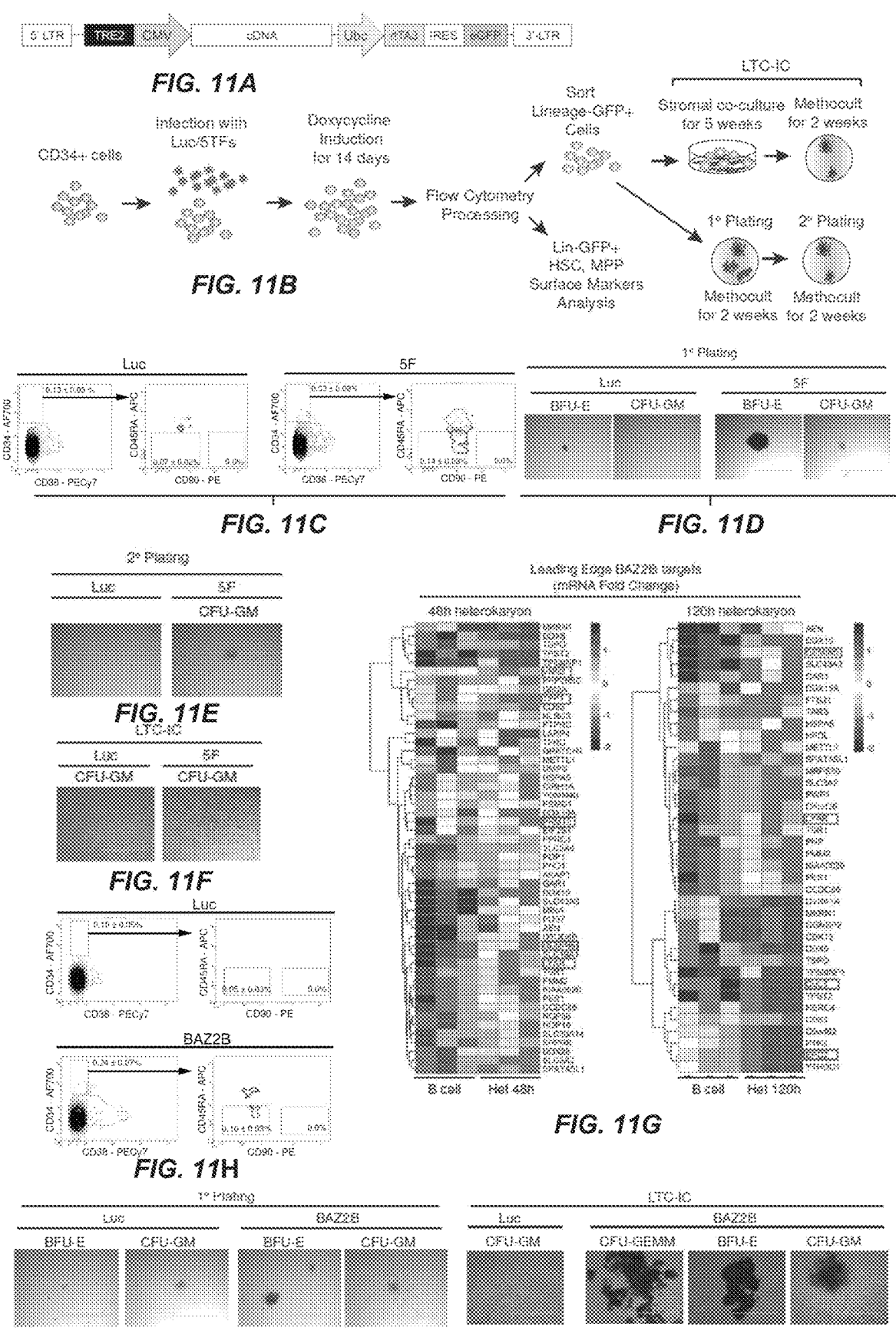

BAZ2b Promoter Proximal peaks shared with Committed Progenitors
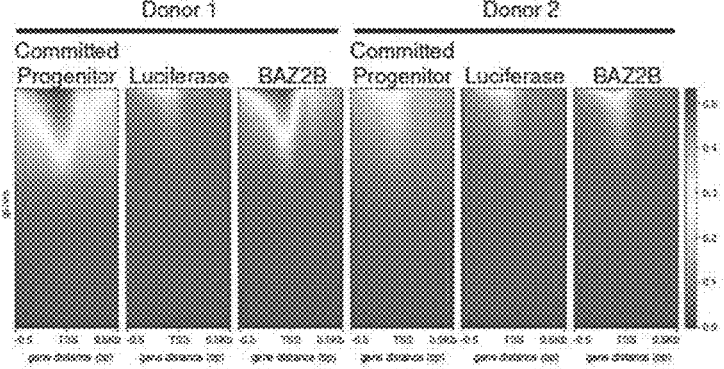
FIG. 14A
BAZ2b Unique peaks
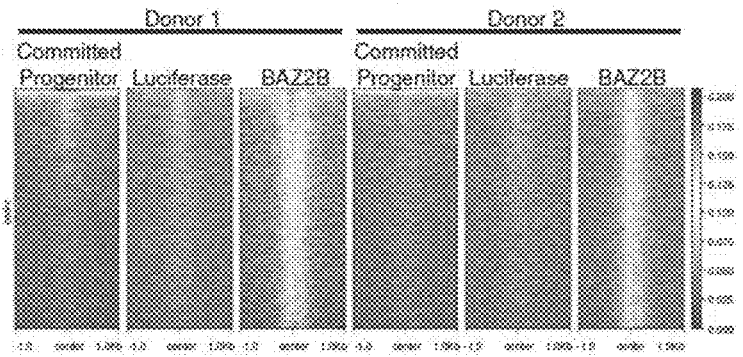
FIG. 14B
FIG. 14C
Spleen
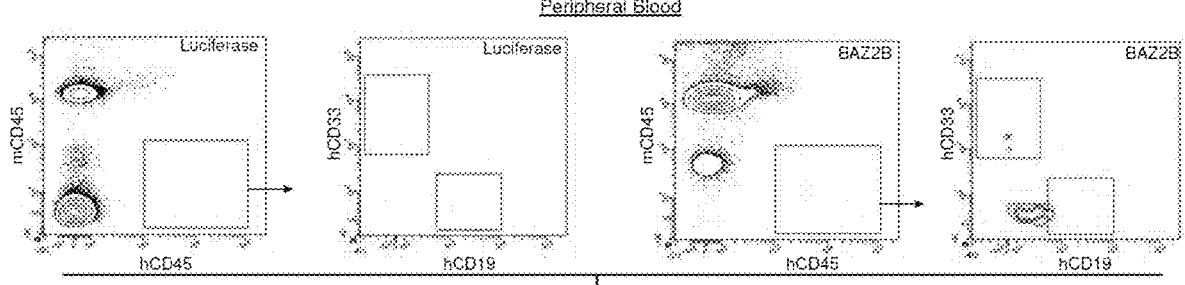
FIG. 14D
Peripheral Blood
FIG. 14E

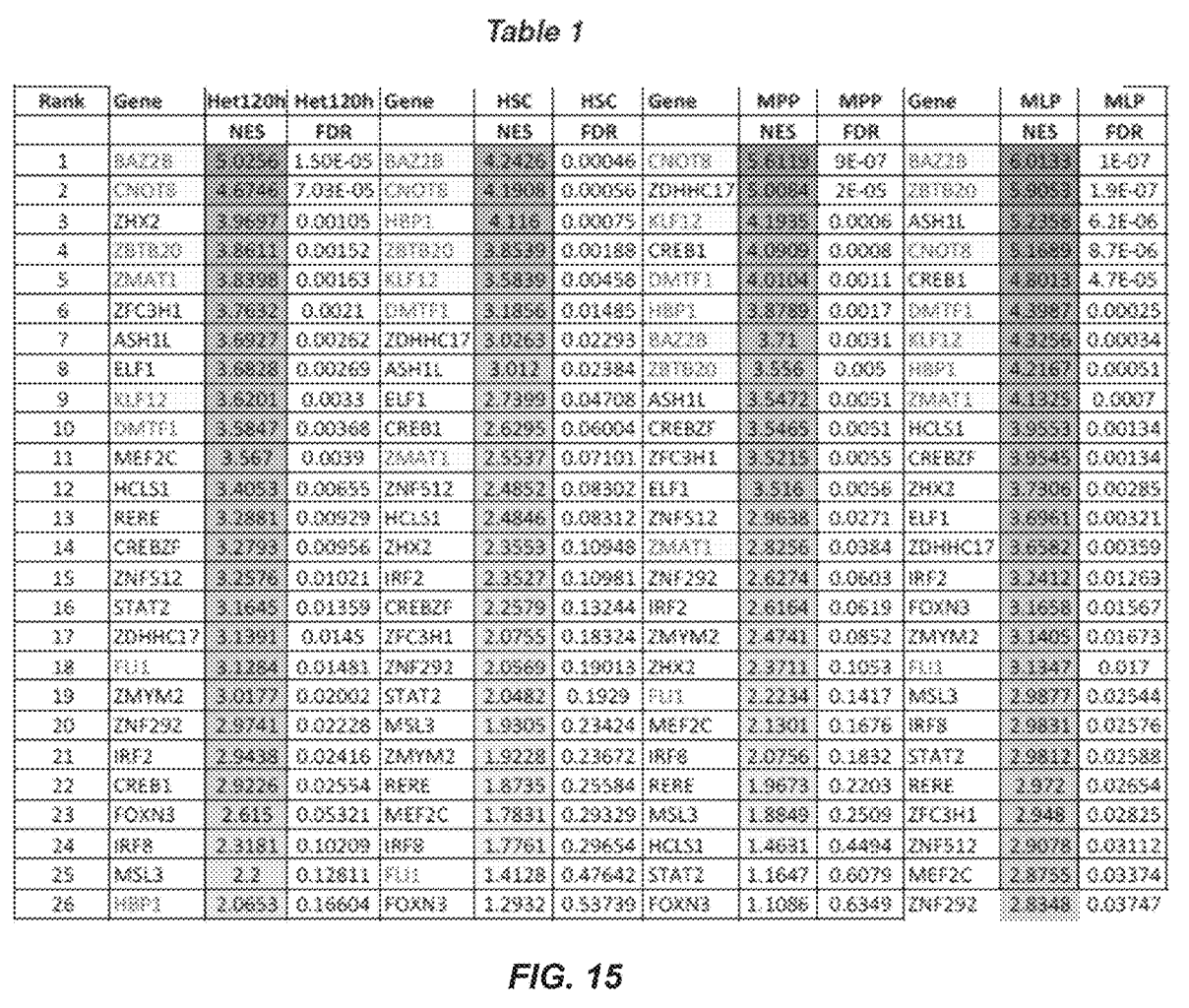

*Table 1*

| Rank | Gene | Het120h NES | Het120h FDR | Gene | HSC NES | HSC FDR | Gene | MPP NES | MPP FDR | Gene | MLP NES | MLP FDR |
|---|---|---|---|---|---|---|---|---|---|---|---|---|
| 1 | BAZ2B | | 1.50E-05 | BAZ2B | | 0.00046 | CNOT8 | | 9E-07 | BAZ2B | | 1E-07 |
| 2 | CNOT8 | | 7.03E-05 | CNOT8 | | 0.00056 | ZDHHC17 | | 2E-05 | ZBTB20 | | 1.9E-07 |
| 3 | ZHX2 | | 0.00105 | HBP1 | 4.118 | 0.00075 | ELF12 | 4.1958 | 0.0006 | ASH1L | | 6.2E-06 |
| 4 | ZBTB20 | | 0.00152 | ZBTB20 | | 0.00188 | CREB1 | | 0.0008 | CNOT8 | | 8.7E-06 |
| 5 | ZMAT1 | | 0.00163 | ELF12 | | 0.00458 | DMTF1 | 4.0164 | 0.0011 | CREB1 | | 4.7E-05 |
| 6 | ZFC3H1 | | 0.0021 | DMTF1 | | 0.01485 | HBP1 | 3.8789 | 0.0017 | DMTF1 | | 0.00025 |
| 7 | ASH1L | | 0.00262 | ZDHHC17 | | 0.02293 | BAZ2B | 3.71 | 0.0031 | ELF12 | | 0.00034 |
| 8 | ELF1 | | 0.00269 | ASH1L | 3.011 | 0.02384 | ZBTB20 | 3.558 | 0.005 | HBP1 | | 0.00051 |
| 9 | ELF12 | | 0.0033 | ELF1 | | 0.04708 | ASH1L | 3.5472 | 0.0051 | ZMAT1 | | 0.0007 |
| 10 | DMTF1 | | 0.00368 | CREB1 | 2.6295 | 0.06004 | CREBZF | | 0.0051 | HCLS1 | | 0.00134 |
| 11 | MEF2C | | 0.0039 | ZMAT1 | 2.5537 | 0.07101 | ZFC3H1 | | 0.0055 | CREBZF | | 0.00134 |
| 12 | HCLS1 | | 0.00655 | ZNF512 | 2.4852 | 0.08302 | ELF1 | | 0.0056 | ZHX2 | | 0.00285 |
| 13 | RERE | | 0.00929 | HCLS1 | 2.4846 | 0.08312 | ZNF512 | | 0.0271 | ELF1 | | 0.00321 |
| 14 | CREBZF | | 0.00956 | ZHX2 | 2.3553 | 0.10948 | ZMAT1 | | 0.0384 | ZDHHC17 | | 0.00359 |
| 15 | ZNF512 | | 0.01021 | IRF2 | 2.3527 | 0.10981 | ZNF292 | 2.6274 | 0.0603 | IRF2 | | 0.01263 |
| 16 | STAT2 | | 0.01359 | CREBZF | 2.2579 | 0.13244 | IRF2 | 2.6164 | 0.0619 | FOXN3 | | 0.01567 |
| 17 | ZDHHC17 | | 0.0145 | ZFC3H1 | 2.0755 | 0.18324 | ZMYM2 | 2.4741 | 0.0852 | ZMYM2 | | 0.01673 |
| 18 | FLI1 | | 0.01481 | ZNF292 | 2.0969 | 0.19013 | ZHX2 | 2.3711 | 0.1053 | FLI1 | | 0.017 |
| 19 | ZMYM2 | | 0.02002 | STAT2 | 2.0482 | 0.1929 | FLI1 | 2.2234 | 0.1417 | MSL3 | | 0.02544 |
| 20 | ZNF292 | | 0.02228 | MSL3 | 1.9305 | 0.23424 | MEF2C | 2.1301 | 0.1676 | IRF8 | | 0.02576 |
| 21 | IRF2 | | 0.02416 | ZMYM2 | 1.9228 | 0.23672 | IRF8 | 2.0756 | 0.1832 | STAT2 | | 0.02588 |
| 22 | CREB1 | | 0.02554 | RERE | 1.8735 | 0.25584 | RERE | 1.9673 | 0.2203 | RERE | 1.972 | 0.02654 |
| 23 | FOXN3 | 2.615 | 0.05321 | MEF2C | 1.7831 | 0.29329 | MSL3 | 1.8849 | 0.2509 | ZFC3H1 | | 0.02825 |
| 24 | IRF8 | | 0.10209 | IRF8 | 1.7761 | 0.29654 | HCLS1 | 1.4681 | 0.4494 | ZNF512 | | 0.03112 |
| 25 | MSL3 | 2.2 | 0.11811 | FLI1 | 1.4128 | 0.47642 | STAT2 | 1.1647 | 0.6079 | MEF2C | | 0.03374 |
| 26 | HBP1 | | 0.16604 | FOXN3 | 1.2932 | 0.53739 | FOXN3 | 1.1086 | 0.6349 | ZNF292 | | 0.03747 |

*FIG. 15*

*Table 2*

|  | TotalReads | Human.Unique | Mouse.Unique | Multi-mapping |
|---|---|---|---|---|
| Bcell | 28,273,008 | 27,680,415 | 1,765 | 590,828 |
| Bcell | 23,071,287 | 22,450,851 | 1,402 | 619,034 |
| Bcell | 25,572,699 | 25,020,566 | 1,461 | 550,672 |
| Het4h | 26,385,518 | 8,357,365 | 17,498,299 | 529,854 |
| Het4h | 33,172,158 | 9,984,775 | 22,655,854 | 531,529 |
| Het4h | 83,758,127 | 41,070,282 | 41,062,055 | 1,625,790 |
| Het12h | 71,139,709 | 32,242,448 | 37,825,136 | 1,072,125 |
| Het12h | 75,805,230 | 37,458,398 | 36,854,827 | 1,492,005 |
| Het12h | 78,824,375 | 39,022,278 | 38,117,926 | 1,684,171 |
| Het48h | 51,280,183 | 3,271,949 | 47,294,808 | 713,426 |
| Het48h | 51,742,113 | 3,034,489 | 47,850,548 | 857,076 |
| Het48h | 48,586,528 | 8,151,493 | 39,044,433 | 1,390,602 |
| Het120h | 63,139,366 | 1,115,469 | 60,562,409 | 1,461,488 |
| Het120h | 53,906,586 | 798,759 | 51,915,397 | 1,192,430 |
| Het120h | 67,176,421 | 754,427 | 65,038,187 | 1,383,807 |

*FIG. 16*

*Table 3*

|  | Total Reads | Human (Final) | Mouse (Final) |
|---|---|---|---|
| Bcell | 28,273,008 | 28,271,243 | 1,765 |
| Bcell | 23,071,287 | 23,069,885 | 1,402 |
| Bcell | 25,572,699 | 25,571,238 | 1,461 |
| Het4h | 26,385,518 | 8,670,944 | 17,714,574 |
| Het4h | 33,172,158 | 10,296,287 | 22,875,871 |
| Het4h | 83,758,127 | 41,925,026 | 41,833,101 |
| Het12h | 71,139,709 | 32,842,567 | 38,297,142 |
| Het12h | 75,805,230 | 38,254,324 | 37,550,906 |
| Het12h | 78,824,375 | 39,931,191 | 38,893,184 |
| Het48h | 51,280,183 | 3,674,748 | 47,605,435 |
| Het48h | 51,742,113 | 3,495,871 | 48,246,242 |
| Het48h | 48,586,528 | 8,858,769 | 39,727,759 |
| Het120h | 63,139,366 | 1,897,669 | 61,241,697 |
| Het120h | 53,906,586 | 1,506,793 | 52,399,793 |
| Het120h | 67,176,421 | 1,488,917 | 65,687,504 |

*FIG. 17*

Table 4

| | GreaterThan0 | GreaterThan1 | GreaterThan5 |
|---|---|---|---|
| Bcell | 17,029 | 16,062 | 14,418 |
| Bcell | 17,025 | 15,975 | 14,338 |
| Bcell | 17,057 | 16,048 | 14,443 |
| Het4h | 15,071 | 14,054 | 12,474 |
| Het4h | 15,281 | 14,362 | 12,827 |
| Het4h | 17,188 | 16,435 | 15,020 |
| Het12h | 17,214 | 16,561 | 15,084 |
| Het12h | 16,215 | 15,473 | 14,064 |
| Het12h | 16,456 | 15,653 | 14,239 |
| Het48h | 14,138 | 13,054 | 11,518 |
| Het48h | 14,192 | 13,072 | 11,451 |
| Het48h | 15,884 | 14,814 | 12,977 |
| Het120h | 13,410 | 12,028 | 9,817 |
| Het120h | 11,921 | 10,741 | 8,317 |
| Het120h | 11,211 | 9,536 | 6,359 |

FIG. 18

*Table 5*

|  | GreaterThan0 | GreaterThan1 | GreaterThan5 |
|---|---|---|---|
| Bcell | 134 | 71 | 34 |
| Bcell | 139 | 70 | 36 |
| Bcell | 126 | 68 | 30 |
| Het4h | 17,730 | 16,998 | 15,808 |
| Het4h | 17,662 | 17,236 | 15,895 |
| Het4h | 17,612 | 16,937 | 15,625 |
| Het12h | 17,708 | 17,154 | 15,887 |
| Het12h | 17,282 | 16,667 | 15,404 |
| Het12h | 17,366 | 16,776 | 15,448 |
| Het48h | 17,600 | 16,866 | 15,618 |
| Het48h | 17,763 | 17,132 | 15,893 |
| Het48h | 18,187 | 17,442 | 16,198 |
| Het120h | 18,247 | 17,605 | 16,492 |
| Het120h | 18,184 | 17,711 | 16,494 |
| Het120h | 18,296 | 17,682 | 16,567 |

*FIG. 19*

*Table 6*

| | Number of Significant MR candidates (FDR < 0.01) |
|---|---|
| 4-hours after cell-cell fusion | 169 |
| 12-hours after cell-cell fusion | 200 |
| 48-hours after cell-cell fusion | 106 |
| 120-hours after cell-cell fusion | 64 |

*FIG. 20*

*Table 7*

| Name | Het4h | Het12h | Het48h | Het120h |
|---|---|---|---|---|
| AATF | 4.543 | 1.518 | -2.372 | -1.330 |
| ARHGAP35 | 2.172 | 2.575 | 1.013 | 1.570 |
| ASH2L | 1.806 | 3.364 | 2.638 | 2.154 |
| ATAD2 | 4.171 | 6.800 | 2.323 | 2.134 |
| BUD31 | 4.873 | 5.863 | 1.518 | -1.323 |
| CARHSP1 | 3.324 | 4.407 | 6.150 | 2.710 |
| CBX2 | 4.873 | 4.176 | 1.070 | 0.305 |
| CCRN4L | 3.885 | 3.827 | -1.534 | -2.300 |
| CHAMP1 | 2.708 | 3.371 | 0.968 | 0.815 |
| CREB3 | 2.399 | 2.437 | 2.537 | 0.031 |
| CREM | 1.123 | 3.672 | -1.453 | -3.387 |
| DMAP1 | 2.799 | 2.849 | 1.741 | -0.550 |
| E2F1 | 5.530 | 4.551 | 1.604 | -0.545 |
| E2F2 | 6.573 | 6.011 | 3.385 | 1.818 |
| E2F6 | 3.763 | 3.417 | -5.651 | -4.576 |
| E2F7 | 7.408 | 8.296 | 5.779 | 2.270 |
| E2F8 | 8.996 | 10.467 | 6.726 | 4.615 |
| ECSIT | 5.210 | 3.106 | 1.366 | -1.422 |
| ENO1 | 4.656 | 2.521 | 0.072 | 0.354 |
| FOXM1 | 10.100 | 8.889 | 5.362 | 2.396 |
| FUBP1 | 4.084 | 4.318 | 1.374 | 3.333 |
| GABPB1 | 2.543 | 4.371 | -2.338 | -3.235 |
| GTF2H4 | 4.341 | 3.410 | 2.516 | 0.312 |
| GTF2IRD1 | 3.562 | 3.800 | 0.011 | 1.608 |
| GZF1 | 1.104 | 4.556 | -0.266 | -0.158 |
| HDAC1 | 1.816 | 1.956 | 4.663 | 3.990 |
| HDGF | 5.749 | 5.919 | 0.481 | 0.368 |
| HLTF | 3.882 | 6.754 | 4.518 | 3.706 |
| HMGA1 | 5.444 | 2.151 | 2.314 | 0.207 |
| HMGB1 | 2.907 | 5.386 | 3.323 | 3.378 |
| HMGB2 | 6.350 | 8.586 | 5.777 | 4.188 |
| HMGN5 | 2.850 | 4.127 | 1.600 | -0.007 |
| HNRNPAB | 8.661 | 8.957 | 2.849 | 2.358 |
| HSF2 | 1.512 | 3.358 | -1.888 | -0.530 |
| IKZF5 | 2.813 | 3.714 | -2.045 | 0.500 |
| ILF2 | 5.922 | 5.817 | -0.782 | -0.813 |
| ILF3 | 5.285 | 2.222 | -1.329 | 0.691 |
| KDM1A | 5.808 | 3.711 | 2.956 | 2.299 |

| MAZ | 6.143 | 1.368 | 0.058 | -0.150 |
|---|---|---|---|---|
| MNX1 | 2.082 | 2.890 | 1.703 | 1.037 |
| MRPL28 | 8.491 | 7.121 | 3.800 | 0.993 |
| MPRF | 3.248 | 3.290 | -4.592 | -4.436 |
| MTA2 | 4.257 | 3.824 | -0.785 | -0.291 |
| MXD3 | 2.041 | 2.545 | 3.225 | 2.004 |
| MYBL2 | 8.946 | 8.727 | 6.145 | 3.542 |
| NAT14 | 4.136 | 2.389 | 2.491 | -0.073 |
| NFYA | 2.557 | 1.697 | 0.165 | 1.012 |
| NR2F6 | 8.088 | 5.415 | 0.910 | 2.198 |
| PA2G4 | 5.216 | 3.137 | -4.946 | -5.014 |
| PHF5A | 3.685 | 4.654 | 0.761 | -0.201 |
| PITX1 | 6.277 | 4.879 | -0.461 | -0.559 |
| PLAGL2 | 4.208 | 2.498 | -3.272 | -2.731 |
| PREB | 3.870 | 4.164 | 1.290 | -0.156 |
| PRKDC | 8.401 | 8.080 | 1.973 | 4.338 |
| PSMC3IP | 5.789 | 7.087 | 0.451 | 0.063 |
| PTTG1 | 8.772 | 10.245 | 8.583 | 4.634 |
| PURB | 3.587 | 5.602 | -0.988 | -3.163 |
| RFXANK | 8.241 | 7.156 | 3.805 | 0.354 |
| RFXAP | 2.881 | 3.701 | 1.413 | 1.778 |
| SARNP | 8.199 | 7.567 | 5.038 | 1.473 |
| SCMH1 | 6.303 | 3.742 | 3.047 | 3.094 |
| SMARCA4 | 4.092 | 1.527 | 1.458 | 1.221 |
| TADA2A | 2.930 | 2.637 | -1.924 | -1.838 |
| TAF12 | 1.808 | 4.715 | 3.383 | 1.100 |
| TAF1B | 3.813 | 5.887 | -0.455 | -0.813 |
| TAF5 | 4.787 | 6.774 | 0.146 | -3.914 |
| TAF9 | 4.098 | 7.709 | 0.480 | -0.473 |
| TAF9B | 1.886 | 3.234 | 0.295 | 0.821 |
| TCF19 | 5.102 | 5.239 | 4.705 | 2.881 |
| TCF3 | 3.128 | 1.439 | 2.462 | 1.211 |
| TFAM | 4.050 | 6.567 | -1.845 | -0.658 |
| TFAP4 | 3.058 | 3.616 | -0.240 | 0.241 |
| TFDP1 | 6.924 | 8.827 | 6.414 | 4.172 |
| TFDP2 | 2.218 | 3.585 | -0.497 | -0.559 |
| THAP7 | 3.727 | 1.292 | -0.877 | -1.835 |
| TOP2A | 8.939 | 10.128 | 8.888 | 4.796 |
| UHRF1 | 9.938 | 9.328 | 6.130 | 4.017 |
| WHSC1 | 8.589 | 7.152 | 4.670 | 2.999 |
| YBX1 | 6.092 | 8.491 | 2.652 | 2.488 |

21C

*Table 8*

| Name | Het4h | Het12h | Het48h | Het120h |
|---|---|---|---|---|
| AKNA | -2.825 | -6.503 | 3.724 | 2.897 |
| ALS2CR8 | -2.328 | 0.183 | 2.050 | 2.418 |
| ASH1L | -4.155 | -3.424 | 1.498 | 3.683 |
| BAZ2B | -3.148 | -2.705 | 4.888 | 5.028 |
| BCL11A | -2.983 | -2.377 | 2.987 | 2.243 |
| CBFA2T2 | -1.138 | -3.141 | 2.202 | 2.715 |
| CBFA2T3 | 0.220 | -1.581 | 2.893 | 2.103 |
| CGGBP1 | -3.611 | 0.289 | 1.996 | 2.655 |
| CNOT8 | -3.093 | -0.733 | 4.056 | 4.675 |
| CREB1 | -4.687 | -2.142 | 1.573 | 2.823 |
| CREBZF | -2.112 | -1.460 | 1.054 | 3.279 |
| DMTF1 | -3.816 | -2.914 | 3.015 | 3.565 |
| ELF1 | -2.013 | -0.312 | 1.495 | 3.883 |
| FLI1 | -2.834 | -0.762 | 3.688 | 3.128 |
| FOXN3 | -2.498 | -2.778 | 3.013 | 2.615 |
| FOXO1 | -0.965 | -0.864 | 2.860 | 2.862 |
| GATA1 | -3.216 | -3.715 | 2.861 | 1.394 |
| GTF2I | 0.776 | 0.112 | 1.755 | 3.522 |
| HBP1 | -5.360 | -3.834 | 2.862 | 2.065 |
| HCLS1 | -1.455 | -2.715 | 5.913 | 3.405 |
| HDAC1 | 1.818 | 1.956 | 4.663 | 3.900 |
| IFI16 | -3.810 | -3.397 | 1.842 | 1.461 |
| IRF2 | -1.918 | -2.978 | 4.728 | 2.944 |
| IRF8 | -3.875 | -3.886 | 4.545 | 2.318 |
| IRF9 | -5.574 | -7.158 | 2.826 | 1.340 |
| KLF12 | -2.864 | -1.214 | 4.590 | 3.630 |
| LYL1 | -0.725 | -1.580 | 5.068 | 2.773 |
| MEF2C | -2.620 | -0.278 | 3.804 | 3.567 |
| MSL3 | -3.131 | -1.231 | 2.765 | 2.200 |
| MYBL1 | 0.010 | 1.085 | 4.805 | 3.233 |
| NR2C2 | -4.493 | -3.318 | 0.579 | 2.628 |
| POU2F2 | -1.903 | -4.024 | 2.881 | 1.368 |
| RBL2 | -6.015 | -5.206 | 2.421 | 2.534 |
| RERE | -0.356 | -3.939 | 2.291 | 3.268 |
| RFX5 | -2.632 | -2.376 | 3.778 | 2.704 |
| SP140 | -3.840 | -3.315 | 3.101 | 0.856 |
| SPI1 | 1.393 | -1.683 | 3.842 | 1.262 |
| SPIB | 0.005 | -0.088 | 4.447 | 2.089 |

| | | | | |
|---|---|---|---|---|
| STAT2 | -1.082 | -2.467 | 4.916 | 3.165 |
| STAT5B | -1.264 | -0.868 | 2.801 | 2.955 |
| STAT6 | -1.631 | -5.485 | 2.694 | 1.077 |
| TADA3 | 1.184 | 0.214 | 4.372 | 2.056 |
| TAF10 | -1.453 | -2.289 | 5.066 | 2.162 |
| TCEAL1 | -2.477 | -0.754 | 2.264 | 1.686 |
| TFEB | -1.576 | -2.273 | 2.782 | 1.377 |
| ZBTB20 | -4.185 | -3.492 | 3.746 | 3.861 |
| ZC3H6 | -3.716 | -1.188 | 1.829 | 2.028 |
| ZCCHC11 | -3.312 | -3.614 | 2.095 | 2.060 |
| ZCCHC8 | -3.229 | -0.822 | 2.899 | 2.390 |
| ZDHHC17 | -3.766 | -3.623 | 0.806 | 3.139 |
| ZFC3H1 | -3.625 | -3.812 | 0.480 | 2.763 |
| ZFP161 | -2.205 | 0.638 | 3.708 | 3.302 |
| ZFP90 | -4.046 | -4.074 | 2.092 | 1.380 |
| ZFYVE21 | -0.369 | -0.867 | 2.805 | 1.661 |
| ZHX2 | -1.318 | -1.112 | 4.898 | 3.970 |
| ZMAT1 | -4.236 | -3.826 | 2.493 | 3.840 |
| ZMYM3 | -3.633 | -1.092 | 1.146 | 3.018 |
| ZNF292 | -3.693 | -2.285 | 1.987 | 2.974 |
| ZNF395 | 0.752 | -0.306 | 3.015 | 2.023 |
| ZNF512 | -0.888 | -2.147 | 1.529 | 3.258 |
| ZNF581 | 1.701 | 0.888 | 3.640 | 1.530 |
| ZNF611 | -2.437 | -2.978 | 1.940 | 2.683 |
| ZNF652 | -2.629 | -0.104 | 1.973 | 2.730 |
| ZNF763 | -2.319 | -2.089 | 2.378 | 1.490 |
| ZSWIM8 | -2.706 | -2.172 | 1.956 | 2.817 |

Table 9

| | Gene | | Gene |
|---|---|---|---|
| 1 | CD74 | 24 | CD53 |
| 2 | HSPA5 | 25 | PNRC1 |
| 3 | DNTTIP2 | 26 | HHEX |
| 4 | IRAK3 | 27 | RHOC |
| 5 | PIK3IP1 | 28 | RBPMS |
| 6 | XBP1 | 29 | PSTPD8 |
| 7 | RIPK2 | 30 | STX3 |
| 8 | EEF1D | 31 | LAIR1 |
| 9 | BIRC2 | 32 | UBB |
| 10 | SELENOK | 33 | FOS |
| 11 | TMEM59 | 34 | MLLT3 |
| 12 | DUSP1 | 35 | DDIT3 |
| 13 | SOCS2 | 36 | TAF7 |
| 14 | FOSB | 37 | HLA-DQB1 |
| 15 | ZFP36 | 38 | GATA2 |
| 16 | BST2 | 39 | MAFF |
| 17 | JUND | 40 | HLA-DRB1 |
| 18 | RNF138 | 41 | EVL |
| 19 | LMO2 | 42 | SVIP |
| 20 | ITM2B | 43 | UBBA |
| 21 | GYPC | 44 | GPSM3 |
| 22 | APP | 45 | VAMP2 |
| 23 | PRKACB | 46 | HLA-DPB1 |

FIG. 23

*Table 10*

| | Motif Clusters | No of Motifs | p val | adj pval |
|---|---|---|---|---|
| 1 | JUN(var.2),BACH2,FOSL1,JUNB,JUND,FOSL1::JUNB,FOSL1::JUN,FOS::JUND,FOSL2::JUN,FOS::JUNB,JDP2,NFE2,FOS,BATF3,BATF,BATF::JUN,FOSL2,JUN::JUNB,FOSL1::JUND,FOS::JUN,FOSL2::JUND,FOSB::JUNB,FOSL2::JUNB,NFE2L2,MAF::NFE2,BACH1,MAFK,NFE2L1 | 28 | 1.21E-08 | 8.23E-05 |
| 2 | LHX2,LHX6,HOXA6,MEOX2,MEOX1,EVX1,EVX2,GSX1,HOXB3,MNX1,EN2,LBX2,ESX1,MIXL1,ALX3,NKX6-3,HOXC8,HOXA1,HOXB6,NKX6-1,NKX6-2,HOXA4,HOXB4,HOXC4,HOXD4,VAX1,VAX2,GSX2,HOXB2,PDX1,LHX1,EN1,DRGX,SHOX,UNCX,RAX2,DLX6,MSX2,MSX1,BARX1,BSX,HOXB6,HOXA7,HOXB6,HOXD8 | 45 | 2.20E-07 | 0.001481 |
| 3 | NFYB,NFYA,NFYC | 3 | 5.10E-07 | 0.00358 |
| 4 | FOS::JUN(var.2),FOSL1::JUND(var.2),FOSB::JUNB(var.2),FOSL1::JUN(var.2),JUN::JUNB(var.2),FOSL2::JUN(var.2),FOSB::JUN | 7 | 4.71E-07 | 0.002271 |
| 5 | POU5F1B,POU3F4,POU2F1,POU1F1,POU3F3,POU3F2,POU3F1 | 7 | 1.76E-07 | 0.000855 |
| 6 | ONECUT1,CUX1,CUX2 | 3 | 2.87E-06 | 0.005303 |
| 7 | KLF5,KLF15,KLF3,KLF2,KLF6,KLF14,KLF10,KLF16,KLF11,SP3,SP8,SP9 | 12 | 1.37E-16 | 1.57E-12 |
| 8 | MEIS2(var.2),PBX2,MEIS1(var.2) | 3 | 3.10E-07 | 0.001526 |
| 9 | ATF4,CEBPG(var.2) | 2 | 3.01E-11 | 1.29E-07 |
| 10 | CEBPA,HLF,NFIL3 | 3 | 1.57E-07 | 0.000804 |
| 11 | KLF4,MAZ,ZNF148 | 3 | 2.51E-07 | 0.002263 |
| 12 | GATA1,GATA6,GATA2,GATA4,GATA3,GATA5 | 6 | 1.72E-21 | 1.87E-17 |
| 13 | EGR2,EGR3,EGR1 | 3 | 3.78E-07 | 0.001981 |
| 14 | SP2,SP4,SP1 | 3 | 5.37E-14 | 3.23E-10 |
| 15 | POU4F3,POU3F1 | 2 | 1.34E-07 | 0.000877 |
| 16 | DMRTA2,DMRT3 | 2 | 7.15E-07 | 0.003419 |
| 17 | GSC2,DPRX | 2 | 4.35E-08 | 0.000428 |
| 18 | PHOX2B,PHOX2A,DUXA | 3 | 4.96E-13 | 2.12E-09 |
| 19 | KLF9 | 1 | 1.91E-07 | 0.00233 |
| 20 | CEBPE,DBP | 2 | 4.96E-06 | 0.010278 |
| 21 | POU5F1(var.2) | 1 | 3.40E-08 | 2.64E-05 |

| | Motif Clusters | No of Motifs | p val | adj pval |
|---|---|---|---|---|
| 22 | FOXB1 | 1 | 4.13E-09 | 3.99E-05 |
| 23 | ZBTB14 | 1 | 1.42E-12 | 1.23E-08 |
| 24 | CTCF,CTCFL | 2 | 1.89E-11 | 2.58E-07 |
| 25 | BARX2 | 1 | 3.55E-10 | 2.93E-06 |
| 26 | NRF1 | 1 | 3.24E-21 | 1.54E-17 |
| 27 | NKX3-1 | 1 | 2.57E-08 | 0.000123 |
| 28 | MITF,TFE3 | 2 | 1.12E-08 | 0.005905 |
| 29 | HOXA9 | 1 | 2.42E-06 | 0.0143 |
| 30 | GATA1::TAL1 | 1 | 1.73E-10 | 5.37E-07 |
| | Total No. of Motifs | 152 | | |

Figure 25A:
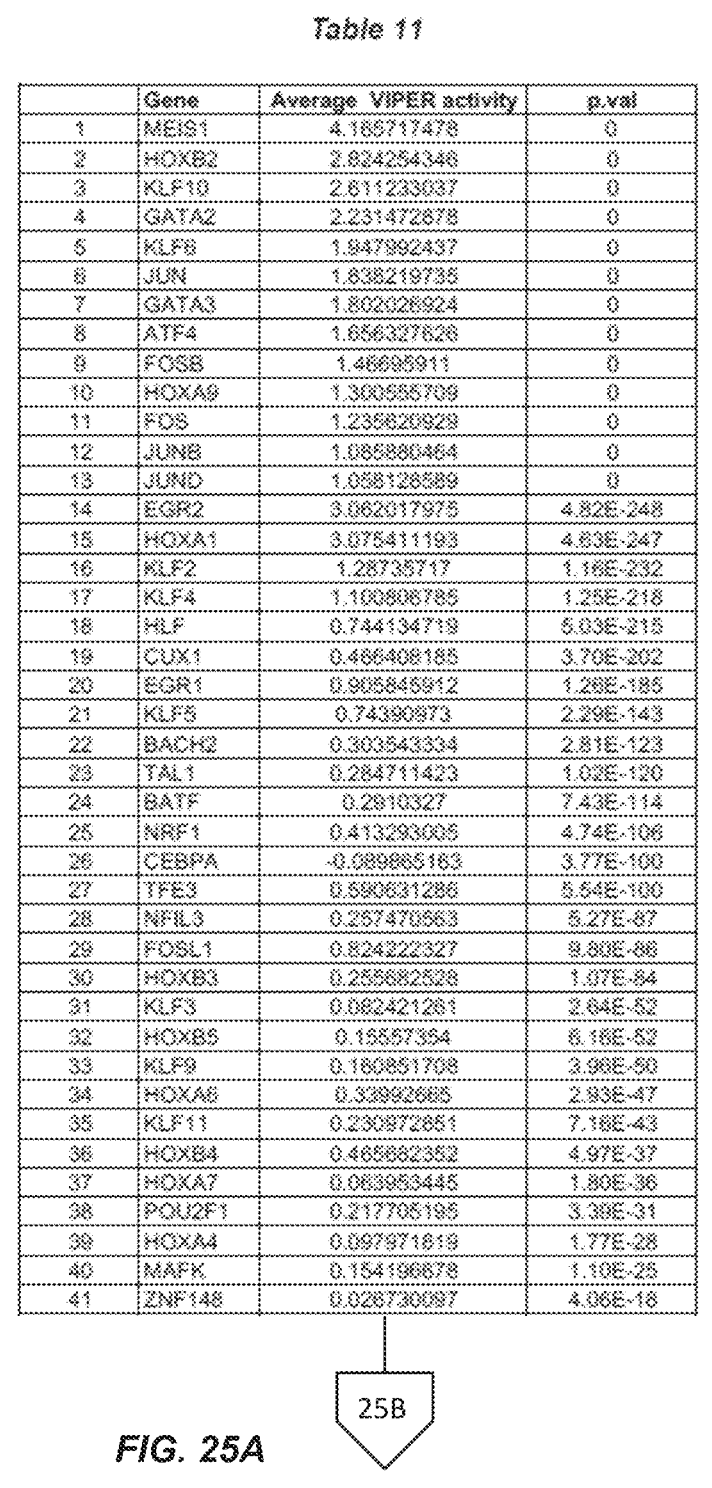

*Table 11*

|  | Gene | Average VIPER activity | p.val |
|---|---|---|---|
| 1 | MEIS1 | 4.165717478 | 0 |
| 2 | HOXB2 | 2.624254348 | 0 |
| 3 | KLF10 | 2.611233037 | 0 |
| 4 | GATA2 | 2.231472878 | 0 |
| 5 | KLF6 | 1.947982437 | 0 |
| 6 | JUN | 1.838219736 | 0 |
| 7 | GATA3 | 1.802026924 | 0 |
| 8 | ATF4 | 1.656337628 | 0 |
| 9 | FOSB | 1.46695911 | 0 |
| 10 | HOXA9 | 1.300585709 | 0 |
| 11 | FOS | 1.235620929 | 0 |
| 12 | JUNB | 1.085860464 | 0 |
| 13 | JUND | 1.088126589 | 0 |
| 14 | EGR2 | 3.062017975 | 4.82E-248 |
| 15 | HOXA1 | 3.075411193 | 4.63E-247 |
| 16 | KLF2 | 1.28735717 | 1.16E-232 |
| 17 | KLF4 | 1.100808786 | 1.25E-218 |
| 18 | HLF | 0.744134719 | 6.03E-215 |
| 19 | CUX1 | 0.466408185 | 3.70E-202 |
| 20 | EGR1 | 0.965845912 | 1.26E-185 |
| 21 | KLF5 | 0.74390873 | 2.39E-143 |
| 22 | BACH2 | 0.303543334 | 2.81E-123 |
| 23 | TAL1 | 0.284711423 | 1.02E-120 |
| 24 | BATF | 0.2910327 | 7.43E-114 |
| 25 | NRF1 | 0.413293005 | 4.74E-108 |
| 26 | CEBPA | -0.089985163 | 3.77E-100 |
| 27 | TFE3 | 0.590631286 | 5.54E-100 |
| 28 | NFIL3 | 0.257470563 | 5.27E-87 |
| 29 | FOSL1 | 0.824222327 | 9.88E-86 |
| 30 | HOXB3 | 0.255682528 | 1.07E-84 |
| 31 | KLF3 | 0.082421261 | 3.64E-53 |
| 32 | HOXB5 | 0.15557394 | 6.16E-53 |
| 33 | KLF9 | 0.180851708 | 3.98E-50 |
| 34 | HOXA6 | 0.33992685 | 2.83E-47 |
| 35 | KLF11 | 0.230872651 | 7.16E-43 |
| 36 | HOXB4 | 0.465862352 | 4.97E-37 |
| 37 | HOXA7 | 0.083953445 | 1.80E-36 |
| 38 | POU2F1 | 0.217705195 | 3.38E-31 |
| 39 | HOXA4 | 0.097971819 | 1.77E-28 |
| 40 | MAFK | 0.154196878 | 1.10E-26 |
| 41 | ZNF148 | 0.028730897 | 4.05E-18 |

| | Gene | Average  VIPER activity | p.val |
|---|---|---|---|
| 42 | KLF16 | 0.00495424 | 1.09E-17 |
| 43 | CEBPG | 0.022724508 | 2.48E-16 |
| 44 | SP1 | -0.108364716 | 5.20E-15 |
| 45 | FOSL2 | 0.029081083 | 5.43E-08 |
| 46 | DBP | -0.116160468 | 1.28E-08 |
| 47 | PBX2 | -0.168428132 | 9.43E-06 |
| 48 | NFE2L1 | -0.101142318 | 0.004423078 |
| 49 | NFYB | -0.13381193 | 0.880102118 |
| 50 | NFE2 | -0.244520837 | 0.994630511 |
| 51 | NFE2L2 | -0.02996747 | 0.997284523 |
| 52 | SP3 | -0.103008973 | 0.999631991 |
| 53 | CTCF | -0.133464911 | 0.999959365 |
| 54 | NFYC | -0.018464373 | 0.999999953 |
| 55 | SP2 | -0.173251666 | 1 |
| 56 | MAZ | -0.541410864 | 1 |
| 57 | GATA1 | -1.923387595 | 1 |

METHOD OF GENERATING MULTIPOTENT STEM CELLS

CROSS-REFERENCE TO RELATED APPLICATIONS

This application is a continuation of PCT Patent Application No. PCT/US2021/053161, filed Oct. 1, 2021, which claims priority to U.S. Provisional Patent Application No. 63/086,265, filed on Oct. 1, 2020, the entirety of the disclosures of which are hereby incorporated by this reference.

GOVERNMENT LICENSE RIGHTS

This invention was made with U.S. government support under grant no. 5R35CA197745, awarded by the National Institutes of Health. The U.S. government has certain rights to the invention.

INCORPORATION-BY-REFERENCE OF MATERIAL ELECTRONICALLY FILED

The official copy of the sequence listing is submitted electronically in ST.26 XML format having the file name "44010-075US-PAT.xml" created on Mar. 31, 2023, and having a size of 8,861 bytes, and is filed concurrently with the specification. The Sequence Listing ST.26 XML file is part of the specification and is herein incorporated by reference in its entirety.

TECHNICAL FIELD

The disclosure of the present patent application relates to the generation of multipotent stem cells from somatic cells, and particularly to a method of generating multipotent stem cells using protein transduction or other suitable means.

BACKGROUND ART

Early events driving somatic cell reprogramming to pluripotency can be effectively elucidated using cell-to-cell fusion approaches. Specifically, in vitro fusion of somatic cells with embryonic germ cells or embryonic stem cells (ESCs) has been shown to reprogram somatic nuclei to a pluripotent state. Consistently, cell fusion was shown to play a physiological role during in vivo regeneration of several tissues such as liver, brain and retina after injury.

Cell hybrids retaining intact multi-nuclear structure after fusion are also known as heterokaryons. Bi-species heterokaryons, derived from fusion between cells of two different species, have been used to study nuclear reprogramming by monitoring species-specific gene expression changes in time-dependent fashion. For instance, genome-wide expression profiling of fusion products between murine and human cells helped elucidate early reprogramming events in fibroblasts.

A major drawback with such studies, however, is that identification of functionally relevant genes relies mainly on differential expression analysis, thus preventing clear differentiation of causally relevant driver-genes—responsible for mechanistic activity controlling reprograming events—and passenger-genes, whose expression may change as a downstream consequence of reprogramming. Based on genome-wide maps of regulatory interactions (interactomes), network-based approaches have emerged as a valuable alternative to identify proteins acting as causal, mechanistic drivers of cell state transition events. These methodologies have been successfully applied to study functional drivers ranging from physiologic tissue reprogramming and cancer, to neurodegenerative disorders and developmental phenotypes.

In particular, the VIPER (Virtual Inference of protein activity by Enriched Regulon analysis) algorithm—an extension of the Master Regulator Inference Algorithm (MARINa)—can accurately infer the differential activity of transcriptional regulators from the differential expression of their transcriptional targets (regulons). Thus, VIPER allows systematic and unbiased prioritization of candidate Master Regulator (MR) proteins most likely to mechanistically regulate gene expression signatures associated with specific physiologic or pathologic phenotypes of interest. These algorithms were highly effective in elucidating bona fide MR proteins, whose coordinated activity is necessary and/or sufficient to induce lineage differentiation/maturation, cellular reprogramming and a variety of tumor initiation, progression, and drug-sensitivity phenotypes. Thus, a method of generating multipotent stem cells solving the aforementioned problems is desired.

SUMMARY OF THE DISCLOSURE

The method of generating multipotent stem cells is a method for producing and/or expanding multipotent stem cells by delivering at least one reprogramming protein into somatic cells using protein transduction or other suitable means. The at least one reprogramming protein includes a Master Regulator (MR) protein, such as BAZ2B, ZBTB20, ZMAT1, CNOT8, KLF12, DMTF1, HBP1, and FLI1. The bromodomain protein BAZ2B, in particular, was identified by first generating bi-species heterokaryons by fusing Tcf7l1$^{-/-}$ murine embryonic stem cells (ESCs) with human B-cell lymphocytes. Reprogramming of the B-cell nuclei to a multipotent state was tracked by human mRNA transcript profiling at multiple timepoints, from 4 hours to 5 days after fusion. Interrogation of a human B-cell regulatory network with gene expression signatures collected from such reprogramming time series identified eight candidate Master Regulator proteins, which were validated in human cord blood-derived hematopoietic progenitor and lineage-committed cells. Ectopic expression of BAZ2B, ZBTB20, ZMAT1, CNOT8 KLF12, DMTF1, HBP1, and FLI1, particularly the bromodomain family member BAZ2B, was effective in reprogramming committed progenitors into a multipotent state, thus significantly enhancing their long-term clonogenicity, stemness and long-term engraftment in immune compromised mice.

The delivery of the at least one reprogramming protein into the somatic cells may be performed using any suitable method, including but not limited to protein transduction, viral delivery using viral vectors containing a coding sequence of the Master Regulator (MR) protein or active fragments thereof, using a carrier, such as liposomes, nanoparticles, etc., containing the Master Regulator (MR) protein or mRNA, or mRNA delivery. Alternatively, usage of a compound to activate the MR protein in endogenous somatic cells may be used.

The method of identifying the Master Regulator (MR) proteins involved in onset driving events of lineage-committed cells includes the following steps:

a) obtaining bi-species heterokaryons by fusing embryonic stem cells (ESCs) of a first species with lineage-committed cells of a second species;

b) tracking reprogramming of nuclei of the lineage-committed cells to a multipotent state by transcript profiling of mRNA of the second species at multiple timepoints after fusion;

c) interrogating a regulatory network of the lineage-committed cells with gene expression signatures collected in step b) to identify candidate MR proteins; and d) validating the candidate MR proteins identified in step c) by ectopically expressing the candidate MR proteins in lineage-committed cells and progenitors thereof, and evaluating effectiveness of the candidate MR proteins in reprogramming committed lineage-committed cells and progenitors thereof into a multipotent state, thereby identifying MR proteins involved in onset driving events of the lineage-committed cells.

The interrogation in step c) may be performed using virtual inference of protein activity by enriched regulon (VIPER) analysis.

One embodiment of the present subject matter provides a method of generating multipotent stem cells, comprising the step of delivering at least one reprogramming protein into somatic cells, which may be endogenous somatic cells, wherein the at least one reprogramming protein comprises at least one Master Regulator (MR) protein.

The step of delivering at least one reprogramming protein into somatic cells may comprise protein transduction. The step of delivering at least one reprogramming protein into somatic cells may comprise viral delivery using viral vectors containing a coding sequence of the at least one MR protein or active fragments of the at least one MR protein. The step of delivering at least one reprogramming protein into somatic cells may comprise using a carrier containing the MR protein or mRNA. The step of delivering at least one reprogramming protein into somatic cells may comprise mRNA delivery.

In certain embodiments, the one or more MR proteins are selected from the following group: BAZ2B, ZBTB20, ZMAT1, CNOT8, KLF12, DMTF1, HBP1, and FLI1. In other embodiments, the one or more MR proteins comprise BAZ2B.

Other embodiments provide a method of identifying MR proteins involved in onset driving events of lineage-committed cells, comprising the steps of a) obtaining bi-species heterokaryons by fusing embryonic stem cells (ESCs) of a first species with lineage-committed cells of a second species;

b) tracking reprogramming of nuclei of the lineage-committed cells to a multipotent state by transcript profiling of mRNA of the second species at multiple timepoints after fusion;

c) interrogating a regulatory network of the lineage-committed cells with gene expression signatures collected in step b) to identify candidate MR proteins; and d) validating the candidate MR proteins identified in step c) by ectopically expressing the candidate MR proteins in lineage-committed cells and progenitors thereof, and evaluating effectiveness of the candidate MR proteins in reprogramming committed lineage-committed cells and progenitors thereof into a multipotent state, thereby identifying MR proteins involved in onset driving events of the lineage-committed cells.

In certain embodiments, step c) comprises virtual inference of protein activity by enriched regulon (VIPER) analysis.

Other embodiments provide a somatic cell ectopically expressing one or more MR proteins selected from the following group: BAZ2B, ZBTB20, ZMAT1, CNOT8, KLF12, DMTF1, HBP1, and FLI1. In other embodiments, the one or more MR proteins comprise BAZ2B.

These and other features of the present subject matter will become readily apparent upon further review of the following specification.

BRIEF DESCRIPTION OF THE DRAWINGS

FIG. 1A diagrammatically illustrates fusion of mouse embryonic stem cells with human B lymphocytes, inducing genome-wide transcriptional changes in the human nuclei, and particularly illustrating the generation of heterokaryon samples through cell-cell fusion and subsequent FACS sorting of fused cells and paired-end sequencing.

FIG. 1B is a plot showing the differential expression of human genes after fusion of murine Tcf7l1−/− ESCs with human B lymphocytes, where Log 2 fold-change of normalized counts are plotted on the x-axis and the mean of normalized counts are shown on the y-axis, and the average log count per million (CPM) values are calculated from 3 biological replicates for each time-point.

FIG. 1C schematically illustrates the generation of a protein activity profile using the VIPER algorithm and ARACNe network. The ARACNe-based human B-cell interactome consists of the information for 1241 transcription factors and their predicted downstream target genes. Differential expression profile signatures are generated for each heterokaryon sample using PEG-treated human B lymphocytes as a control. By performing VIPER Master Regulator analysis, these signatures were used to interrogate the human B-cell interactome. This gave predictions for a group of potential causal MRs along with the active or silenced protein-activity profile.

FIG. 1D is a heatmap of VIPER-predicted Normalized Enrichment Score values (NES values) of 633 TFs that had significant predicted activities (FDR<0.01) in the heterokaryon samples. NES values were calculated using the VIPER algorithm by comparing each heterokaryon sample against the unfused PEG-treated B-cells.

FIG. 3A shows the human B nuclei reprogrammed to a multipotent hematopoietic stem progenitor-like state 5 days after fusion, particularly in the form of a heatmap of predicted activity for significant hematopoietic transcription factors (TFs). The heatmap shows NES values of 445 TFs that were significant (FDR<0.01) in each sample compared to unfused B-cell samples. NES values were calculated using the VIPER algorithm, comparing the samples from each hematopoietic population against the unfused B-cells.

FIG. 3B is a set of graphs showing the correlation of transcription factor activity between heterokaryons and the human hematopoietic cells. Fisher's Exact Test (FET) was used to calculate the significance of overlap between candidate TFs whose activities were both significant (FDR<0.05) and positive in each hematopoietic population. –Log 10 of the p-values of the overlap are shown.

FIG. 3C is a heatmap showing the clustering of the TFs that were part of the early and late transcriptional programs in the Heterokaryons and in the hematopoietic cell dataset.

FIG. 3D is a heatmap showing the early MRs) in the heterokaryon and the hematopoietic cell dataset.

FIG. 3E is a heatmap showing the early MRs) in the heterokaryon and the hematopoietic cell dataset.

FIG. 6A schematically shows that BAZ2B alone is sufficient to reprogram lineage committed hematopoietic progenitors, where lineage-CD34+CD38+ committed progenitors were transduced with Luciferase or BAZ2B by Doxycycline-induced overexpression for 14 days followed by FACS analysis and sorting of Lineage-GFP+ cells for in vitro analysis.

FIG. 6B is a graph showing quantification of the CD34+ CD38− multipotent stem progenitor within Lineage-GFP+ cells from N=4 donors. Two-tailed paired t-test **P<0.01, *P<0.05.

FIG. 6C is a graph showing quantification of colonies from primary CFC assay N=3 donors. Data represented as mean±SEM. Two-tailed paired t-test **P<0.01, *P<0.05.

FIG. 6D is a graph showing quantification of colonies from LTC-IC CFC assay N=3 donors. Data represented as mean±SEM. Two-tailed paired t-test **P<0.01, *P<0.05.

FIG. 6E is a UMAP visualization of the four reference populations HSCs, MPPs, MLPs and Lineage Committed Progenitors in VIPER space.

FIG. 6F is a UMAP visualization of the top 1% of the cells from the of each of the four reference populations used for the random forest model, in the UMAP space.

FIG. 6G is a circular visualization of the model classification for Luciferase and BAZ2B samples. Samples closer to the circumference have a definite classification, and the plotting angle for each sample is determined by the weighted average of the model's classification votes.

FIG. 6H is a Venn diagram showing the number of overlapping ATAC-seq peaks in Luciferase vs BAZ2B.

FIG. 6I is a Venn diagram showing the number of overlapping ATAC-seq peaks in BAZ2B unique peaks vs Progenitors.

FIG. 6J shows the distribution of BAZ2B-induced peaks (not shared with Luciferase) from the transcription-start sites.

FIG. 6K is a heatmap for chromatin-accessible regions near the TSS.

FIG. 6L is a heatmap for unique BAZ2B-induced chromatin-accessible regions (not shared with Luciferase/progenitors).

FIG. 6M shows the transcription factors with enriched motifs in the BAZ2B-induced nucleosome-free regions.

FIG. 10A shows a human hematopoietic reference dataset used to track the reprogramming of the human B nuclei in the heterokaryons via a hierarchical model of human hematopoietic system. The samples consisted of a population of quiescent hematopoietic stem cells (HSC), which are multipotent stem cells that can differentiate into all blood cell types of the hematopoietic lineage. The HSCs after exiting quiescence form proliferating multipotent progenitor (MPP) cells that can differentiate into committed progenitors of the myeloid and the lymphoid lineages. In the lymphoid branch, the multi-lymphoid progenitors (MLP) can differentiate through as yet unknown intermediate progenitors into T lymphocytes and precursors of B lymphocytes and natural killer cell (B-NK). MLPs are not entirely committed to the lymphoid lineage and can also differentiate into monocytes from the myeloid lineage. MLP population is highly similar to HSCs and MPPs, and can differentiate into the myeloid and lymphoid lineage, with a bias toward the lymphoid lineage. In the myeloid branch, the common myeloid progenitors (CMP) are committed to the myeloid lineage and can differentiate into the myeloid progenitors of granulocytes and monocytes (GMP), megakaryocytes and erythrocytes (MEP).

FIG. 10B is a table including the surface markers that were used to sort the different hematopoietic fractions in the human hematopoietic dataset.

FIG. 10C shows a hierarchical clustering of the hematopoietic lineage data set showing significant variations between cells of the same type. Plotting was performed using the complete agglomeration method, with the expression values of the top-2000 genes with the highest variance across all the samples.

FIG. 10D shows VIPER-predicted activity of a representative set of human genes in the reference human hematopoietic stem and progenitor populations.

FIG. 10E illustrates a model of heterokaryon reprogramming, shown alongside hierarchical model of hematopoietic development.

FIG. 11A shows the overexpression of the combination of 5 transcription factors or of BAZ2B shows enhanced stemness and clonogenicity of CD34+ hematopoietic progenitors via a map of the inducible lentiviral vector used for cloning all the cDNAs.

FIG. 11B schematically shows the experimental workflow of the transduction of CD34+ hematopoietic stem and progenitor cells with Luciferase or 5-TF cocktail or BAZ2B. (C-F) CD34+ cells transduced with Luciferase or 5TF.

FIG. 11C shows representative FACS plots on day 14 for Lin-GFP+CD34+CD38− CD45RA−CD90− MPPs and Lin-GFP+CD34+CD38−CD45RA−CD90+ HSCs. Percentage fractions for each gate normalized to Lineage-GFP+ fraction represented as mean±SEM from N=5 donors.

FIG. 11D shows representative colony images of BFU-E and CFU-GM from the primary Methocult plating. Scale bar 0-1000 μm.

FIG. 11E shows representative colony images of CFU-GM from the secondary Methocult plating. Scale bar 0-1000 μm.

FIG. 11F shows representative colony images of CFU-GM from the Methocult colonies of the LTC-IC assay. Scale bar 0-1000 μm.

FIG. 11G shows the mRNA fold change of the GSEA leading edge targets of BAZ2B in the heterokaryons at 48 hours and 120 hours after fusion. Differential expression was calculated using EdgeR, and shown genes are in the leading edge and have an FDR adjusted pvalue<0.01. Boxed genes are relevant key factors discussed in the text.

FIG. 11H shows CD34+ cells transduced with Luciferase or BAZ2B via representative colony images of BFU-E and CFU-GM from the primary Methocult plating. Scale bar 0-1000 μm.

FIG. 11I shows CD34+ cells transduced with Luciferase or BAZ2B via representative colony images of BFU-E, CFU-GM and CFU-GEMM from the secondary Methocult plating. Scale bar 0-1000 μm.

FIG. 11J shows CD34+ cells transduced with Luciferase or BAZ2B via representative colony images of BFU-E, CFU-GM and CFU-GEMM from the long-term culture-initiating cell (LTC-IC) assay. Scale bar 0-1000.

Figures 12A, 12B, 12C, 12D, 12E, 12F:
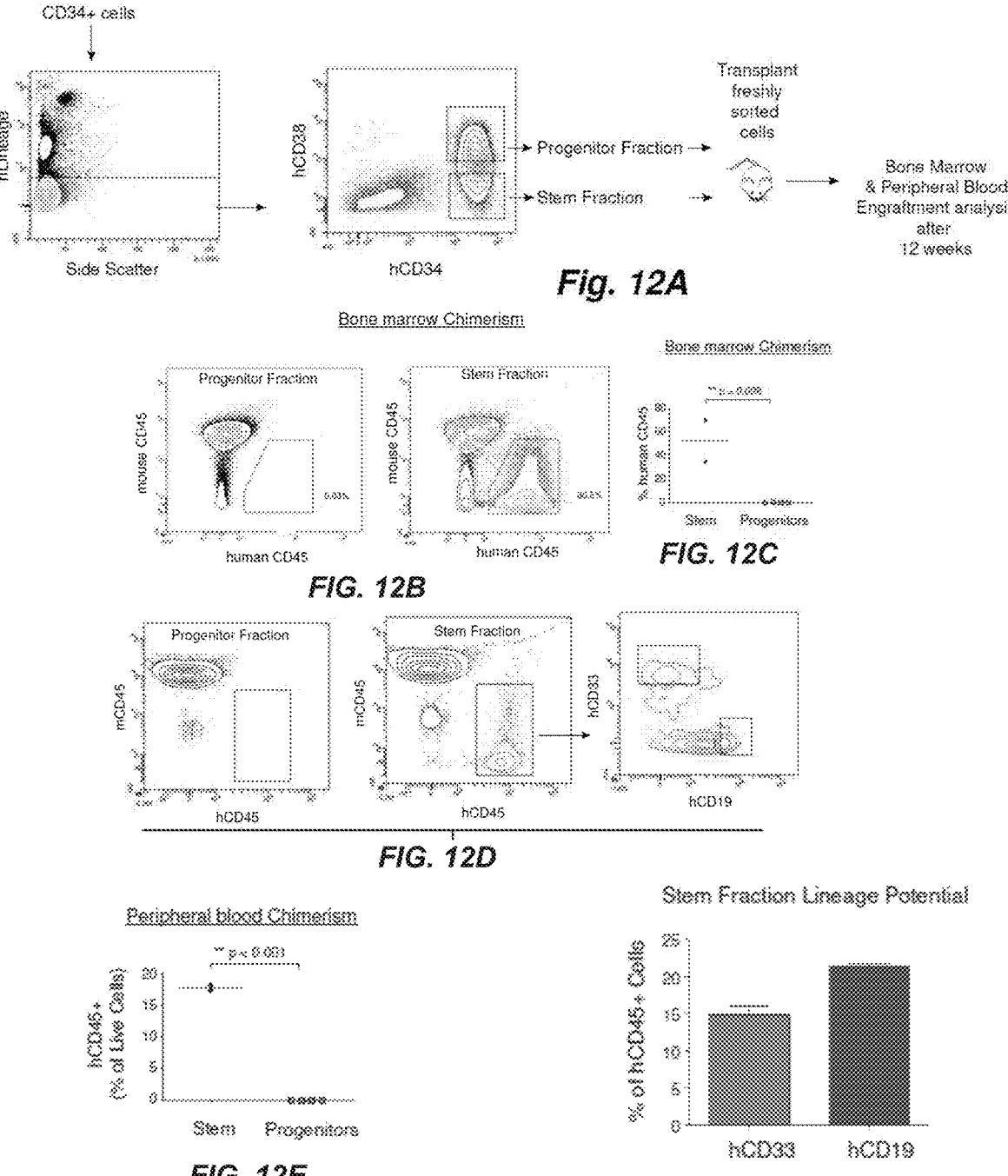

FIG. 12A shows the long-term engraftment potential of uncultured stem and progenitor fractions via a schematic diagram showing sorting and transplantation of uncultured Lin-CD34+CD38− stem fraction and the Lin-CD34+CD38+ progenitor fraction.

FIG. 12B shows representative FACS plot for bone marrow chimerism.

FIG. 12C is a plot showing quantification of the percentage of human CD45 positive cells in the bone marrow of all transplanted mice.

FIG. 12D shows representative FACS plots showing human chimerism in the peripheral blood indicating the CD33-myeloid and CD19-lymphoid potential.

FIG. 12E is a plot showing quantification of the peripheral blood chimerism based on the fraction of human CD45+ cells within the live cells.

FIG. 12F shows lineage potential with respect to the total engrafted human CD45+ cells in the mice transplanted with the Lin-CD34+CD38− stem fraction.

Figures 12G, 12H:
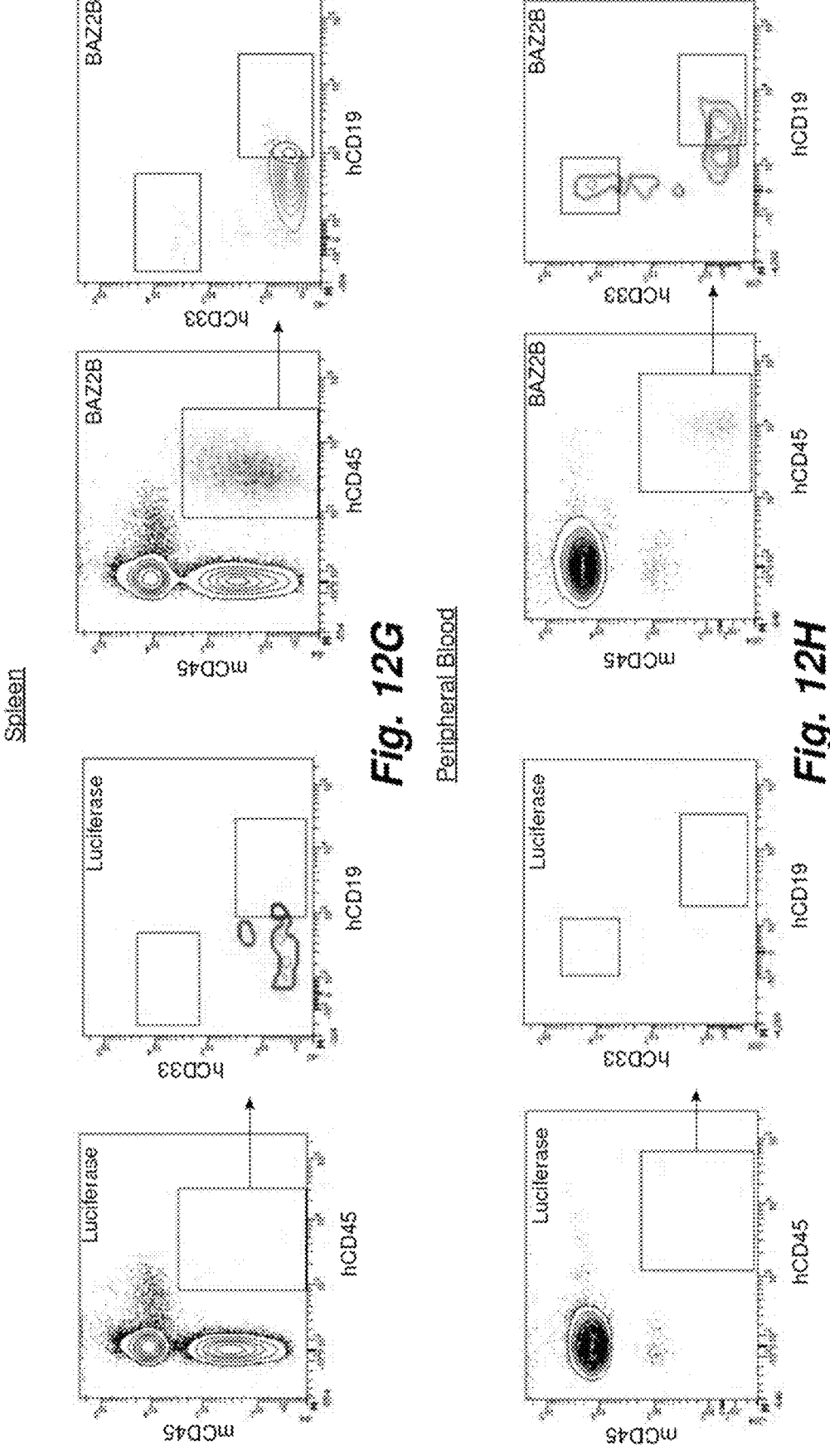

FIG. 12G shows representative FACS plots showing human chimerism in the spleen.

FIG. 12H shows representative FACS plots showing human chimerism in peripheral blood, indicating the CD33-myeloid and CD19-lymphoid potential.

Figures 13A, 13B, 13C, 13D, 13E, 13F, 13G:
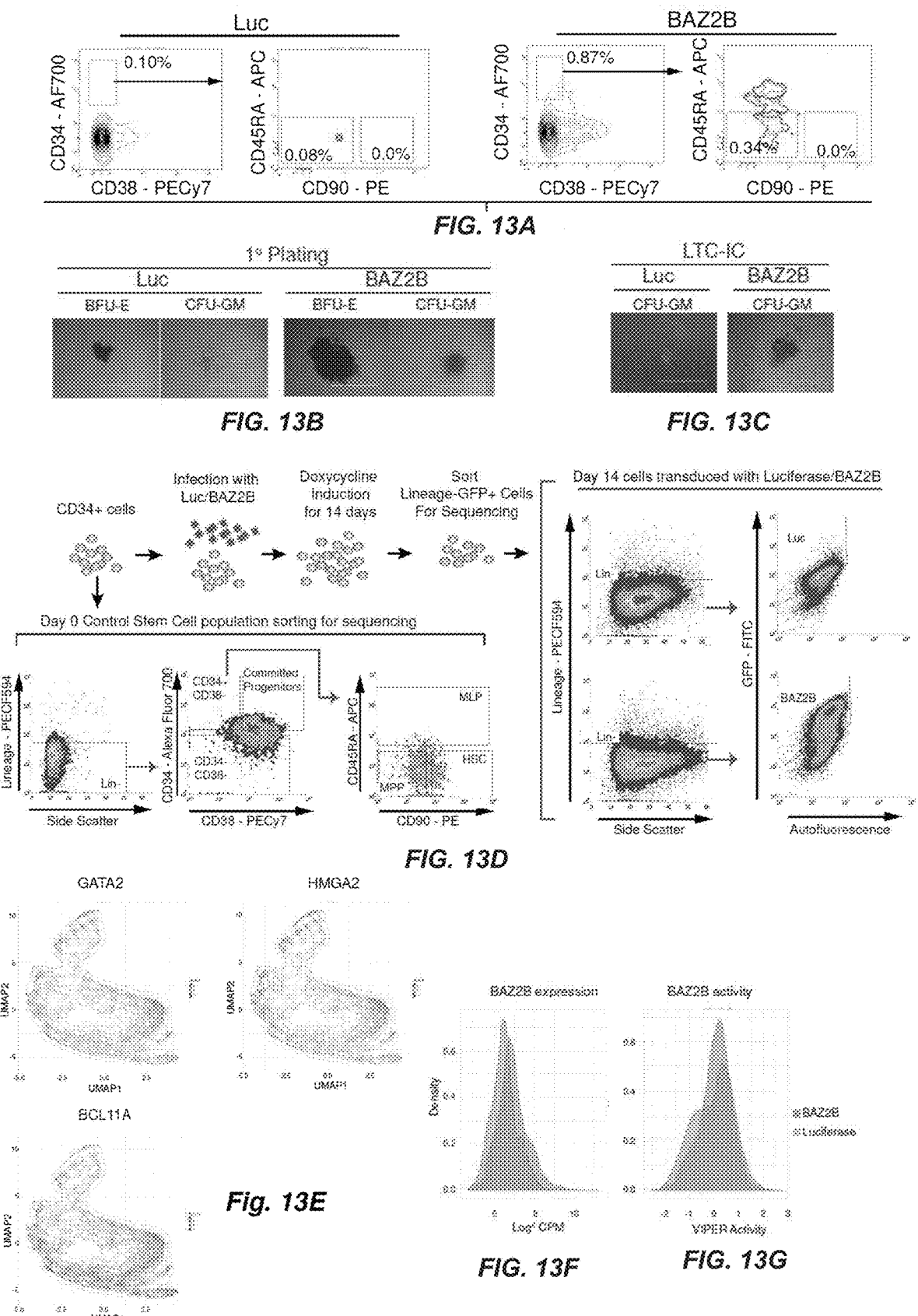

FIG. 13A shows single-cell sequencing of HSCs, MPPs, MLPs, and Lineage committed Progenitors and BAZ2B-induced renewal of Lineage-CD34+CD38− stem fraction via a representative FACS plot on day 14 showing the progenitor Lin-GFP+CD34+CD38−, MPP Lin-GFP+CD34+CD38−CD45RA−CD90− and HSC Lin-GFP+CD34+CD38−CD45RA− CD90+. Percentage fractions for each gate normalized to Lineage-GFP+ fraction represented as mean±SEM from N=5 donors.

FIG. 13B shows representative colony images of BFU-E and CFU-GM from the primary Methocult plating. Scale bar 0-1000 μm.

FIG. 13C shows representative colony images of BFU-E, CFU-GEMM and CFU-GM from the LTC-IC Methocult plating. Scale bar 0-1000 μm.

FIG. 13D, on the top left, shows an experimental schematic of the single-cell sequencing experiment; on the bottom left shows FACS plots showing control cell populations sorted on day 0 for sequencing: HSC (Lin-CD34+CD38−CD45RA−CD90+), MPP (Lin-CD34+CD38−CD45RA−CD90−), MLP (Lin-CD34+CD38−CD45RA+) enriched population, and Lineage committed Progenitors (Lin-CD34+CD38+); and on the right shows FACS plots showing the CD34+ cells transduced with Luciferase and BAZ2B for 14 days. Lineage-GFP+ cells were sorted for single-cell sequencing.

FIG. 13E is a UMAP plot showing VIPER activity of transcription factor markers in reference single-cell populations, including HSCs, MPPs, MLPs, and Lineage committed progenitors.

FIG. 13F shows lineage-committed progenitors transduced with Luciferase/BAZ2B for mRNA expression of BAZ2B.

FIG. 13G shows lineage-committed progenitors transduced with Luciferase/BAZ2B for VIPER-predicted activity of BAZ2B.

FIG. 14A shows BAZ2B-induced reprogramming of committed progenitors to multipotent hematopoietic progenitors via an individual donor heatmap of chromatin-accessible regions near the TSS.

FIG. 14B shows BAZ2B-induced reprogramming of committed progenitors to multipotent hematopoietic progenitors via an individual donor heatmap of chromatin-accessible regions uniquely induced by BAZ2B in distal enhancer regions.

FIG. 14C is a Venn diagram showing the distal enhancer regions of FIG. 14B.

FIG. 14D shows representative FACS plots showing human chimerism in the spleen.

FIG. 14E shows representative FACS plots showing human chimerism in peripheral blood.

FIG. 15 includes Table 1, showing MRs ranked by statistical significance.

FIG. 16 includes Table 2, showing the number of reads that mapped to either the human (hg19) or mouse (mm10) genomes according to the TopHat method. For each sample, the table shows the total number of mapped reads, the number of reads that mapped uniquely to the human and mouse genomes and multi-mapping reads that mapped to both genomes.

FIG. 17 includes Table 3, showing the number of reads that mapped to either the human (hg19) or mouse (mm10) genomes after multi-mapping reads were assigned to either the mouse or human genome using the "fair-split" method. For each sample, the table shows the total number of mapped reads, the final number of reads that mapped to the human and mouse genome after correction.

FIG. 18 includes Table 4, showing the number of genes that had greater than 1 read assigned to it (out of 22,932 total annotated genes in the human genome).

FIG. 19 includes Table 5, showing the number of genes that had greater than 1 read assigned to it (out of 23,079 total annotated genes in the mouse genome).

FIG. 20 includes Table 6, showing the number of Master Regulators (MRs) that were predicted in each timepoint (FDR<0.01).

Figure 21B:
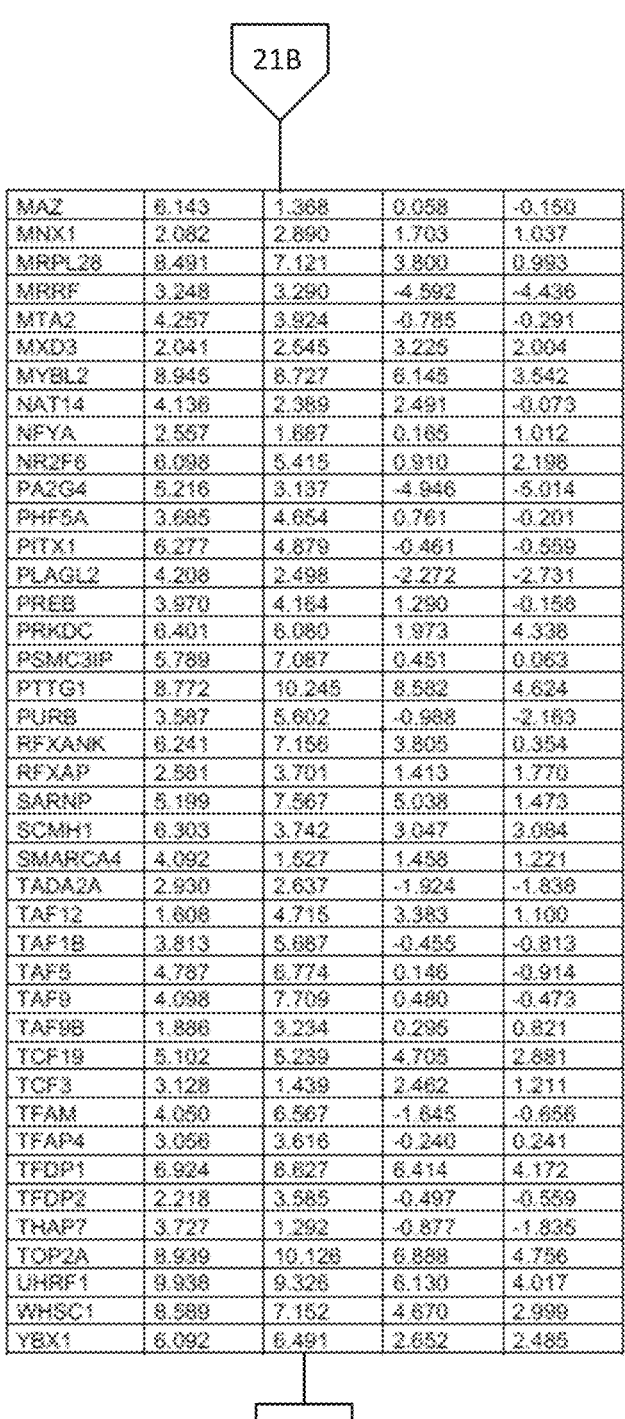
Figure 21C:
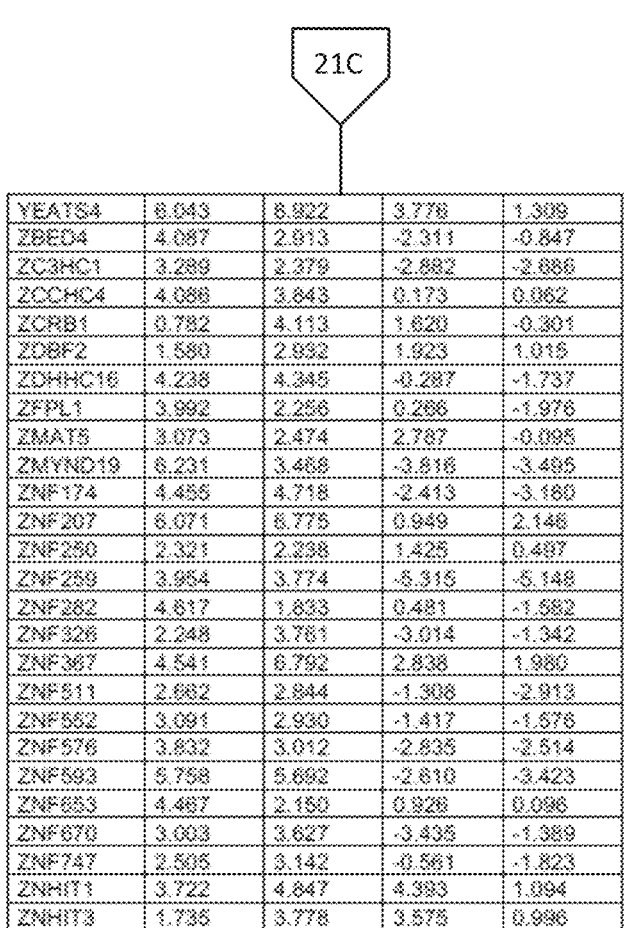

FIG. 21A, FIG. 21B and FIG. 21C include Table 7, showing 105 TFs that were significantly associated (P-val<0.05) with Principal Component 1.

Figure 22A:
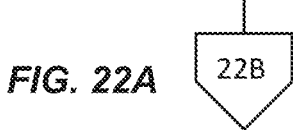
Figure 22B:
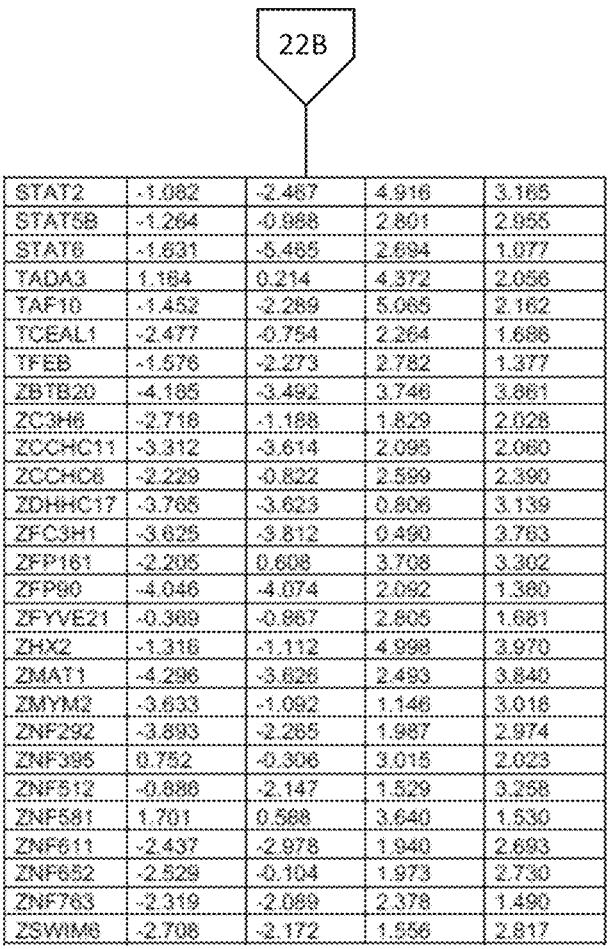

FIG. 22A and FIG. 22B include Table 8, showing 64 TFs that were significantly associated (P-val<0.05) with Principal Component 2.

FIG. 23 includes Table 9, showing the genes that were identified as classifiers by the random forest model to distinguish HSCs, MPPs, MLPs and the committed progenitors.

Figure 24B:
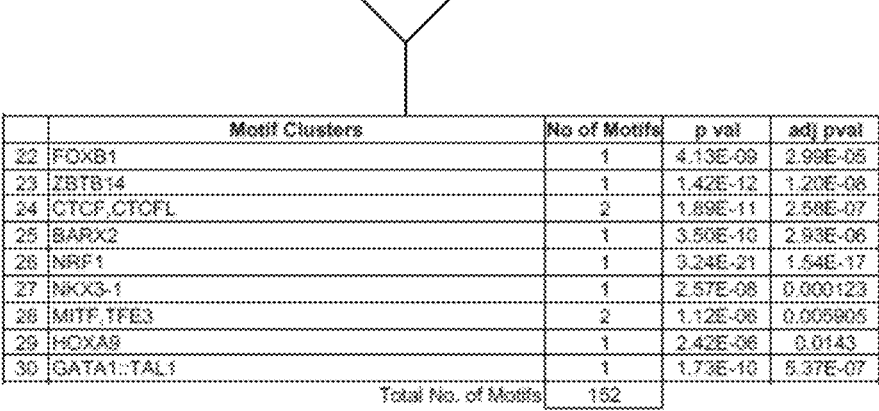

FIG. 24A and FIG. 24B include Table 10, showing the RSAT clustering of enriched motifs with the average p-values of motif enrichment within each cluster. p-values for individual motif enrichment were first calculated using AME. RSAT was then used to cluster the motifs based on consensus sequences, and the average of individual p-values for motifs within each group were calculated.

Figure 25B:
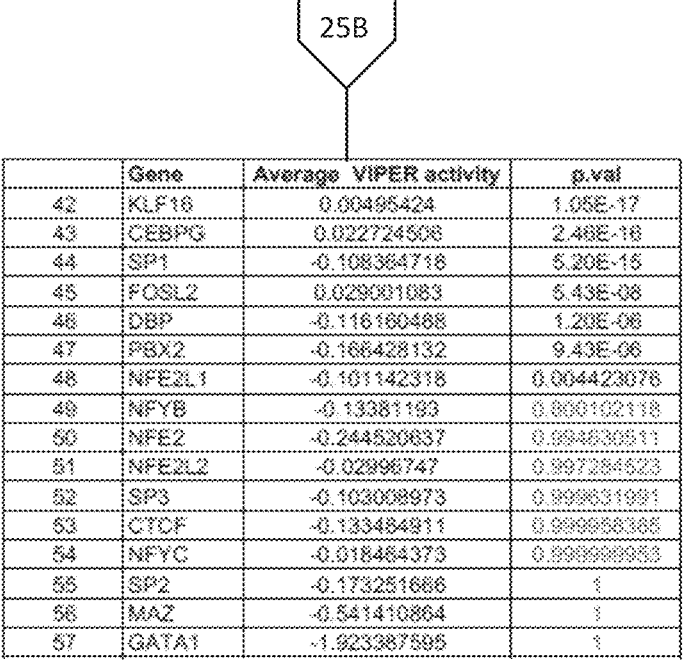

FIG. 25A and FIG. 25B include Table 11, showing VIPER predicted activities for TFs with enriched binding motifs in BAZ2B induced nucleosome-free regions.

Similar reference characters denote corresponding features consistently throughout the attached drawings.

EXEMPLARY EMBODIMENTS

To elucidate early drivers of B-cell reprogramming, we fused murine Tcf7l1$^{-/-}$ ESCs with human B-cells and isolated the resulting bi-species heterokaryons soon after fusion. Tcf7l1—a key effector of the Wnt pathway—plays a crucial role in ESC renewal and pluripotency maintenance. Consistently, previous work has shown that fusion of Tcf7l1$^{-/-}$ ESCs with somatic cells significantly enhances the efficiency of reprogramming of the somatic nucleus to pluripotency, compared to Tcf7l1$^{WT}$ ESCs. This suggests that heterokaryons derived from Tcf7l1$^{-/-}$ ESCs represent an ideal cellular context to study processes associated with reprogramming initiation.

Rather than focusing on differentially expressed genes, we performed VIPER analysis to identify MR proteins that causally regulate the transcriptional signature of the reprogramming event, via direct activation and repression of their transcriptional targets. We thus leveraged a human B cell-specific regulatory network (BCRN) to perform VIPER analysis of gene expression signatures representing different timepoints of human B-cell reprogramming in the heterokaryons. The BCRN includes the activated and repressed transcriptional targets of each regulatory protein, as reverse engineered de novo by the ARACNe algorithm (Accurate Reconstruction of Accurate Cellular Networks).

VIPER analysis showed that the repertoire of proteins representing established lineage determinants of mature B-cells was rapidly inactivated, within 4 h-12 h after heterokaryon isolation. Interestingly, in contrast to current belief, robust activation of embryonic stem cell pluripotency-related drivers could not be detected until 5 days following fusion. Rather, the majority of transcription factors activated up to that point were related to the hematopoietic progenitors and hematopoietic stem cells. Specifically, VIPER identified two distinct MR sets—representing an "early" and a "late" regulatory program, respectively—that were sequentially activated during somatic B-cell reprogramming. Consistently, we first observed VIPER-inferred activation of "early" MRs enriched in markers of lineage-committed hematopoietic progenitors, whose activity was then switched off and replaced by MRs associated with a hematopoietic stem/multipotent progenitor-like state. Based on these analyses we identified 8 MRs of "late" reprogramming (then refined to 5), as most likely drivers of committed progenitor reprogramming to a multipotent state. These were experimentally tested for their ability first to enhance stemness and clonogenicity of human cord blood-derived CD34+ cells and then to reprogram committed hematopoietic progenitor cells. Finally, ectopic expression of a single one of these five genes (i.e., BAZ2B), significantly enhanced reprogramming, long-term clonogenicity, and stemness of human hematopoietic committed progenitors, as demonstrated by single-cell sequencing assays. BAZ2B remodels chromatin of proximal and distal enhancers and BAZ2B-reprogrammed committed progenitors, in the hematopoietic lineage, could efficiently repopulate the bone marrow of immunocompromised mice after long term engraftment. These results confirm BAZ2B's ability to mechanistically control the reprogramming signature of human hematopoietic cells and suggest that the proposed approach is effective in prioritizing key functional drivers of cell state reprogramming events.

Figures 8A, 8B, 8C:
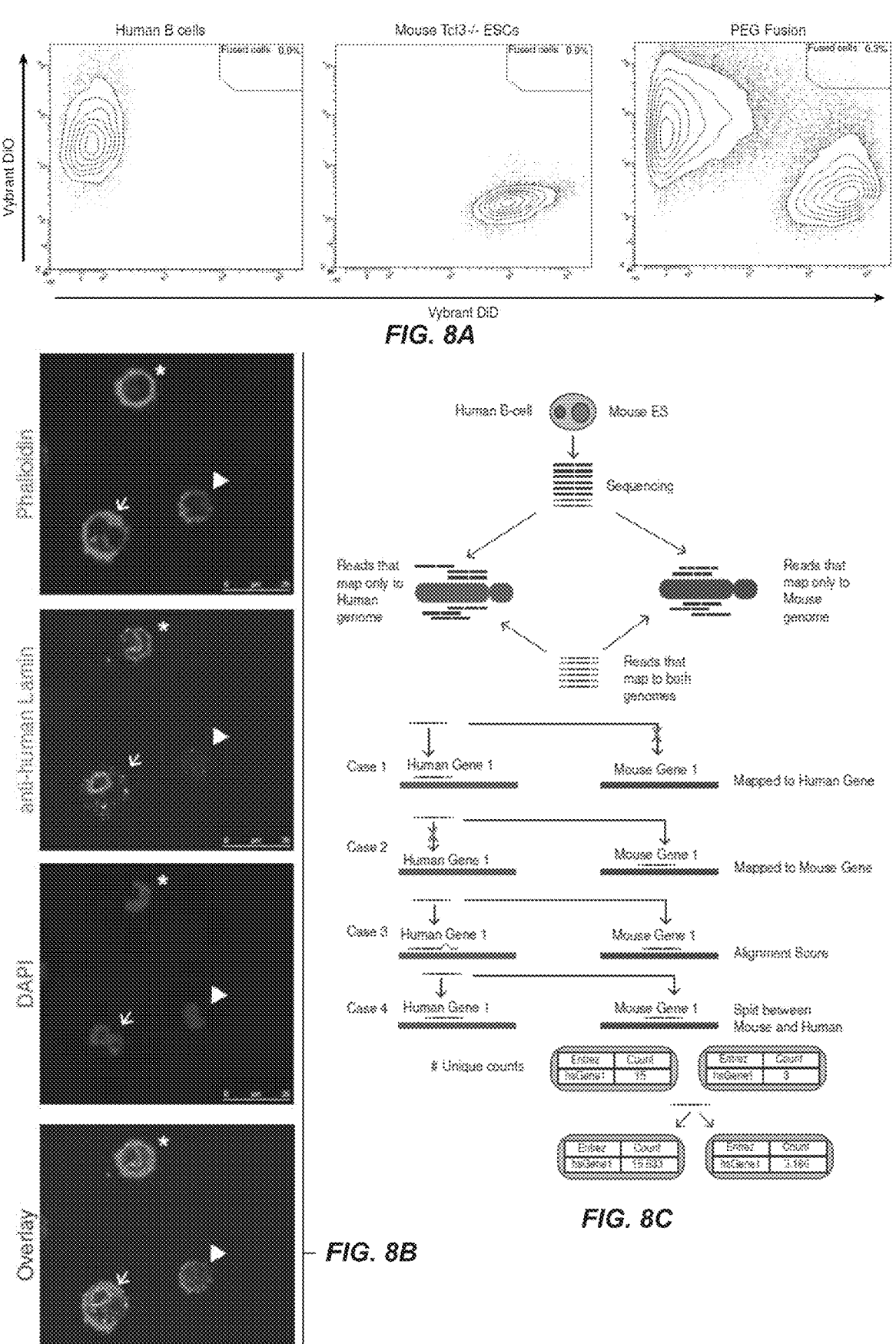
FIG. 8A shows mRNA sequence read mapping of bi-species heterokaryons sorted by flow cytometry, in the form of human B-cells labeled with Vybrant® DiO and Mouse Tcf7l1−/− ESCs labeled with Vybrant® DiD, with representative FACS plot of cells sorted 4 hours after PEG fusion.
FIG. 8B is a set of images showing immunostaining of human B-cells fused with mouse Tcf7l1−/− ESCs and sorted 4 hours after fusion. One representative picture area was chosen to show unfused and hybrid cells. Phalloidin stains the actin filaments. Anti-human Lamin stains the B-cell nuclear membrane. DAPI stains the nucleus. The asterisk (*) points to a human B-cell, the triangle (∇) points to a mouse ESC and the arrow (←) points to a heterokaryon. Scale bar 0-25 μm.
FIG. 8C schematically illustrates the mapping of the mouse and human reads. First, the reads were mapped to the mouse and human genomes with high stringency. Multi-mapping reads were assigned to either the mouse or human genome using known gene information. If a read mapped to a gene in one of the genomes, but non-gene region in the other, the reads were assigned to the appropriate gene. Next, mapping quality was considered to assign the read to the genome with the higher quality mapping. Finally, the reads that mapped perfectly to genes in both genomes were split between each of the genomes by considering how many unique reads had been already mapped to each gene.

To identify novel MRs that drive initiation of reprogramming, we analyzed the transcriptional profile of the somatic nucleus at several time-points following fusion. To distinguish the transcriptome of somatic nuclei from ESC nuclei, we fused murine Tcf7l1$^{-/-}$ ESCs with Epstein Barr Virus-immortalized human B-lymphocytes (B-cells), thus yielding bi-species heterokaryons. The ESCs and the B-cells were labeled with red and green lipophilic fluorochrome dyes (DiD and DiO), respectively. The stained cells were then fused in vitro using polyethylene glycol (PEG) and the hybrid cells were FACS-sorted and processed for RNA extraction at different time-points after fusion (see FIG. 1A, Supplementary FIGS. 8A and 8B). We performed paired-end RNA sequencing in order to obtain the global gene expression profiles of the heterokaryons at a high resolution (see FIG. 8C and Tables 2 and 3 of FIGS. 16 and 17, respectively). Sequencing reads were mapped to the mouse or human genome, as described in the schematic charts (FIG. 8C and Tables 2-5 of FIGS. 16-19, respectively), such that human somatic cell reprogramming could be effectively tracked.

Figures 9A, 9B, 9C, 9D:
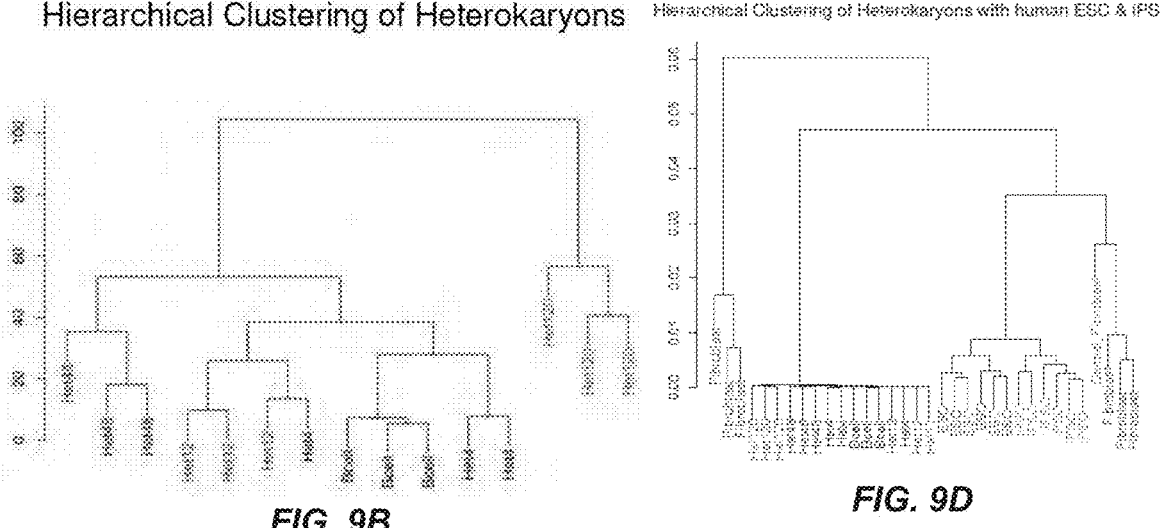
FIG. 9A shows the consistency of human gene expression in the heterokaryon sample replicates via comparison of replicates for human gene expression during cell-fusion mediated reprogramming over 5 days. Spearman correlation between each sample is shown. Sample numbers are shown on the x and y axis, and the plots show the correlation shown for samples 4 hours after fusion, 12 hours after fusion, 48 hours after fusion and 120 hours after fusion.
FIG. 9B shows a hierarchical clustering of heterokaryons samples, showing strong separation according to time-points. Results show that almost all the sample replicates separated according to their respective time-points after cell fusion. Plotting was performed using the complete agglomeration method using the expression values of the top-2000 genes with the highest variance across all the samples.
FIG. 9C is a set of graphs showing expression of a representative set of human pluripotency markers in the heterokaryon samples during reprogramming. Results show the raw count of POU5F1, NANOG, and KLF4 normalized to GAPDH, prior to fusion (B-cell) and 4 h, 12 h, 48 h, and 120 h, after cell fusion.
FIG. 9D shows a hierarchical clustering performed between heterokaryon samples, fibroblasts and iPSC samples from a reference dataset (GSE41716). Results show a strong separation between heterokaryon samples and both the fibroblast and iPSC samples, suggesting a significant difference in the gene expression patterns. Plotting was performed using the complete agglomeration method using the expression values of the top-2000 genes with the highest variance across all samples.

Replicates showed high reproducibility based on Spearman correlation ($\rho > 0.90$, for all comparisons), as shown in FIG. 9A. Hierarchical clustering of the global gene expression levels showed that almost all of the sample replicates separated according to their respective time-points after cell fusion (see FIG. 9B).

Differential expression analyses of the human transcriptome showed that significant changes in gene expression occur globally in the human genome very early after cell fusion (FIG. 1B, upper panel). Interestingly, a similar analysis of the mouse transcriptome showed very few differentially expressed genes between the different time-points in the heterokaryons (FIG. 1B, lower panel). This shows that the murine ESC nucleus is dominant in the heterokaryons and significantly reprograms the transcriptional state of human somatic cells. This is consistent with previous studies that reported a dominant nature of the ESCs in the transcriptional regulation of ES-somatic cell hybrids. Five days after fusion, the mRNA expression of human pluripotency markers such as NANOG, POU5F1 and KLF4 were upregulated in the heterokaryons, compared to the unfused human B-cells (FIG. 9C), consistent with previous results. Altogether, these data confirmed that cell-fusion with murine Tcf7l1$^{-/-}$ ESCs had induced reprogramming of human B-cells toward an embryonic stem cell state, albeit with low reprogramming efficiency.

In order to identify transcription factor (TF) proteins whose activity plays a mechanistic role in the reprogramming of human B-cell nuclei, the BCRN interactome was interrogated with human gene expression signatures, representing differentially expressed genes at multiple time points following heterokaryon isolation, using the VIPER algorithm (FIG. 1C). To assess their role as candidate mechanistic determinants of cell reprogramming, VIPER computes the enrichment of the transcriptional targets of each TF in differentially expressed genes, based on the BCRN interactome. To improve prediction quality, VIPER also accounts for whether targets are activated or repressed by the TF, for the regulator-target gene interaction confidence, and for the pleiotropic nature of target-gene regulation (i.e., targets being regulated by multiple TFs).

For this study, we first assembled the BCRN by integrating two previously published datasets that were originally generated by ARACNe analysis of a large collection of normal and tumor related gene expression profiles, representing normal B-cells undergoing germinal-center reaction, as well from as a variety of germinal center lymphomas from patient biopsies and cell lines. Critically, ARACNe analysis of these datasets has been extensively validated as being highly enriched (>70%) in direct, physical regulatory interactions between regulatory proteins and transcriptional targets.

VIPER-based analysis of heterokaryon time-series signatures helped identify candidate transcription factors that were causally related to early events following cell fusion, on a sample-by-sample basis. Specifically, for each sampled time point, VIPER analysis was performed on the differential gene expression signature obtained by comparing the expression of each heterokaryon sample with the average expression of unfused B-cell samples as controls (non-reprogrammed state), by Student t-test analysis. The analysis identified 633 TFs that, based on differential expression of their transcriptional targets, were significantly differentially activated in at least one sample (FDR<0.01) (FIG. 1D and Table 6 of FIG. 20), suggesting a causal role in establishing the transcriptional state of the reprogrammed B-cell nuclei at the corresponding time points.

Figures 2A, 2B, 2C, 2D, 2E, 2F:
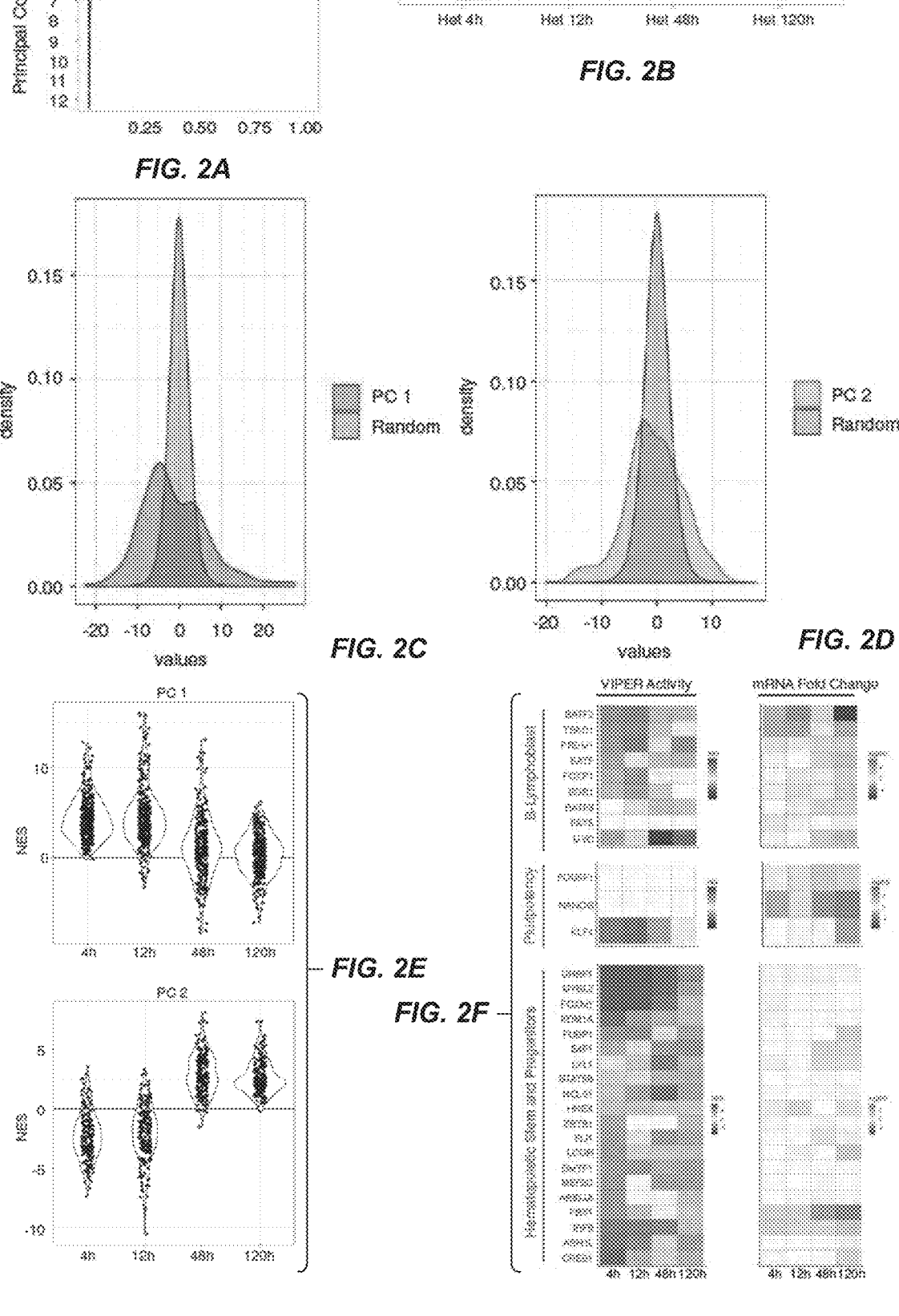
FIG. 2A illustrates two distinct clusters of transcription factors that are sequentially activated in a time-dependent manner in the human B nuclei in the heterokaryons, particularly in the form of a plot showing the total variance of VIPER activity in the heterokaryon dataset explained by each Principal Component (PC) after Single Value Decomposition (SVD) analysis. PCs are plotted on the y-axis and the proportion of variance is plotted on the x-axis.
FIG. 2B is a plot showing the PC levels across the sample time points for the top-2 PCs of the heterokaryon dataset.
FIG. 2C and FIG. 2D are graphs showing genes that contributed significantly to the PCs 1 and 2 determined by comparing the PC coefficients with PC coefficients calculated from randomly shuffled VIPER activity levels. The analysis resulted in 105 transcription factors that were significantly (p<0.05) associated with PC 1 and 65 transcription factors that were significantly associated with PC 2.
FIG. 2E shows violin plots for VIPER-predicted activity levels in the upper panel for the 105 transcription factors significantly (p<0.05) associated with PC 1, and in the lower panel for 65 transcription factors significantly associated with PC 2. VIPER-predicted activity is represented by average Normalized Enrichment Sores (NES), and were calculated using the VIPER algorithm, comparing the heterokaryon samples of each time point (either 4 h, 12 h, 48 h, 120 h) against the unfused B-cells.
FIG. 2F shows VIPER-predicted activity and differential expression of a representative set of human genes during reprogramming. mRNA Fold Change (Log 2FC) was calculated using EdgeR by comparing the heterokaryon samples with unfused B-cells.

To further identify TFs representing critical determinants of the specific temporal pattern observed during reprogramming, thus achieving deeper insight into the cascade of molecular events leading to B-cell reprogramming, we used the singular value decomposition (SVD) method. SVD is an established dimensionality reduction technique, which can be used to estimate the most orthogonal TF contributions to a transcriptional program. From the original VIPER-inferred TF-activity matrix, the activity of 633 TFs across 12 heterokaryon samples, representing 4 time points (4 h, 12 h, 48 h and 120 h) in triplicate was summarized. SVD analysis identified 12 principal components (eigengenes), representing orthogonal linear combinations of weighted TF activities, with weights proportional to the TF contribution that are regulating the transcriptional program (FIG. 2A). Critically, we observed that only two principal components were necessary to account for most of the total data variance (~85%), as shown in FIG. 9A. When these principal components were plotted across all available time points, they showed unique and opposite, time-dependent TF activity patterns during heterokaryon reprogramming (FIG. 2B).

Based on the first two principal components we could broadly classify relevant TFs into 2 distinct clusters—one associated with TFs activated from 0 h to 12 h (early) and one associated with TFs activated after 12 h (late). Key TFs were identified as those with coefficients corresponding to a statistically significant p-value (p≤0.05) based on a null model assembled by sample shuffling (FIG. 2C). Based on this analysis, we identified 105 TFs significantly associated with the first principal component (early reprogramming events) (FIG. 2D, top panel, and Table 7 of FIGS. 21A-21C) and 65 TFs significantly associated with the second one (late reprogramming events) (FIG. 2D, bottom panel, and Table 8 of FIGS. 22A and 22B). These results suggest the existence of two distinct, complementary, and highly coordinated programs controlling reprogramming of the somatic human genome following heterokaryon formation.

We first analyzed whether these two TF programs included established B-cell related lineage markers (BATF2, TEAD1, PRDM1, BATF, FOXP1, EGR1, BATF3, PAX5), known to maintain B-cell commitment and differentiation, B-cell activation, and B-cell survival. Interestingly VIPER analysis showed rapid inactivation of these factors after cell-cell fusion (FIG. 2E), suggesting that transcriptional programs associated with B-cell identity are indeed inactivated soon after cell fusion.

EBV-mediated immortalization and proliferation of the human B-cells to generate the lymphoblast cell line is driven by the oncogene MYC. Indeed, we observed a mild VIPER-predicted activity of MYC (FDR=0.038) mainly 4 hours after fusion in the heterokaryons. However, at the late time points of 48 hours and 5 days after fusion, the VIPER-predicted activity of MYC was significantly decreased (FDR<0.01), as shown in FIG. 2E. This suggests that the gene program associated with EBV-immortalization is effectively silenced at the late stages of reprogramming, after fusion.

We then assessed the reactivation of pluripotency markers to determine if human B-cell nuclei had been reprogrammed to a pluripotent state. The mRNA expression levels of pluripotency genes, such as POU5F1, NANOG and KLF4, were significantly up regulated (adjusted p-value<0.05) at later time-points (FIG. 2E). Yet, based on VIPER-inferred activity, these pluripotency markers were inactive until 5 days after fusion.

To further investigate possible reprogramming toward an embryonic stem state, we performed genome-wide comparison of heterokaryon gene expression profiles with those of human induced Pluripotent Stem Cells (iPSC) and human ESCs. This analysis did not show significant similarity between these datasets (FIG. 9D), suggesting that even five days after fusion, the reprogramming state of heterokaryons is different from human ESCs and iPSCs.

Finally, we assessed the TFs whose activity was significantly upregulated at 48 h and 120 h after cell fusion by literature analysis (FIG. 2E). We observed that TFs such as UHRF1, MYBL2, FOXM1 and KDM1A, shown to regulate hematopoietic stem and progenitor cell function, were significantly activated at the early time points. Interestingly, we also found among others a number of TFs such as LYL1, DMTF1 and ASH1L known to play a key role in hematopoietic stem cell (HSC) maintenance, quiescence, and survival, which were exclusively activated at the late time points at 48 h and 120 h. Taken together, these data suggest that, upon fusion with mouse Tcf7l1$^{-/-}$ ESCs, human B-cell nuclei may be reprogrammed toward an HSC-like state.

To determine the transcriptional identity of the human nuclei within heterokaryons, we compared the human transcriptome of these cells with those of a publicly available human hematopoietic lineage dataset (FIG. 10A, 10B). We first performed hierarchical clustering of all published hematopoietic lineage samples, based on their gene expression profiles (FIG. 10C). Two major clusters were identified, one including stem-like cells (HSCs, MPPs and MLPs), and one representing lineage-committed cells (CMPs, GMPs and MEPs) (see FIG. 10B for non-abbreviated names). Several samples showed significant cross-replicate variability (FIG. 10C), possibly due to variability between individual cord blood donors and the intrinsic heterogeneity of cell populations.

We then clustered the same profiles after VIPER-based inference of TF activity on a sample-by-sample basis. Similar to the heterokaryons, VIPER analysis was performed on differential gene expression signatures obtained by comparing each sample with a set of physiologic (i.e., unfused) B-cells, as control. The analysis identified 445 TFs with statistically significant differential activity in at least one sample (FDR<0.01) (FIG. 3A). Interestingly, TF activity in the hematopoietic lineage also showed a bimodal pattern, reminiscent of the early and late transcription program in the heterokaryons (FIGS. 1D and 2B), with "stem-cell" related TFs active in HSC, MPP, and MLP cells and then inactivated in committed progenitors (CMP, GMP, and MEP), where they were replaced by a second wave of activated TFs (FIG. 3A). Of note, consistent with previous data, the MLP expression profile is similar to that of HSCs and MPPs. Overall, VIPER-inferred TFs showed activity profiles comparable to the gene expression profiles previously reported for both hematopoietic stem and committed progenitors.

We confirmed that the VIPER-inferred activity of TFs in the HSC and the lineage-committed progenitor fractions correlated with the physiological function of some previously validated TFs. As an example, the transcription factors MYBL2 and E4F1 were significantly activated in the myeloid progenitor population (FIG. 10D), consistent with physiological validation assays in knockout mouse studies where depletion of Mybl2 or E4f1 led to myeloid progenitor cell apoptosis. The HHEX transcription factor had the highest activity in the lymphoid MLP fraction (FIG. 10D). This prediction is consistent with knockout studies of mouse hematopoietic stem and progenitor cells demonstrating that HHEX is necessary for lymphoid lineage specification. Interestingly, we also observed that LCOR was significantly activated in HSC, MPP and MLP populations, in agreement with its recently reported role in inducing the reprogramming of hemogenic endothelium cells into hematopoietic stem and progenitor cells. ASH1L and FUBP1 were significantly activated in HSC and MPP populations (FIG. 10D), consistent with mouse studies showing that depletion of either Ash1l or Fubp1 severely affects HSC self-renewal potential. These observations demonstrate that VIPER analysis, using the B-cell interactome, is effective in recapitulating a key subset of physiologically relevant MR proteins in the hematopoietic system.

We further investigated whether the two distinct TF clusters identified by VIPER analysis of hematopoietic lineage cells were consistent with the "early" and "late" transcriptional programs identified from the heterokaryons (FIGS. 1D and 2B). Specifically, we assessed the statistical significance of the overlap of these programs by Fisher's Exact Test (FET) analysis of TFs with statistically significant differential VIPER activity (FDR<0.05) and a positive enrichment score in both datasets (FIG. 3B). This analysis showed that the TF activity profiles of early heterokaryons (4 h and 12 h after fusion) significantly overlapped with those generated from lineage-committed progenitors, which comprise myeloid progenitors (GMP, MEP, CMP) (FIG. 3B) (p<1e-5, by FET). Conversely, TF activity profiles of late heterokaryons (120 h after fusion) significantly overlapped with those generated from stem and multipotent-progenitors (HSC, MPP and MLPs) (FIG. 3B) (p<1e-5, by FET), while heterokaryons at 48 h after fusion, showed a significant overlap with all populations (p<1e-5 by FET).

We then focused on TFs, whose differential activity was significant (FDR<0.01) in both heterokaryon and hematopoietic lineage cells (FIG. 3C). This identified 16 TFs with similar VIPER-inferred activity in early heterokaryons and in lineage committed progenitors (FIGS. 3C and 3D) and 26 TFs with similar activity in late heterokaryons and stem/multipotent progenitors (FIGS. 3C and 3E). Critically, these two TF sets were included in the TFs significantly associated with the first and second principal components, respectively (FIG. 2A and Tables 7 and 8 of FIGS. 21A-21C and 22A-22B, respectively), suggesting a causal role in implementing the transcriptional programs associated with B-cell reprogramming.

Specifically, taken together, these data suggest that, following fusion, human B-cell nuclei are first (4 h/12 h) reprogrammed to a state most resembling that of a proliferative, lineage-committed progenitor (FIG. 10E), which is mechanistically regulated by the concerted activity of a first wave of activated TFs (Early-MRs). Following this initial transition, human nuclei are then further reprogrammed toward a hematopoietic/multipotent state (48 h/120 h) by a second wave of activated TFs (Late-MRs). Further supporting this hypothesis, several of the TFs identified by our analysis, such as FOXM1, MYBL2, DMTF1 and ASH1L have been previously shown to play a role in hematopoietic stem and progenitor maintenance.

Figures 4A, 4B, 4C, 4D, 4E, 4F, 4G, 4H, 4I, 4J, 4K, 4L, 4M:
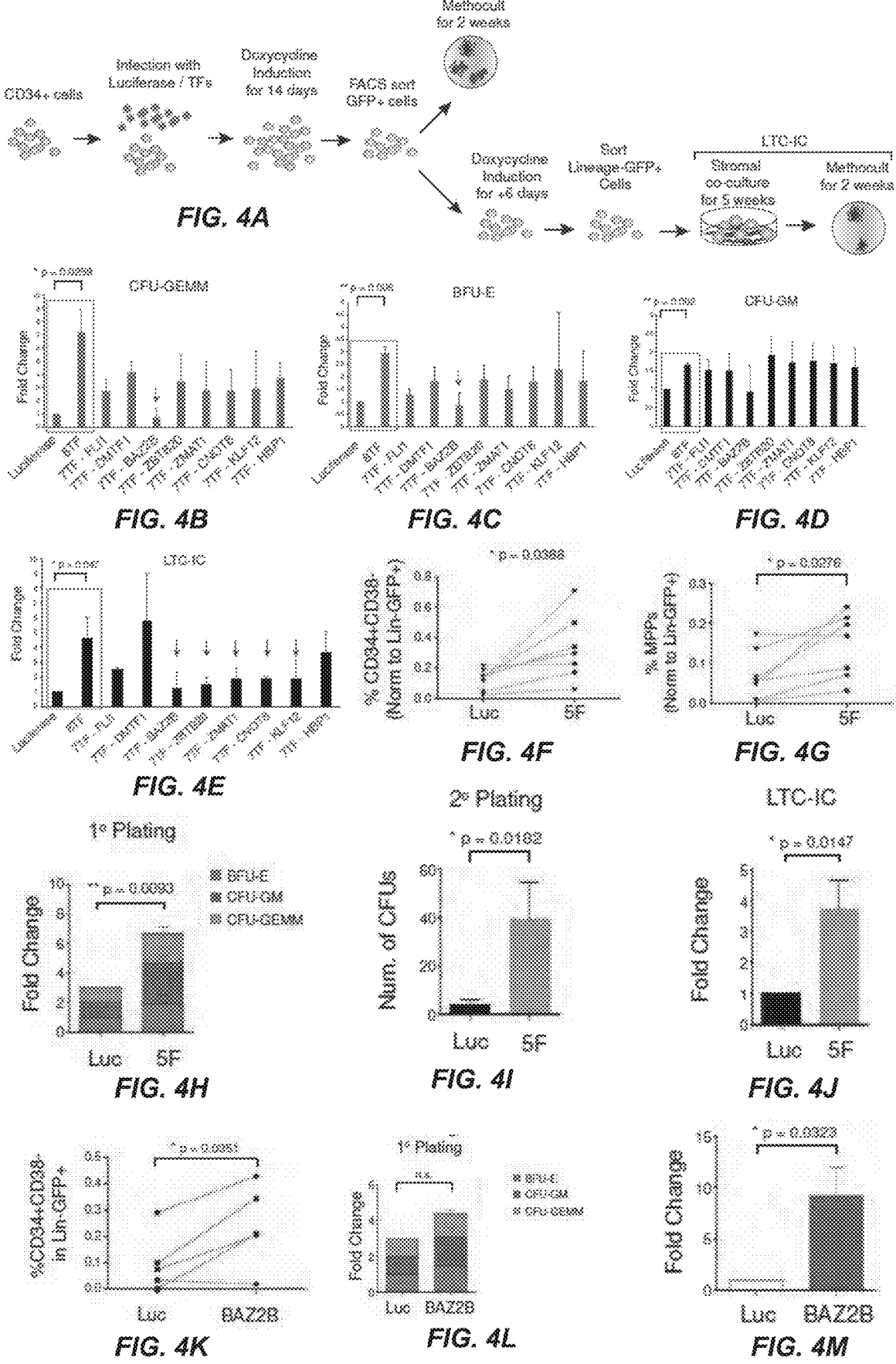
FIG. 4A shows a combination of the predicted transcription factors enhancing the stemness and long-term clonogenicity of CD34+ human hematopoietic cells, particularly showing schematically the experimental workflow of the first screen with human CD34+ hematopoietic stem and progenitor cells.
FIG. 4B is a graph showing human CD34+ cells infected with 8 transcription factors (TFs), or 8 combinations of 7 TFs-1 TF and cultured for 14 days with doxycycline induction, where, on day 14, the GFP+ cells were plated on Methocult assays to count colonies of CFU-GEMM lineage based on morphology. Error bars represent standard deviation for N=3 donors.
FIG. 4C is a graph showing human CD34+ cells infected with 8 transcription factors (TFs), or 8 combinations of 7 TFs-1 TF and cultured for 14 days with doxycycline induction, where, on day 14, the GFP+ cells were plated on Methocult assays to count colonies of BFU-E lineage based on morphology. Error bars represent standard deviation for N=3 donors.
FIG. 4D is a graph showing human CD34+ cells infected with 8 transcription factors (TFs), or 8 combinations of 7 TFs-1 TF and cultured for 14 days with doxycycline induction, where, on day 14, the GFP+ cells were plated on Methocult assays to count colonies of CFU-GM lineage based on morphology. Error bars represent standard deviation for N=3 donors.
FIG. 4E is a graph showing lineage-GFP+ cells sorted on day 20 and plated on a LTC-IC assay followed by counting of colonies. Error bars represent standard deviation for N=3 donors.
FIG. 4F is a graph showing the overexpression of a combination of 5 transcription factors for 14 days in human CD34+ cells, where lineage-GFP+ cells were FACS analyzed or characterized by in vitro colony assays, with the quantification of Lin-CD34+CD38– Stem Progenitors represented for N=5 donors.
FIG. 4G is a graph showing the overexpression of a combination of 5 transcription factors for 14 days in human CD34+ cells, where lineage-GFP+ cells were FACS analyzed or characterized by in vitro colony assays, with the quantification of MPPs represented for N=5 donors.
FIG. 4H is a graph showing the overexpression of a combination of 5 transcription factors for 14 days in human CD34+ cells, where lineage-GFP+ cells were FACS analyzed or characterized by in vitro colony assays, with the quantification of colonies from primary CFC assay N=6 donors. Data represented as mean±SEM.
FIG. 4I is a graph showing the overexpression of a combination of 5 transcription factors for 14 days in human CD34+ cells, where lineage-GFP+ cells were FACS analyzed or characterized by in vitro colony assays, with the quantification of colonies from secondary CFC assay N=5 donors. Data represented as mean±SEM.
FIG. 4J is a graph showing the overexpression of a combination of 5 transcription factors for 14 days in human CD34+ cells, where lineage-GFP+ cells were FACS analyzed or characterized by in vitro colony assays, with the quantification of colonies from LTC-IC CFC assay N=5 donors. Data represented as mean±SEM.
FIG. 4K is a graph showing human CD34+ cells transduced with Luciferase or BAZ2B by Doxy-induced overexpression for 14 days followed by FACS analysis and sorting of Lineage-GFP+ cells for in vitro analysis, with quantification of the CD34+CD38– multipotent stem progenitor within Lineage-GFP+ cells from N=5 donors.
FIG. 4L is a graph showing human CD34+ cells transduced with Luciferase or BAZ2B by Doxy-induced overexpression for 14 days followed by FACS analysis and sorting of Lineage-GFP+ cells for in vitro analysis, with quantification of colonies from primary CFC assay N=5 donors. Data represented as mean±SEM.
FIG. 4M is a graph showing human CD34+ cells transduced with Luciferase or BAZ2B by Doxy-induced overexpression for 14 days followed by FACS analysis and sorting of Lineage-GFP+ cells for in vitro analysis, with quantification of colonies from LTC-IC CFC assay N=5 donors. Data represented as mean±SEM. (B-M) Two-tailed paired t-test **P<0.01, *P<0.05.

Since the Late-MRs were predicted to reprogram the B cells toward an HSC-like state in the heterokaryon system, we reasoned that they were the most suitable candidates to validate the computational predictions by the VIPER algorithm. Therefore, we chose to investigate the role of VIPER-inferred, Late-MRs by assessing their ability to induce stemness in human CD34+ hematopoietic progenitor cells, isolated from umbilical cord blood, toward an HSC-like state. From the Late-MR cluster, of 26 MRs (FIGS. 3C and 3E) we first ranked the TFs based on the high-to-low VIPER-predicted activity for each of the stem fractions (HSC, MPP and MLP) and the heterokaryon 120 h time point (Table 1 of FIG. 15). We then manually selected the top 7 TFs (DMTF1, BAZ2B, ZBTB20, ZMAT1, CNOT8, KLF12, HBP1), with highest VIPER-inferred activity in both late heterokaryons (48 h/120 h) and HSC/MPP/MLP cells, thus most likely to represent mechanistic determinants of the corresponding gene expression signature. FLI1 has been previously shown to play a role in hematopoietic stem cell formation during development as a part of the Gata2/Fli1/Scl transcription factor network in mice. Since FLI1 also enriched as a significantly active MR in the heterokaryons at 120 h and in the HSC MPP population (FIGS. 3C and 3E, and Table 1 of FIG. 15) we included it to produce an 8-TF candidate pool. We cloned their cDNA into a doxycycline inducible lentiviral vector, with a constitutive GFP reporter (FIG. 11A) and we used the luciferase cDNA as control. We infected CD34+ human hematopoietic progenitor cells isolated from umbilical cord blood with different combinations of these 8 TFs (FIG. 4A). Specifically, to identify the candidate MRs providing major contribution to stemness, we tested the effect of a cocktail of all 8 TFs as well as of all possible combinations of 7 out of 8 TFs, by excluding one TF at a time. We performed two distinct in vitro screening assays to test the effect of these candidate MRs on both the stemness and clonogenicity of the transduced CD34+ cells.

In the first screen we induced ectopic, in vitro expression of the 8-TF and of each distinct 7-TF cocktail by culturing the cells with doxycycline for 14 days and a fraction of the transduced (GFP+) cells where first plated into semisolid Methocult medium to test their colony-forming ability (FIG. 4A). Confirming our predictions, we observed that overexpression of all 8 TFs showed a substantial increase of CFU-GEMM (Colony-Forming Unit-Granulocyte, Erythrocyte, Monocyte, Megakaryocyte) colonies, representing the primitive stem progenitors (FIG. 4B, approximately 7-fold increase with respect to the Luciferase control). Indeed, formation of CFU-GEMM units was very low in the Luciferase control. The 8-TF cocktail also increased the number of BFU-E (Burst-Forming Unit-Erythroid) and CFU-GM (CFU-Granulocyte, Monocyte) colonies (approximately 3-fold and 1.7-fold increase respectively, compared to Luciferase control) (FIGS. 4C and 4D). Interestingly, all 7-TF cocktails yielded a lower number of CFU-GEMM colonies (FIG. 4B), thus suggesting that candidate MRs emerging from the VIPER analysis may play complementary roles in stemness induction. However, severe reduction in CFU-GEMM colony formation was observed for the 7-TF cocktail lacking BAZ2B (FIG. 4B), suggesting that this gene may have a dominant role. Consistently, BAZ2B removal also reduced the number of BFU-E and of the CFU-GM colony forming units (FIGS. 4C and 4D).

For the second screening assay, we aimed to increase the stringency of the test by exhausting the short-term proliferating stem and progenitor cells, leaving only the long-term quiescent stem cells in the culture. To accomplish this goal, we maintained expression of the 8-TF cocktail and of luciferase controls in the transduced GFP+ cells for 6 more days and on day 20 we re-sorted the Lineage-GFP+ cells to perform long-term culture-initiating cell (LTC-IC) assays (FIG. 4A). We found that the long-term clonogenic capacity of the cultured progenitor cells was enhanced 5-fold by the 8-TF cocktail compared to luciferase controls (FIG. 4E). However, long-term clonogenicity was compromised in 5 of the 7-TF cocktails, specifically those lacking BAZ2B, ZBTB20, ZMAT1, CNOT8 and KLF12 (FIG. 4E). Interestingly, these 5 TFs (BAZ2B, ZBTB20, ZMAT1, CNOT8 and KLF12) also represent the 5 most statistically significant MRs, based on VIPER-predicted activity in both reprogrammed heterokaryons at 120 h and hematopoietic stem and multipotent fractions (Table 1 of FIG. 15).

To robustly validate these 5 TFs, we performed inducible, co-ectopic expression of the 5-TF cocktail in CD34+ human hematopoietic progenitor cells from 5 individual donors for two weeks, followed by long-term clonogenicity and stemness assays (FIG. 11B). This study showed significant enrichment of the Lin-CD34+CD38– stem/progenitor cells and of the Lineage-GFP+CD34+CD38–CD45RA–90– hematopoietic multipotent cells (p=0.038 and p=0.027 respectively) (FIGS. 4F, 4G and 11C). In sharp contrast, representation of multipotent hematopoietic cells was severely compromised in Luciferase controls.

We further sorted the Lineage-GFP+ cells and cultured them into semisolid Methylcellulose assays to determine their clonogenic and differentiation potential (FIG. 11B). Interestingly, cells transduced with the 5-TF cocktail showed significant increase of BFU-E, CFU-GM and CFU-GEMM colonies in primary Methocult assay (p=0.009) (FIG. 4H and FIG. 11D). To further confirm their clonogenicity, these cells were then re-plated into a second round of semisolid methylcellulose assays (FIG. 11B). Again, transduction with the 5-TF cocktail led to a significantly higher number of CFU compared to Luciferase control (p=0.018) (FIGS. 4I and 11E). Finally, we also verified the long-term clonogenicity of the cells at 2-weeks after transduction with the 5-TF cocktail or Luciferase controls, by plating the Lineage-GFP+ cells into LTC-IC assays (FIG. 11B). Expression of the 5-TF cocktail significantly increased the long-term clonogenic capacity of the CD34+ cells in a consistent manner (p=0.0147) (FIGS. 4J and 11F). Collectively, these data suggest that the overexpression of the 5 genes (BAZ2B, ZBTB20, ZMAT1, CNOT8 and KLF12) in human CD34+ progenitors is effective in inducing stemness and clonogenicity.

We then assessed whether stemness could be induced by a single TF, rather than by a 5-TF cocktail. BAZ2B is the topmost MR with the highest VIPER-predicted activity in both the heterokaryon samples at 120 h and the HSC fractions in the human hematopoietic cells (Table 1 of FIG. 15, and FIG. 3E). Further, from our preliminary screens, we observed that the 7-TF cocktail lacking BAZ2B severely reduced the ability of CD34+ cells to form colonies, compared to the 8-TF cocktail. Moreover, we performed a leading-edge analysis of our heterokaryon dataset using the ARACNe-inferred targets of BAZ2B from the B-cell interactome. Interestingly, the ARACNe-inferred BAZ2B targets that were more significantly differentially expressed included key factors such as EPC2, a Polycomb complex protein; PRMT5, a histone methyl transferase essential for mouse pre-implantation embryonic development; VNN2/ GPI-80, a hematopoietic surface marker essential for human hematopoietic stem cell maintenance and engraftment; TPP1, a gene associated with a critical function in telomeric protection; GEMIN5, an RNA-binding protein that regulates global mRNA translation; LYAR, a transcription factor that targets chromatin factors and regulates gene transcription; and CUL3, an E3 ubiquitin ligase that can regulate the expression of transcriptional MRs from the bromodomain protein family (FIG. 11G). This suggests that BAZ2B has a possible role in regulating the expression of other master regulators of chromatin modification, gene transcription and mRNA translational control. In addition, BAZ2B could also regulate genes controlling telomere protection and hematopoietic cell engraftment and expansion. All these predictions along with the observation that the CD34+ cells displayed an enhanced stemness and clonogenicity after BAZ2B expression, motivated us to further investigate this MR as a critical, single reprogramming factor.

To further elucidate BAZ2B's role in reprogramming, we ectopically expressed it for 2 weeks in human CD34+ cells, followed by clonogenicity and stemness assays. Interestingly, even as a single factor, ectopic BAZ2B expression induced consistent increase in (Lineage-GFP+CD34+ CD38−) hematopoietic stem and multipotent progenitors compared to Luciferase controls (FIG. 4K and FIG. 11H). After 2 weeks of doxycycline-induced overexpression, we sorted Lineage-GFP+ cells into semisolid Methocult and LTC-IC assays.

In the primary colony-forming assay, we observed only a mild increase in the number of colony-forming units (FIGS. 4L and 11I). Interestingly, however, the long-term clonogenic LTC-IC assays showed that the ectopic BAZ2B expression in CD34+ cells resulted in a dramatic increase of colony-forming units, compared to Luciferase controls (p=0.032) (FIG. 4M). Furthermore, in some cases we observed that ectopic BAZ2B expression leads to formation of both BFU-E and CFU-GEMM colonies (FIG. 11J). The CFU-GM colonies from BAZ2B-expressing cells were also much larger, compared to Luciferase-treated cells (FIG. 11J). These data suggest that the overexpression of BAZ2B in CD34+ cells is sufficient to significantly enhance stemness and increase their long-term clonogenic potential.

CD34+ cells consist of a heterogeneous population of stem cells and lineage committed progenitors. The stem and multipotent fraction can be further enriched using a surface marker combination of Lineage-CD34+CD38− that retain long-term engraftment capacity in the bone marrow and peripheral blood. Sorted cells can differentiate into CD33+ myeloid and CD19+ B lymphoid lineages (FIGS. 12A-12F). In contrast, the lineage-committed progenitor fraction isolated by Lin-CD34+CD38+ surface markers were effectively depleted of HSC, MPP and MLP cells, such that sorted progenitors could not engraft in the bone marrow or peripheral blood (FIGS. 12A-12F).

Figures 5A, 5B, 5C, 5D, 5E, 5F, 5G, 5H:
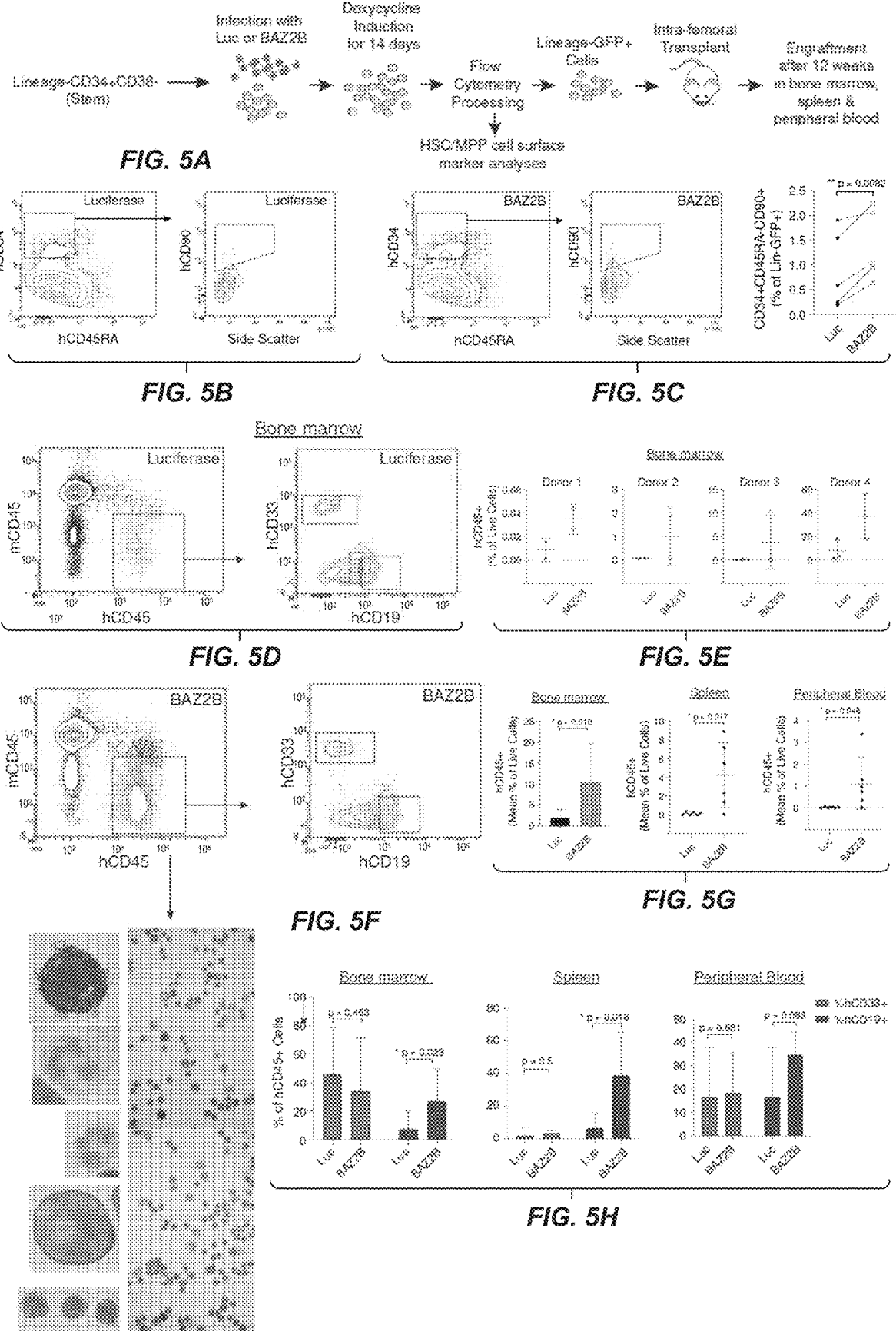
FIG. 5A shows BAZ2B enhancing renewal of Lin-CD34+ CD38– stem progenitor fraction, in the form of a schematic illustration of Lin-CD34+CD38– cells transduced with Luciferase or BAZ2B by in vitro doxycycline-induced expression for 14 days followed by intra-femoral transplantation of irradiated NSG mice.
FIG. 5B shows a FACS analysis of the Lineage-GFP+ population after 14 days of in vitro doxycycline induction, with a representative FACS plot showing the enrichment of CD34+CD45RA–CD90+ population in BAZ2B vs Luciferase transduced cells.
FIG. 5C shows a FACS analysis of the Lineage-GFP+ population after 14 days of in vitro doxycycline induction, with quantification of the CD34+CD45RA–CD90+ normalized to Lineage-GFP+ cells N=5 donors. Two-tailed paired t-test **P<0.01, *P<0.05.
FIG. 5D shows a bone marrow FACS analysis of the transplanted NSG mice after 12 weeks, with a representative FACS plot showing the enrichment of the engrafted human CD45+ cells in the BAZ2B vs Luciferase transduced cells. CD33+ myeloid and CD19+ lymphoid gates show the lineage potential for the human CD45+ cells. Bottom panel: Human CD45+ cells were sorted and stained using the Wright-Giemsa method. Enlarged images from top to bottom show basophils, eosinophils, neutrophils, monocytes and lymphocytes.
FIG. 5E shows a bone marrow FACS analysis of the transplanted NSG mice after 12 weeks, with quantification of engrafted human CD45+ cells within the total live cells of the mouse bone marrow. N=4 donors; 2-3 mice transplanted per donor.
FIG. 5F shows a bone marrow FACS analysis of the transplanted NSG mice after 12 weeks, with mean bone marrow engraftment of human CD45+ cells within the total live cells from N=4 donors. Two-tailed paired t-test **P<0.01, *P<0.05.
FIG. 5G shows a bone marrow FACS analysis of the transplanted NSG mice after 12 weeks, with quantification of engrafted human CD45+ cells in the spleen and peripheral blood of the transplanted NSG mice. N=2 donors; 2-3 mice per donor. Unpaired t-test **P<0.01, *P<0.05.
FIG. 5H shows a bone marrow FACS analysis of the transplanted NSG mice after 12 weeks, with quantification of the CD33+ myeloid and CD19+ lymphoid fraction normalized to the total human CD45+ cells engrafted in the bone marrow, spleen and peripheral blood. Bone marrow N=4 donors; 2-3 mice per donor. Spleen and peripheral blood N=2 donors; 2-3 mice per donor. Unpaired t-test **P<0.01, *P<0.05.

To assess whether BAZ2B could enhance renewal of hematopoietic stem and progenitor cells and increase their in vivo engraftment, we induced expression of exogenous Luciferase or BAZ2B in Lin-CD34+CD38− stem fraction for 14 days and analyzed the cells by FACS (FIG. 5A). BAZ2B overexpression significantly expanded the multipotent stem fraction of CD34+CD45RA−CD90+ within the Lineage-GFP+ population (FIGS. 5B and 5C).

To assess long-term engraftment efficiency, we sorted Lineage-GFP+ cells at 14 d following induction and transplanted them intra-femorally in irradiated NSG mice (FIG. 5A). At 12 weeks after transplantation, BAZ2B-transduced cells showed significant enhancement of engraftment in the bone marrow (FIGS. 5D, 5E and 5F), albeit with significant donor-to-donor variability in bone marrow engraftment efficiency (FIG. 5E). BAZ2B-transduced cells also showed significant enhancement in spleen and peripheral blood engraftment (FIGS. 5G, 12G and 12H) compared to Luciferase transduced controls. We also verified the lineage differentiation capacity of engrafted cells and found that BAZ2B-transduced cells showed an increase in the proportion of CD19+ B-lymphocyte lineage cells within human CD45+ engrafted cells, in the bone marrow, spleen and in the peripheral blood (FIG. 5H). On the other hand, this enhanced lymphoid potential did not compromise the myeloid fraction, since the proportion of the myeloid (CD33+) lineage within the engrafted human CD45+ population was similar in Luciferase and BAZ2B transduced cells in the bone marrow, spleen and peripheral blood (FIG. 5H). We also confirmed that the preferential differentiation toward lymphoid lineage is consistent with the CD19+ lymphoid-biased lineage potential of the uncultured, freshly isolated, Lineage-CD34+CD38− stem fraction transplanted in the NSG mice (FIGS. 12D and 12F). Taken together, these data shows that transient BAZ2B overexpression, during ex vivo expansion of Lineage-CD34+CD38− cells, enhances renewal of long-term engraftable multipotent hematopoietic progenitors that can differentiate into both myeloid and B-lymphoid lineages.

To assess whether ectopic BAZ2B expression may be sufficient to reprogram lineage-committed progenitors toward multipotency, we FACS-sorted the Lin-CD34+ CD38+ committed progenitors (FIG. 6A) that are depleted of HSC, MPP and MLP cell compartments and are thus unable to engraft in the bone marrow (FIGS. 12A-E). We then induced in vitro, doxycycline-mediated expression of BAZ2B or Luciferase in these Lin-CD34+CD38+ committed progenitors for 14 days. Interestingly, ectopic BAZ2B expression induced significant enrichment of the Lin-CD34+CD38− stem and multipotent progenitors, across four different cord blood derived donors (FIGS. 6B and 13A), albeit with significant donor-to-donor variability. We also sorted Lin-GFP+ cells into primary Methocult assays to test their colony-forming ability. Ectopic BAZ2B expression induced consistent and significant increase in the total number of colony-forming units compared to Luciferase (p=0.0171) (FIGS. 6C and 13B). Consistently, the number of BFU-E, CFU-GM and CFU-GEMM colonies was significantly greater following BAZ2B induction. Furthermore, BAZ2B-expressing committed progenitors were also able to form a significantly higher number of colonies in long-term clonogenicity LTC-IC assays (p=0.0109) (FIGS. 6D and 13C). This suggests that ectopic BAZ2B expression alone is sufficient to induce reprogramming of lineage-committed progenitors into a multipotent stem cell state, with increased clonogenic capacity.

To further assess reprogramming potential of the BAZ2B-induced progenitor population, at the molecular level, we performed transcriptional profiling of single cells before and after ectopic BAZ2B expression. To establish a positive control for the stemness signature, we sorted hematopoietic multipotent stem fractions of HSCs (Lin-CD34+CD38−CD45RA− CD90+), MPPs (Lin-CD34+CD38−CD45RA−CD90−), MLPs (Lin-CD34+CD38−CD45RA+) and lineage-committed progenitor populations (Lin-CD34+CD38+), and performed single-cell RNA sequencing and analysis of all these populations (FIG. 13D). To specifically investigate BAZ2B-mediated HSC-like state induction we transduced Luciferase or BAZ2B cDNAs in Lineage-CD34+CD38+ committed progenitors, in vitro, for 14 days and sorted Lineage-GFP+ cells for single-cell expression profiling (FIG. 13D).

We first used the single-cell gene expression profiles of each flow-sorted population (HSC, MPP, MLP, Lineage committed progenitors, BAZ2B expressing Lineage-CD34+CD38+ progenitors and luciferase expressing controls) to generate an ARACNe-inferred, single-cell hematopoietic lineage regulatory networks, independent of prior knowledge. We then used a single cell extension of the VIPER algorithm to measure protein activity at the single-cell level, followed by UMAP dimensionality reduction, resulting into a 2D spatial map of the distinct sub-populations (FIG. 6E). The key advantage of using protein activity rather than gene expression is that, due to the low-depth nature of single cell gene expression profiles, only ~10%-20% of the genes are detected on average in single cell transcriptomes, mostly by a single mRNA read (gene dropout effect). In sharp contrast, by integrating the expression of an entire transcriptional target regulon for each protein, VIPER can accurately infer proteins activity even when their encoding gene is undetectable at the gene expression level, thus resulting in accurate, quantitative activity assessment of ~6,000 proteins, including transcription factors, co-factors, chromatin remodeling enzymes, and signaling proteins.

To refine the reference populations to be used in the model, we performed a probability density analysis to determine the UMAP regions with the highest relative density for each of the four reference populations and filtered them for the top 1% of the differential density to obtain optimal reference single cells representative of each population (FIG. 6F). Indeed, this analysis confirmed activation of well-established, sub-population-specific lineage markers within each reference sample; e.g., GATA2 and HMGA2 in HSCs and MPPs and BCL11A in MLPs (FIG. 13E). A random forest classifier comprising 43 genes (Table 9 of FIG. 23) was trained on these selected reference populations. We then analyzed lineage-committed progenitors overexpressing Luciferase or BAZ2B using VIPER using the random forest model trained on the selected reference populations to classify each single cell as either an HSC, MPP, MLP, or Committed Progenitor. The resulting classification is shown in the circle plots of FIG. 6G, where the distance from the origin is inversely proportional to the classification uncertainty (based on entropy analysis), such that cells with a definitive classification appear near the circumference, while those with more ambiguous classifications appear closer to the circle's center.

The angle at which each cell appears is determined by the average of their classification score across each of the four classes, weighted by a power of two. As expected, classification of committed progenitors overexpressing Luciferase shows a heterogeneous population with a significant proportion of lineage-committed progenitors, a few progenitors with multipotent properties (MPP- or MLP-like cell) and a negligible number of HSC-like cells. In sharp contrast, ectopic BAZ2B expression induced statistically significant increase in the HSC-like compartment (p<2.2e-16), as shown by a dramatic shift of the HSC-specific probability density towards the circumference of the circle plot (FIG. 6G). Increase in HSC-like cells was accompanied by significant depletion in the most differentiated committed progenitors (p<2.2e-16), compared to Luciferase-transduced cells (FIG. 6G). Stemness induction was associated with significant increase of both BAZ2B activity and expression within the same population (FIGS. 13F and 13G). Increase in HSC-like cells was also complemented by significant decrease in multipotent-primed or MPP-like cells (p=3.22×$10^{-9}$) and lymphoid-primed MLP-like cells (p<2.2×$10^{-16}$).

Taken together, these data suggest that, although the lineage-committed progenitors from the Lineage-CD34+CD38+ fraction represent a highly heterogenous population of differentiated and multipotent primed cells, BAZ2B overexpression induces reprogramming of lineage-committed progenitors, lymphoid and multipotent-primed progenitors towards a HSC-like state.

The bromodomain protein BAZ2B is known to play a role in chromatin remodeling that can affect the cell's transcriptional state. To further elucidate BAZ2B's role in chromatin accessibility, we performed ATAC-sequencing analysis of both Luciferase and BAZ2B-transduced committed progenitors, at 14 d following Doxy-induced expression (FIG. 6A). BAZ2B overexpression induced a two-fold increase in accessible chromatin regions (20,054 peaks) in comparison to Luciferase overexpression (10,284 peaks) (FIG. 6H), consistent with less differentiated cells presenting a more unconstrained transcriptional landscape and thus greater entropy. Moreover, 67.8% of the accessible chromatin peaks (12,842 peaks) were unique to BAZ2B-transduced progenitors (FIG. 6H).

We then compared the accessible regions that were uniquely represented in BAZ2B-transduced cells to those of freshly-isolated committed progenitors at day 0 (FIG. 6I). While the latter presented greater chromatin accessibility (82,082 peaks), compared to progenitors overexpressing Luciferase or BAZ2B cultured in vitro for 14 days (FIG. 6I), BAZ2B overexpression increased chromatin accessibility in 6,587 unique peaks, in addition to 6,255 peaks in common with freshly isolated committed progenitors (FIG. 6I). Among the latter, 54.5% occurred in promoter regions, within +/−1 kb from the transcription start sites (FIGS. 6J and 6K). Among the peaks that were uniquely found in BAZ2B-transduced cells and neither in Luciferase-transduced cells nor in freshly isolated committed progenitors (FIGS. 6H and 6I), a vast majority (95.8%) were located in distal enhancer regions at >1 kb from the transcription start sites (FIG. 6J). These peaks indicate increased chromatin accessibility in regions that were otherwise inaccessible in committed progenitors. Indeed, in these regions the chromatin of freshly isolated committed progenitors was predominantly closed, on an interval of at least 1 kb in either direction (FIG. 6L). Overall, these data suggest that BAZ2B overexpression is implicated in both maintenance and remodeling of chromatin structure. On one hand, BAZ2B can preserve accessibility to proximal and distal enhancers chromatin regions already accessible in freshly isolated committed progenitors, thereby reducing the effects of prolonged in vitro cell culture-induced differentiation (FIGS. 6I and 6K). On the other hand, BAZ2B increases chromatin accessibility at unique loci (FIGS. 6L and 6M) leading to the reprogramming of cell transcriptional state, from a committed progenitor state to a hematopoietic stem cell-like state (FIG. 6G). We also found that, despite significant donor-to-donor variability in the overall chromatin accessibility, especially in promoter regions of committed progenitors (FIG.

14A), BAZ2B was able to perform its maintenance and remodeling function consistently across different donors (FIGS. 14A and 14B).

To investigate the potential transcription factors bound in the chromatin accessible regions, we analyzed the nucleosome-free regions (FIG. 14C), that were consistent with the chromatin-accessible regions across all samples (FIGS. 5H and 5I). Compared to Luciferase-expressing cells and Committed Progenitors, motif enrichment analysis of nucleosome-free regions in BAZ2B-expressing cells revealed significant enrichment of motifs representative of specific transcription factor families, including FOS/JUN, GATA, ETV, ERG AND RUNX (FIG. 6M and Tables 10 and 11 of FIGS. 24A-24B and FIGS. 25A-25B, respectively). These transcription factors, in different combinations also with other genes, have been shown to induce reprogramming of fibroblasts, hemogenic endothelium, and adult endothelial cells into hematopoietic stem and progenitor cells. These data suggest that BAZ2B can mechanistically induce genome-wide chromatin remodeling, consistent with transcriptional regulation by master regulator proteins that, in turn, can induce reprogramming of committed progenitors towards a multipotent stem state.

Figure 7A:
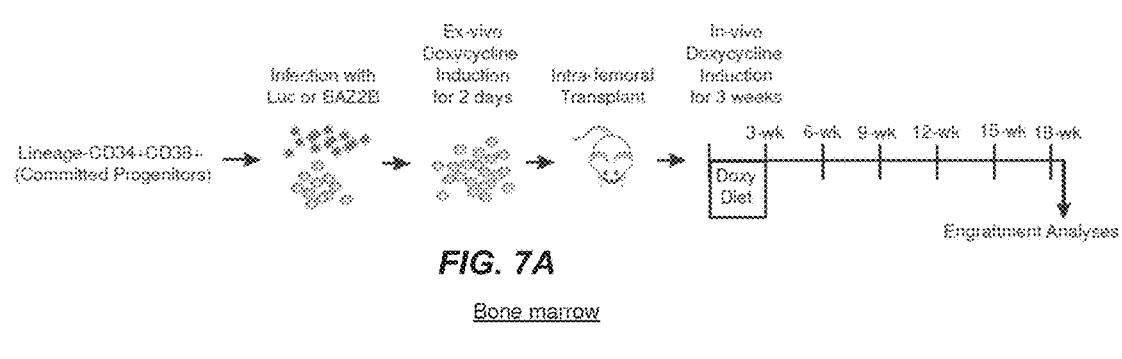
FIG. 7A schematically shows BAZ2B-induced multipotent hematopoietic progenitors possessing long-term engraftment potential, particularly showing in vivo reprogramming of Lin-CD34+CD38+ committed progenitors.
Figure 7B:
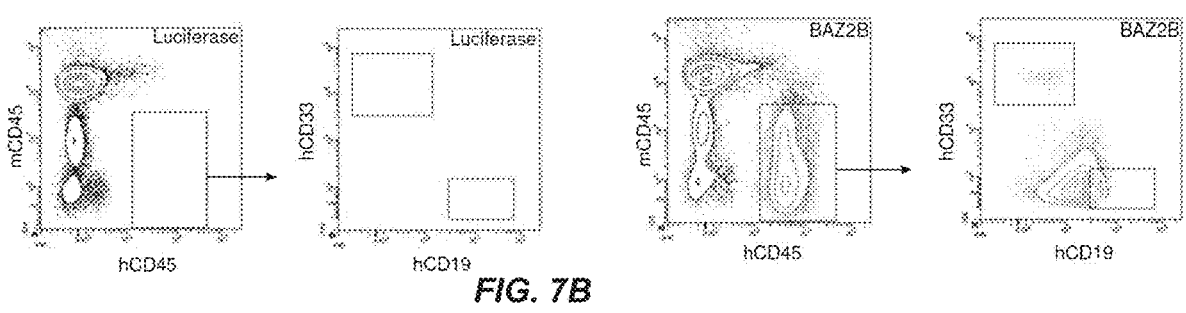
FIG. 7B is a FACS plot showing engraftment of human reprogrammed cells upon expression of BAZ2B or Luciferase in Lin-CD34+CD38+ committed progenitors with their CD33+ myeloid and CD19+ lymphoid lineage potential in transplanted NSG mice after long term engraftment (16 weeks). N=3 donors with 2-3 mice per donor.
Figure 7C:
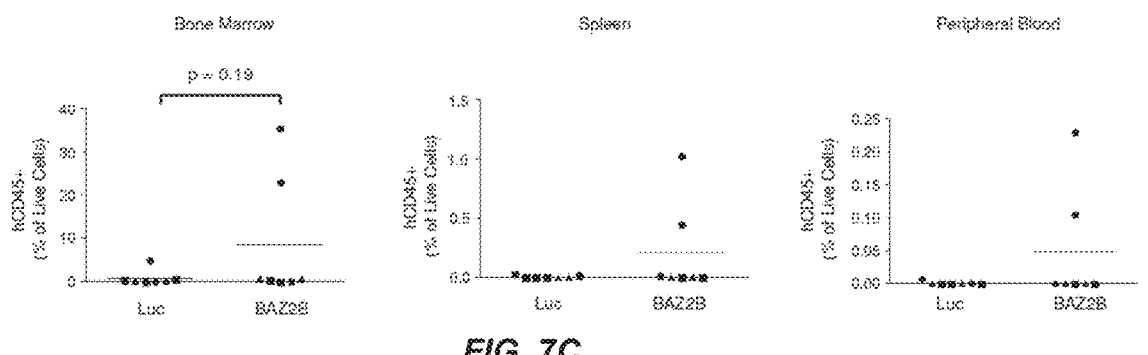
FIG. 7C is a set of plots showing quantification of the engraftment of human CD45+ cells with respect to total live cells in the bone marrow, spleen and peripheral blood.
Figure 7D:
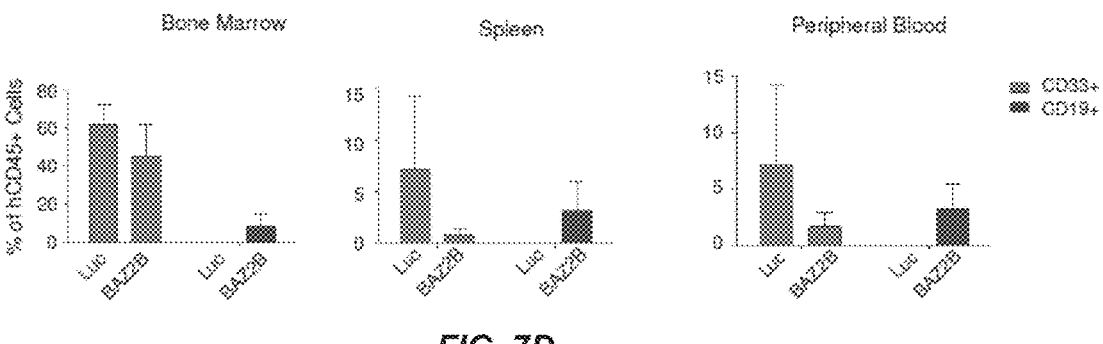
FIG. 7D is a set of graphs showing quantification of the CD33+ myeloid and CD19+ lymphoid potential with respect to the total human CD45+ hematopoietic cells from BAZ2B-induced multipotent hematopoietic progenitors.

To demonstrate long-term engraftment capacity of reprogrammed committed progenitors, we assessed in vivo reprograming of Lin-CD34+CD38+ committed progenitors following doxycycline-induced, ectopic BAZ2B or Luciferase expression (FIG. 7A). Specifically, after an initial 2-day period of in vitro induction, we transplanted the cells into irradiated NSG mice that were then maintained on a doxycycline diet for 3 weeks (FIG. 7A). Mice were then changed to a normal diet and engraftment efficiency was assessed at 16 weeks after resuming the normal diet. Confirming reprogramming of committed progenitors into multipotent hematopoietic progenitors, BAZ2B overexpression led to significant engraftment enhancement in the bone marrow, spleen and peripheral blood (FIGS. 7B, 7C, 14D and 14E), albeit with significant engraftment efficiency variability across mice. Furthermore, reprogrammed progenitors were able to differentiate into CD33+ myeloid and CD19+ lymphoid lineage cells (FIG. 7D). Taken together, these data suggest that BAZ2B overexpression in lineage-committed progenitors was effective in reprograming these cells towards a multipotent hematopoietic progenitor state, promoting enhanced stemness, clonogenicity and long-term engraftment potential.

Reprogramming of somatic cells toward a hematopoietic precursor lineage is widely studied, since the precise molecular mechanisms presiding over this process are still elusive. Given the relevance of hematopoiesis in clinical care, this also represents a critically important area of investigation for translational medicine applications. In this study, we used an advanced systems biology approach, originally designed for the elucidation of tumor related mechanisms, to identify Master Regulators (MRs) protein that mechanistically control—via their transcriptional targets—the onset of the reprogramming process. We generated interspecies heterokaryons by fusing murine Tcf7l1⁻/⁻ ESCs with mature human B-lymphocytes, thus inducing their reprogramming to a multipotent state and allowing precise characterization of the molecular events following the fusion. After sequencing the human transcriptome, we carried out a transcription factor regulatory network analysis using the ARACNe and VIPER algorithms and identified candidate MRs that are critical drivers of reprogramming. Overall, we set up a highly generalizable approach, consisting of a combination of innovative systems biology algorithms with the heterokaryon model to study reprogramming of human cells to a multipotent state. The application of this methodology led us to discover key reprogramming MRs that could reprogram lymphoid cells to a multipotent hematopoietic stem state. However, importantly, this approach can be used to study any reprogramming event that can be followed over time either in bulk population or in single cells, including previously reported heterokaryon-mediated and direct transcription factor-mediated reprogramming.

Our analytical approach predicted the MRs in an unbiased manner based on their activities rather than on changes of their differential expression, as it is often done in other conventional RNA sequencing studies. Of note, the MR activity is not necessarily concordant with the expression level of the factors, i.e., active MRs that are maybe regulated at post-transcriptional level, do not necessarily display increased mRNA expression. As a result, we have discovered a novel mechanism of cell-fusion mediated reprogramming where the human B-cells were reprogrammed to a hematopoietic multipotent stem progenitor-like state.

We observed that the reprogramming of the human B-lymphocytes is temporally regulated by two distinct clusters of transcription factors, namely "Early" and "Late" enriched into the proliferative lineage-committed progenitors (CMP, MEP, GMP) and in the hematopoietic stem and multipotent cells (HSC, MPP, MLP), respectively. This demonstrates that the human B-lymphocytes upon fusion with mouse ESCs, are reprogrammed within the hematopoietic hierarchy to a multipotent hematopoietic stem progenitor-like state rather than to an embryonic stem pluripotent state. It is worth mentioning that we have only measured the heterokaryon cell mRNA expression up to 5 days after fusion. Therefore, whether the B nuclei within the heterokaryons will be reprogrammed to a pluripotent state at later time-points remains an open question.

Overall, our discoveries in this study provide novel insights into the molecular mechanism of cell-fusion mediated reprogramming. Indeed, we have identified and experimentally validated a single MR, BAZ2B, which we showed to be able to reprogram the hematopoietic lineage-committed progenitors into multipotent stem state. The overexpression of BAZ2B in the lineage-committed progenitors enhanced the formation of multipotent hematopoietic progenitors with an increased long-term clonogenicity, enhanced engraftment potential and the ability of the reprogrammed cells to differentiate into cells of multiple lineages. We observed significant variability of engraftment among transplanted mice. This was expected since, as described for the self-renewal and reprogramming experiments (FIGS. 5E and 6B) both the human hematopoietic stem and committed progenitor fractions show a great level of phenotypic variability from donor to donor. Furthermore, the experimental setup for in vivo reprogramming requires maintaining a steady plasma concentration of doxycycline which in turn relies on the food and water consumption habits of the mice, which may vary on an individual level this could lead to the variability in the in vivo reprogramming process.

Reprogramming of lineage-committed hematopoietic progenitors toward a HSC-like state was also confirmed by single-cell transcriptome analysis. Indeed, overexpression of BAZ2B in Lin-CD34+CD38+ committed progenitors for 14 days, induced a significant enrichment of the gene expression signature for stem and multipotent fractions of HSCs, MPPs and MLPs.

Work from several laboratories have reported the generation of multipotent hematopoietic progenitors from various types of somatic cells or progenitors. Murine fibroblasts were reprogrammed to hemogenic endothelial precursor cells using a combination of 4 genes—GATA2, Gfi1b, cFos and Etv6. Another study reported the reprogramming of murine fibroblasts into multipotent hematopoietic progenitor cells using a combination of 5 genes—ERG, GATA2, LMO2, RUNX1c and SCL. Murine lineage-committed progenitors were reprogrammed into multipotent hematopoietic progenitors using a combination of 6 genes—Run1t1, Hlf, Lmo2, Prdm5, Pbx1, and Zfp37. In another study, human endothelial cells have been reprogrammed to multipotent hematopoietic progenitors using a combination of 4 genes—FOSB, GFI1, RUNX1 and SPI1. Interestingly, we found that overexpression of BAZ2B alone in the committed hematopoietic progenitors, increased the chromatin-accessibility for genomic regions enriched motif-binding sites for FOS, GATA, ETV, ERG and RUNX. This indicates that BAZ2B has the potential to initiate the function of other genes or master regulators that maybe necessary for driving the reprogramming process.

Importantly, in all of these studies above mentioned, a combination of 4 or more genes have been used to reprogram the differentiated cells. Based on our computational predictions of transcription regulatory networks, we confirmed the ability of one single gene, BAZ2B, to function as MR that can reprogram the lineage committed progenitors to multipotent hematopoietic stem and progenitor cells. Furthermore, we have also confirmed that BAZ2B alone can also enhance the renewal of the Lineage-CD34+CD38– hematopoietic stem and multipotent progenitors. In both scenarios, we also observe that the reprogrammed or renewed multipotent progenitors had a higher CD19+ lymphoid lineage potential in comparison to the CD33+ myeloid potential. This is consistent with the lineage potential of the freshly isolated Lineage-CD34+CD38– hematopoietic stem fraction (FIG. 13F). Thus, the BAZ2B-induced multipotent hematopoietic progenitors can recapitulate the long-term engraftment and lineage potential that are characteristic features of the Lineage-CD34+CD38– hematopoietic stem fraction.

The BAZ2B protein and its functional activity is not well understood. It consists of a bromodomain (BRD) and a plant homeodomain (PHD). Crystal structure studies of purified BAZ2B protein show that the PHD domain interacts with unmodified histone H3K4 and the bromodomain can interact with the acetylated histone marks on H3K14 and H3K16. Human BAZ2B protein has been identified as a novel component of the ISWI chromatin remodeling complex and physically interacts with the ISWI sub-components, SMARCA1 and SMARCA5. The BAZ2B-interaction with the ISWI forms a catalytically active complex and induces in vitro remodeling of the DNA-bound mononucleosomes. In our heterokaryon studies, we found that the leading edge predicted targets of the BAZ2B gene include Polycomb factors, components of chromatin remodeling complexes and genes essential for human HSCs, among others. Based on this evidence, we hypothesized that BAZ2B can induce reprogramming of the lineage-committed progenitors into multipotent cells through its remodeling activity rewiring the chromatin genome-wide.

With the ATAC-seq studies, we found that BAZ2B can maintain open the chromatin architecture of the committed progenitors cultured in vitro, and also can remodel the chromatin to enhance accessibility to de novo genomic loci that were otherwise closed in the committed progenitors. Interestingly, we also found that a large majority of these genomic loci were in the distal enhancer regions, and included binding sites for FOS, JUN, ETV, ERG or RUNX transcription factor families. Thus, these distal enhancers are potentially targeted by these transcription factor families that were shown to be efficient to induce reprogramming of fibroblasts and endothelial cells into hematopoietic stem and multipotent progenitors. Our studies suggest the potential for BAZ2B to also reprogram fibroblasts and endothelial cells, a possibility that remains to be tested.

Beside its reprogramming function via a putative chromatin remodeling activity, we also propose that BAZ2B forms part of a critical transcription factor network, which enhances stemness and multipotency in hematopoietic cells. This finding might have important clinical applications. Indeed, a large majority of patients requiring transplantation are unable to find a matching donor within their own family and have to rely on transplants from unrelated donors. However, graft-versus-host disease contributes to a significant risk of mortality in those receiving transplants from unrelated donors. Consequently, there is a high demand of hematopoietic multipotent cells despite the lack of histo-compatible donors. Thus, there is an urgent need to develop methods to produce an autologous source of these cells from peripheral blood cells or from committed bone marrow-derived progenitors of the individuals in need of transplantation. Our findings might have important applications in the major goal of generating autologous or heterologous transplantable human hematopoietic multipotent cells (e.g., from umbilical cord blood cells). It should be understood that this is not the only application contemplated. Non-limiting examples of further applications include the reprogramming of not only CD34+ progenitors derived from blood, but also from human iPS cells and/or endothelial cells derived from the human umbilical vein; the reprogramming of terminally committed cells, such as adult fibroblasts or peripheral blood hematopoietic cells (such as monocytes into hematopoietic stem progenitors); and combination with compounds used to enhance the transplantation efficiency of ex-vivo cultured progenitor cells (e.g. UM171 and SR1).

Finally, our work also suggests that regulatory-network-based analysis of heterokaryon RNA profiles can provide critical novel biological insights, which are unlikely to emerge using more conventional gene-discovery methods based on literature mining or on differential gene expression analysis. As an ever-increasing number of large-scale RNA-sequencing data keep accumulating in literature, such systems biology strategies are emerging as being uniquely poised to glean relevant insights from them.

Tcf7l1−/− mouse embryonic stem cells (mESCs) were donated by Dr. Brad Merrill (UIC, USA). The mESCs were cultured in media supplemented with 20% serum and mLIF. The human B-cell line are EBV-immortalized human B lymphocytes that were obtained from the Corriell Institute of Medical Research (GM22647). The lymphoblast cell line was derived by Epstein-Barr Virus mediated immortalization of peripheral blood mononuclear cells (PBMCs) from a healthy Caucasian individual. The genotype of the lymphoblast cell line was thoroughly assessed and showed a high concordance with the donor's PBMCs. The cell line did not show any abnormal copy number variations, or genetic mosaicism. The human B-cells were cultured in RPMI media supplemented with 20% fetal bovine serum.

Umbilical cord blood samples were purchased from the blood bank of Barcelona (Banc de Sang I Teixits) after approval from the Clinical Research Ethical Committee (CEIC, Parc de Salut Mar, Barcelona). For all of our experiments, the human hematopoietic stem and progenitor cells were derived from fresh umbilical cord blood that were collected within less than 26 hours. Briefly we isolated the mononuclear cells from a fresh cord blood sample using a Ficoll® gradient (Lymphoprep®, Stemcell Technologies®), followed by magnetic isolation of CD34+ cells using the Miltenyi® human CD34 Ultrapure enrichment kit (Catalog #130-100-453) according to the manufacturer's instructions. For some of the experiments, we purchased frozen CD34+ human cord blood cells from Stemcell Technologies® (Catalog #70008.5).

Human CD34+ cells were cultured in serum-free enhanced media (Stemspan® SFEM, StemCell Technologies®) supplemented with two different formulations of recombinant human cytokines, (1) Stimulation media—contains SCF 300 ng/ml, FLT3 300 ng/ml, TPO 100 ng/ml, IL3 60 ng/ml (2) Maintenance media—SCF 100 ng/ml, FLT3 100 ng/ml, TPO 100 ng/ml, IL3 20 ng/ml, IL6 20 ng/ml and doxycycline 2 μg/ml. For experiments using the entire fraction of CD34+ cells, the cells were incubated in the stimulation media for 24 hours at 37° C. The cells were then infected for a first round with lentiviral vectors and incubated overnight in the stimulation media at 37° C. The cells were then washed and re-suspended in stimulation media. After approximately 4 hours the cells were re-infected for a second round with lentiviral vectors and continued incubation overnight at 37° C. The cells were then washed and cultured in the maintenance media supplemented with 2 μg/ml of Doxycycline (Sigma Aldrich®, Catalog #D9891) for the rest of the experiment. Every 2 days the cells were washed and re-plated in fresh media with doxycycline. For experiments associated with transplantation, we used the Stemspan® SFEM II (StemCell Technologies®) basal media. The maintenance media composition was changed to SCF 100 ng/ml, FLT3 100 ng/ml, TPO 50 ng/ml, UM171 35 nM (StemCell Technologies®), SR1 750 nM (StemCell Technologies®), LDL 10 μg/ml (StemCell Technologies®) and doxycycline 2 μg/ml.

To isolate the Lineage-CD34+CD38+ lineage committed progenitors the CD34+ enriched cells were treated with anti-CD34 antibodies that targets a distinct epitope other than one used for isolation. For CD34+ cells isolated using the Miltenyi® CD34 enrichment kits, we used the APC-labelled anti-human CD34 (Clone AC136). For the CD34+ cells purchased from StemCell Technologies® we used the AlexaFluor700 labeled anti-human CD34 (Clone 581). In addition, we used a combination of anti-CD38 (Clone HBC) antibody and a biotin-labeled cocktail of antibodies (from Miltenyi®) targeting the "Lineage" antigens CD2, CD3, CD11b, CD14, CD15, CD16, CD19, CD56, CD123, and CD235a. The cells were then sorted using BD FACS ARIA II flow cytometer. The sorted cells were cultured in the maintenance media—SFEM supplemented with SCF 100 ng/ml, FLT3 100 ng/ml, TPO 100 ng/ml, IL3 20 ng/ml, IL6 20 ng/ml and doxycycline 2 μg/ml. Approximately 2 hours after sorting, the cells were infected with a first round of the lentiviral vectors and incubated overnight at 37° C. The cells were then washed and re-suspended in the maintenance media. After approximately 4 hours the cells were re-infected with a second round of lentiviral vectors and continued incubation overnight at 37° C. The cells were then washed and cultured in the maintenance media supplemented with 2 μg/ml of Doxycycline for the remainder of the experiment with fresh media changes for every 2 days.

Adult NOD.Cg-Prkdc$^{scid}$ Il2rg$^{tm1Wjl}$/SzJ (NSG) mice at the age of 9-10 weeks were sublethally irradiated (200-225 rads). After 24 hours, the mice were transplanted intra-femorally with the FACS-sorted cells. Bone marrow or peripheral blood was analyzed at 12-16 weeks after transplantation. For the in vivo reprogramming experiments, 2-3 days prior to transplantation, the NSG mice were placed on a doxycycline diet consisting of food pellets containing 625 ppm of doxycycline (SAFE Diets—E8220 Version 0232) and drinking water infused with 1 mg/ml of doxycycline.

For each human-mouse fused heterokaryon sample, 30 million Tcf7l1−/− mESCs were labeled with Vybrant® DiD (1:400) and 30 million human B lymphocytes were labeled with Vybrant® DiO (1:400) for 15 mins at 37° C. The labeled cells were then washed twice with PBS and resuspended in 6 ml of PBS each. The mESCs and the human B-cells were then mixed in a 1:1 proportion and then centrifuged to pellet the cells. The pellet was disrupted and then resuspended in Polyethylene Glycol (PEG) in a dropwise manner with the procedure lasting a maximum of 60 seconds. They were then incubated at 37° C. for 90 seconds. The cells were then re-suspended slowly with serum-free DMEM in a dropwise manner, and constant shaking. The cells were then incubated for 3 min at 37° C. and spun down to recover a pellet. The supernatant was discarded and fresh mESC media (+LIF) was added without disrupting the pellet. The cells were then incubated at 37° C. for 3 mins and then plated on gelatin-coated plates. For the time points at 4 hours, 12 hours and 48 hours, the cells were harvested by collecting them in suspension in the supernatant followed by trypsinization of the remaining adherent cells on the plate surface. The cells were than washed and re-suspended in PBS (with 3% FBS and 2.5 mM EDTA) to be processed for FACS sorting. They were then sorted directly into the lysis buffer (Buffer RLT) provided in the Qiagen® RNEasy mini kit (74104) using a 100 μm nozzle at the flow cytometer (BD FACS ARIA II SORP). For the timepoint at day 5, we altered our sorting strategy. The cells were fused and plated on gelatin-coated plates as described above. After 4 hours all the cells were harvested and the fused hybrids were sorted and replated on gelatin-coated plates in mESC media for 5 days. On day 5 all the cells were harvested again by trypsinization and lysed with lysis buffer (Buffer RLT) for RNA extraction using the Qiagen® RNEasy mini kit (74104).

The fused cells were sorted as described above onto a slide. The cells were fixed with 4% PFA for 15 minutes at room temperature and then permeabilized with 0.3% triton for 20 minutes at room temperature. Blocking was performed for 30 minutes with 1% goat serum and 0.05% tween. The anti-human Lamin A/C (clone 636) was diluted 1:100 in blocking solution followed by incubation with the cells for 90 minutes at room temperature. The cells were then washed with PBS followed by incubation with the secondary antibody, goat anti-mouse Alexa 488 at 1:400 dilution for 45 mins at room temperature. The cells were washed again and then incubated with Alexa Fluor 568 Phalloidin at a dilution of 1:40 for 20 mins at room temperature. The cells were then washed and stained with the DNA-labeling dye DAPI. Confocal imaging was performed on a Leica® TCS SPE inverted confocal microscope.

RNA Samples isolated from the heterokaryons were further processed to generate sequencing libraries using a Truseq® RNA library Prep Kit. The libraries were then analyzed on an Illumina® HiSeq 2000 sequencer using 100 bp paired-end sequencing.

Single-cell RNA sequencing libraries were generated at the JP Sulzberger Columbia Genome Center using a 10× Genomics Chromium Controller and Single-cell 3' Library & Gel Bead Kit v2 (10× Genomics®, #120237). Single cells were sorted in a BD Influx cytometer and were pelleted by centrifugation (300rcf, 5 min) followed by resuspension in DMEM at approximately 500 cells/μl. Cell viability and concentration was verified using a Countess II Automated Cell Counter (ThermoFisher®, #AMQAX1000). Each sample was loaded into one well of a Chromium chip (10× Genomics®, #120236), following manufacturer's instructions, and aiming for a recovery of 5,000 cells per sample. Library construction was carried out according to the manufacturer's instructions and were sequenced on Illumina® Hiseq 2000. The sequenced reads were processed through the Cell Ranger (10× Genomics) pipeline to generate the single-cell gene expression profile.

The hematopoietic cell dataset used in our analysis was a previously published dataset that was generated from human HSCs and progenitor cell populations that were isolated from human cord blood. The inventors obtained RNA from flow-sorted populations of human cord blood based on surface expression levels of CD34, CD38, CD45RA, Thy1 and CD49f, CD10, CD7, CD19 and CD1a. Samples were profiled using the Illumina® HumanHT-12 WG-DASL v 4.0 R2 expression beadchip. The reference dataset was publicly available through the Gene Expression Omnibus (GSE42414).

Human CD34+ cells were analyzed and sorted on a FACS ARIA II Cytometer (BD Biosciences). Prior to the FACS processing, the cells were blocked using the human Fc Block (Miltenyi®) for 10 minutes on ice. Following this, the cells were washed and incubated with the specific panel of fluorescence/biotin labeled primary antibodies for 30 mins on ice. In the case of a use of biotin-labeled primary antibodies, the cells were further washed and re-incubated with PE-CF594 streptavidin for 10 mins on ice.

For the FACS analysis of HSC and MPP populations in our cell culture experiments, we used the following combination of antibodies—Alexa Fluor 700 anti-human CD34 (clone 581), PE-Cy7 anti-human CD38 (clone HB7), APC anti-human CD45RA (clone HI100), PE anti-human CD90 (clone 5E10), and antibody and a biotin-labeled cocktail of antibodies (from Miltenyi®) targeting the "Lineage" antigens CD2, CD3, CD11b, CD14, CD15, CD16, CD19, CD56, CD123, and CD235a.

For the primary colony-forming cell (CFC) assays, the 2000 FACS-sorted HSPCs were plated in Human Methocult (H4434, StemCell Technologies®) on 35 mm plates and cultured for 14 days at 37° C. before the enumeration of colonies. For secondary CFC assays all the cells from the primary plating were collected in PBS and re-plated in Human Methocult (H4434, StemCell Technologies®) on 35 mm plates and cultured for another 14 days at 37° C. The counting of colonies in both primary and secondary plating were performed using a blind method.

Mouse bone marrow stromal cells, M2-10B4, were irradiated at 40 Gy and plated on collagen-coated 6 well plates at a density of approximately 250,000 cells per well. After approximately 24 hours, 60,000 FACS-sorted human Lineage-GFP+ cells were plated on the irradiated feeders and cultured in Human Myelocult media (H5100, StemCell Technologies®) for 5 weeks at 37° C. Every week 1 ml of the media was removed and refreshed with fresh media. At the end of 5 weeks, all the cells from each well were harvested by trypsinization and plated in Human Methocult Enriched media (H4435, StemCell Technologies®) and cultured for 2 weeks at 37° C. after which the colonies were enumerated by the blind method.

Briefly, the 35 mm plates were labeled on the side-walls of the plate on the day of plating, instead of the lids. On the day of counting, all of the control and treated plates were shuffled and the plates were given random reference numbers on the top of the lids. The colonies in each plate was counted and noted by the given reference numbers. At the end of counting all the plates, the labels on the side-walls were matched with the assigned random reference numbers on top of the lid.

The lentiviral vector pInducer11-miR-RUG that was purchased from Addgene® was designed to clone and express miR based-short hairpins under an inducible CMV promoter. The 14.7 kb vector was modified to replace the miR sequence with a RefA gateway cassette to allow Gateway cloning of human cDNAs. The vector was digested with AgeI and MluI to dropout a fragment (approximate size 2 kb) downstream of the CMV promoter that includes the miR sequence and the Turbo RFP reporter. The 5' and 3' ends of the remaining 12 kb vector were then blunted using the Klenow polymerase. The RefA gateway cassette was then inserted into the vector by blunt-end ligation to generate the modified lentiviral vector, referred to as pInducer11-gw.

Human cDNAs were purchased from the Harvard Plasmid Database. The cDNAs for FLI1, KLF12 and HBP1 originally in entry vector pDNOR221 were cloned into pInducer11-gw by Gateway LR cloning. The cDNAs for CNOT8 (originally in entry vector pOTB7) and ZBTB20 (originally in entry vector pCMV-SPORT6) were first cloned into the pDONR221 entry vector by a Gateway BP reaction. Subsequently the cDNAs were transferred from pDONR221 to pInducer11-gw by a Gateway LR reaction. The cDNA for ZMAT1 (originally in cloning vector pCR-XL-TOPO) was amplified by PCR using the forward primer (5'-GGGCCCCATCTTTATTGGAAAATGT-3') with a 5' attB1 gateway cloning adapter and the reverse primer (5'-ACCTCTCCTTTTCTTCATCAGGTGT-3') with 5' attB2 cloning adapter. The amplified PCR product was then cloned into pDONR221 by gateway LR reaction. The cDNAs for BAZ2B and DMTF1 originally in the vector pENTR223 lacked a termination codon for C-term fusion cloning. Using the Quikchange II site-directed mutagenesis kit (Agilent Technologies®) we first inserted a termination stop codon for BAZ2B cDNA within the pENTR223 vector using the forward primer (5'-GCAAAAAGAACAGATAAC-CAACTTT CTTGTAC-3') and the reverse primer (5'-GTA-CAAGAAAGTTGGTTATCTGTTCTTTTT GC-3'). We used a similar site-directed mutagenesis strategy to insert a termination stop codon for DMTF1 cDNA within the pENTR223 vector, using the forward primer (5'-GGTAAACTGTCATTAGCCAACTTTCTTGTAC-3') and the reverse primer (5'-GTA-CAAGAAAGTTGGCTAATGACAGTTTACC-3'). Finally we transferred the full-length BAZ2B and DMTF1 cDNAs (with termination codons) from the pENTR223 vector to the pInducer11-gw using the gateway LR reaction.

The cDNA for Luciferase was obtained from Addgene® in pDONR223 entry vector. The Luciferase cDNA did not have a stop codon. The cDNA was cloned in to the destination vector pInducer11-gw by Gateway LR cloning. Upon recombination, the Luciferase cDNA was in-frame with a STOP codon in the destination vector generated by the recombined vector sequence.

For production of lentiviral particles, HEK293T cells were transfected using the Calcium Phosphate Transfection Kit (Clontech®). On day one 12.5 million HEK293T cells were plated on 150 mm dishes and after approximately 24 hours the media was refreshed to prepare for transfection. For each plate, the plasmid cocktail was prepared by mixing the Lentiviral vector, the pCMV-dR8.9 packaging plasmid, and the VSVG plasmid expressing the envelope glycoprotein. The cells were then transfected using the Calphos Mammalian Transfection Kit (Clontech®) as per the manufacturer's instructions. The cells were then incubated at 37° C. overnight. On day 1 after the transfection, the cells were washed with PBS and were refreshed with fresh media. On day 2 the supernatant was collected and ultracentrifuged at in a Beckman Coulter® L-100K centrifuge at 64047 g for 2 hours at 22°. The cells were replenished with fresh media and incubated overnight at 37° C. The virus pellet was then resuspended in PBS and stored at 4°. On day 2 after transfection the supernatant was collected and once again a virus pellet was obtained by ultracentrifugation in a Beckman Coulter® L-100K centrifuge at 64047 g for 2 hours at 22°. The PBS suspension with the virus from day one was used to resuspend the fresh virus pellet from day 2 and stored at 4° overnight. The following day the viruses were aliquoted and stored at –80° C.

For estimating the viral titer, HEK293T cells were plated into 6-well plates at a density of 500,000 cells per well. The frozen viral pellets were thawed and for each lentiviral vector we prepared a dilution series from 1:10 to 1:320. The 293T cells were infected with the respective dilutions and after 48 hours the cells were processed for flow cytometry to detect GFP positive cells. The titer was calculated using the formula: Transducing Units per ml=(% of GFP positive cells×number cells at the time of transduction×Fold Dilution×1000)×volume of diluted vector used for transduction.

RNA-Seq reads were first mapped to the *Mus musculus* assembly 10 reference genome (mm10), and the human assembly 19 (hg19) reference genome using TopHat (v 2.0.4). Reads mapping to known genes, based on Entrez gene identifiers, were then counted using the GenomicFeatures R-system package (Bioconductor®).

Multi-mapping reads that came either from the ES Mouse nucleus or the Human B-cell nucleus contributed to approximately 5% of the total reads sequenced. In order to maintain the integrity of all the sequenced reads, we attempted to include the reads into the count files into the final counts by taking the following steps. We first increased the stringency of the mapping, of the paired-end sequencing reads. More specifically, the "no-mixed" flag in TopHat assured that alignments where both reads in the pair were mapped were included. The "no-discordant" flag assured that only concordant reads were mapped, meaning the reads had the expected mate orientation and expected distance between them. Once the reads were mapped, the read names given by the Illumina® Sequencer were used to separate the reads that mapped uniquely to each genome to multi-mapping reads that mapped to both genomes. First the counts were summarized using the GenomicRanges package on Bioconductor®.

Next we reasoned that the multi-mapping reads would fall into one of 3 situations. In the first situation, the reads would map to both the mouse and human genomes, but would only map to a gene in one of genomes. In this case the reads were assigned to the appropriate gene. Next, we used the CIGAR field, which is a feature of the SAM file and gives a representation of how the read mapped to the reference genome, and whether there was a match/mismatch, insertion, deletion, or if any positions were skipped. We used the CIGAR score to determine which genome a read mapped to, and if there was a difference, then the read was assigned to the genome with the higher quality read.

Finally, we considered reads that mapped perfectly to genes in both genomes. For these we chose to "fairly split" the reads between each of the genomes by considering how many unique reads had already been mapped to each gene. We reasoned, that the multi-mapped reads would follow the same overall proportion of expression that would already be modeled by the unique reads, which would be affected by differences in gene length, expression levels, or a combination of both. For example, if a read had been assigned to a mouse gene that already had 15 unique reads mapped to it, and a human gene that already had 3 unique reads mapped to it, then the mouse gene would receive $^{15}/_{18}$th of the read and the human gene would receive $^{3}/_{18}$th of the read. The final counts were later rounded to the nearest integer value.

The B-cell regulatory network (BCRN) used in this study was an integration of two previously published datasets. The first human BCRN was reverse engineered by the ARACNe algorithm from a dataset of 264 gene expression profiles that included normal (naive and germinal-center B-cells), several tumor phenotypes including, B-cell lymphomas and cell lines. Gene expression was profiled on Affymetrix® U133 Plus 2.0 arrays, processed by the Cleaner algorithm, and normalized with MAS5. The resulting BCRN and contained predictions for 1,223 transcription factors regulating 13,007 target genes through 327,837 interactions. The second human BCRN was built from an additional set of 254 samples including normal cells, several tumor phenotypes and cell lines. Gene expression for this dataset was profiled on Affymetrix® H-GU95Av2 arrays, and also went through processing through MAS5, Cleaner and ARACNe. This second regulatory network included 173,539 predicted interactions between 633 transcription factors and 6,403 genes. The integration was done by taking a union of the predictions of the two networks, with TF-target interactions that were predicted by both networks having their p-values integrated using Fisher's method. The final BCRN contained predictions for 1,241 transcription factors regulating 11,770 target genes through 288,616 interactions.

The relative activity of each transcription factor represented in the BCRN was inferred using the VIPER algorithm, available as a package through Bioconductor®. Conceptually, the VIPER algorithm is similar to the Master Regulator Inference Algorithm (MARINA), which uses the TF targets inferred by the ARACNe algorithm to predict drivers of changes in cellular phenotypes. In addition to calculating the enrichment of ARACNe-predicted targets in the signature of interest, VIPER also takes into account the regulator mode of action, regulator-target gene interaction confidence and pleiotropic nature of each target gene regulation. Statistical significance, including P value and normalized enrichment score (NES), was estimated by comparison to a null model generated by permuting the samples uniformly at random 1,000 times.

To identify transcription factors (TFs), we selected the mouse genes annotated as "transcription factor activity" in Gene Ontology and the list of TFs from TRANSFAC. This produced a final list of 1,794 TFs, which mapped to 3,758 probesets on the gcrma-normalized expression profile.

Since the HSC dataset was profiled on a microarray platform and the heterokaryon samples were profiled using RNA-seq, the datasets were not directly comparable. The differences between RNA-seq and microarray data arise from the fact that microarray data is treated as a continuous measurement of the fluorescence intensity, typically modeled by a log-normal distribution. RNA-seq experiments count the number of reads that map to a particular gene or transcript, and methods that analyze RNA-seq data commonly use a Negative Binomial (NB) distribution. In order to make the two datasets comparable, both expression profiles were transformed using rank and z-transformation. More specifically, the gene expression was rank-transformed for each sample, and then each gene was z-transformed across samples. The two gene expression profiles were combined after this transformation.

Singular value decomposition (SVD) is a method in linear algebra that allows for a factorization of any m×n matrix into the following form: $A_{mn}=U_{mm}S_{mn}V_{nn}^T$. When applied to gene expression data, the method can be used to bring out dominant underlying behaviors in gene expression patterns. The seminal paper by Alter et al. in 2000 was one of the first applications of the method for gene expression data. According to this study, SVD factorization of the gene expression data resulted in a transformation of the data from an N-genes and M-arrays space in to an M-"eigenarrays" and "M-ei-gengenes" space, which accounted for most of the variance, despite the great reduction in dimensionality. The proportion of variance explained by each eigengene $v(e_i)$ (or principal component) was calculated as:

$$d = \frac{1}{\log(M)} \sum_{i=1}^{M} v \sum e_i \log(v(e_i)).$$

The four reference populations—HSCs, MPPs, MLPs and Lineage-Committed Progenitors—were each filtered for quality control, removing cells with high mitochondrial read percentage or two few reads as well as genes with not enough coverage to contribute to the analysis. The samples that passed these quality control filters were pooled and normalized to CPM. A distance matrix was constructed using the Pearson distance based on the 100 most variable genes in gene expression space, and this distance matrix was used to construct a k-nearest-neighbor graph with 10 neighbors. Metacells were imputed for each cell by summing the reads of the ten nearest neighbors (using the unnormalized counts) before re-normalization and sub-sampling to 1000 metacells. These metacells were then used as input to ARACNe for the inference of a regulatory network.

The original, non-imputed CPM matrix was transformed into a gene expression signature (GES) using an internal double rank transformation. This GES was then used as the input to VIPER, along with the ARACNe network described previously, inferring the protein activity for all cells in the reference populations.

A train-test split was performed on the reference population in a 70-30 proportion, and the feature set was optimized based on the performance on the held-out set. To identify candidate feature sets, we performed a pairwise Wilcoxon-Rank-Sum test for each protein for all six possible group-to-group comparisons. Proteins were sorted in population-specific manner by the maximum p-value of their pairwise comparisons, and one feature from each populations' sorted list was added at each iteration. This approach was chosen in order to avoid a single population with bigger differences to the other three dominating the candidate features. Ultimately, a set of 43 proteins were found to have the optimum model performance. Similar optimization was carried out to refine the mtry (number of features to consider at each branch point in the random forest) parameter before a final, ten-thousand tree model was trained using the activity of the selected features in the entire reference population.

Protein activity was then inferred for the test population. The BAZ2B population was normalized against the Luciferase control using a double-rank transformation, while the Luciferase population was normalized internally. These GES were then used as the input to VIPER along with the metacell network from the reference populations. Finally, this VIPER matrix was fed into the random forest model and classified based on the maximal vote in each cell.

Random forests have the advantage of generating a class vote percentage rather than a single classification. This can be regarded as a measurement of classification confidence, a useful tool in determining how distinct members of different classes actually are. In order to visualize this, we developed a circular plotting structure where the class labels are placed at equidistant intervals along the circumference and the samples are plotted in the interior. The position of each sample within the plot is determined in polar coordinates; the radius is given by the inverse of the Shannon information entropy of the classification, while the angle (or theta) is taken as the average of the class-specific angles weighted by the squared vote percentage for each class in the given sample.

As an example, a sample where 100% of the trees in the random forest classified the sample as an HSC would be plotted on the circumference at an angle of $\pi/4$ (or 45°). A sample where the votes were split 50/50 between HSCs and MPPs would appear roughly halfway between the origin and the circumference of the circle and at an angle of $\pi/2$ (or 90°), the average of the angle for HSCs and MLPs. Finally, a sample with a totally uncertain classification—equal votes for all four classes—would appear at the origin. This method of class visualization can be extended to any number of classes or model contexts. All the raw sequencing data related to the heterokaryon, and the hematopoietic single-cell data are available on the NCBI gene expression omnibus with the accession code GSE114240.

It is to be understood that the method of generating multipotent stem cells is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of generating multipotent stem cells, comprising the step of delivering at least one reprogramming protein into somatic cells, wherein the at least one reprogramming protein comprises at least one Master Regulator (MR) protein, and wherein the step of delivering the at least one reprogramming protein into the somatic cells comprises mRNA delivery.

2. A method of generating multipotent stem cells, comprising the step of delivering at least one reprogramming protein into somatic cells, wherein the at least one reprogramming protein comprises at least one Master Regulator (MR) protein, wherein the at least one Master Regulator (MR) protein is selected from the group consisting of BAZ2B, ZBTB20, ZMAT1, CNOT8, KLF12, DMTF1, HBP1, FL11, and combinations thereof, and wherein the at least one Master Regulator (MR) protein comprises BAZ2B.

3. The method of generating multipotent stem cells as recited in claim 2, wherein the somatic cells comprise endogenous somatic cells.

4. A method of generating multipotent stem cells, comprising the step of delivering the at least one reprogramming protein into the somatic cells,
   wherein the at least one reprogramming protein comprises at least one Master Regulator (MR) protein,
   wherein the somatic cells comprise endogenous somatic cells,
   wherein the at least one Master Regulator (MR) protein is selected from the group consisting of BAZ2B, ZBTB20, ZMAT1, CNOT8, KLF12, DMTF1, HBP1, FLI1, and combinations thereof, and
   wherein the at least one Master Regulator (MR) protein comprises BAZ2B.

5. A method of identifying Master Regulator (MR) proteins involved in onset driving events of lineage-committed cells, comprising the steps of:
   a) obtaining bi-species heterokaryons by fusing embryonic stem cells (ESCs) of a first species with lineage-committed cells of a second species;
   b) tracking reprogramming of nuclei of the lineage-committed cells to a multipotent state by transcript profiling of mRNA of the second species at multiple timepoints after fusion;
   c) interrogating a regulatory network of the lineage-committed cells with gene expression signatures collected in step b) to identify candidate MR proteins; and
   d) validating the candidate MR proteins identified in step c) by ectopically expressing the candidate MR proteins in lineage-committed cells and progenitors thereof, and evaluating effectiveness of the candidate MR proteins in reprogramming committed lineage-committed cells and progenitors thereof into a multipotent state, thereby identifying MR proteins involved in onset driving events of the lineage-committed cells.

6. The method of identifying Master Regulator (MR) proteins involved in onset driving events of lineage-committed cells as recited in claim 5, wherein step c) comprises virtual inference of protein activity by enriched regulon (VIPER) analysis.

7. A somatic cell ectopically expressing one or more Master Regulator (MR) proteins selected from the group consisting of BAZ2B, ZBTB20, ZMAT1, CNOT8, KLF12, DMTF1, HBP1, and FLI1, wherein the one or more MR proteins comprise BAZ2B.

*     *     *     *     *

SEQUENCE LISTING

```
Sequence total quantity: 6
SEQ ID NO: 1            moltype = DNA   length = 25
FEATURE                 Location/Qualifiers
misc_feature            1..25
                        note = forward primer for cDNA for ZMAT1
source                  1..25
                        mol_type = other DNA
                        organism = synthetic construct
SEQUENCE: 1
gggccccatc tttattggaa aatgt                                        25

SEQ ID NO: 2            moltype = DNA   length = 25
```

-continued

```
FEATURE              Location/Qualifiers
misc_feature         1..25
                     note = reverse primer for cDNA for ZMAT1
source               1..25
                     mol_type = other DNA
                     organism = synthetic construct
SEQUENCE: 2
acctctcctt ttcttcatca ggtgt                                   25

SEQ ID NO: 3         moltype = DNA  length = 32
FEATURE              Location/Qualifiers
misc_feature         1..32
                     note = forward primer BAZ2B stop codon
source               1..32
                     mol_type = other DNA
                     organism = synthetic construct
SEQUENCE: 3
gcaaaaagaa cagataacca actttcttgt ac                           32

SEQ ID NO: 4         moltype = DNA  length = 32
FEATURE              Location/Qualifiers
misc_feature         1..32
                     note = reverse primer BAZ2B stop codon
source               1..32
                     mol_type = other DNA
                     organism = synthetic construct
SEQUENCE: 4
gtacaagaaa gttggttatc tgttcttttt gc                           32

SEQ ID NO: 5         moltype = DNA  length = 31
FEATURE              Location/Qualifiers
misc_feature         1..31
                     note = forward primer DMTF1 stop codon
source               1..31
                     mol_type = other DNA
                     organism = synthetic construct
SEQUENCE: 5
ggtaaactgt cattagccaa ctttcttgta c                            31

SEQ ID NO: 6         moltype = DNA  length = 31
FEATURE              Location/Qualifiers
misc_feature         1..31
                     note = reverse primer DMTF1 stop codon
source               1..31
                     mol_type = other DNA
                     organism = synthetic construct
SEQUENCE: 6
gtacaagaaa gttggctaat gacagtttac c                            31
```